(12) United States Patent
Kerfeld et al.

(10) Patent No.: US 11,673,923 B2
(45) Date of Patent: Jun. 13, 2023

(54) MINIMIZED CYANOBACTERIAL MICROCOMPARTMENT FOR CARBON DIOXIDE FIXATION

(71) Applicant: Board of Trustees of Michigan State University, East Lansing, MI (US)

(72) Inventors: Cheryl A. Kerfeld, Okemos, MI (US); Cesar R. Gonzalez, White Rock, NM (US)

(73) Assignee: Board of Trustees of Michigan State University, East Lansing, MI (US)

(*) Notice: Subject to any disclaimer, the term of this patent is extended or adjusted under 35 U.S.C. 154(b) by 118 days.

(21) Appl. No.: 16/670,125

(22) Filed: Oct. 31, 2019

(65) Prior Publication Data

US 2021/0206816 A1 Jul. 8, 2021

Related U.S. Application Data

(63) Continuation of application No. 15/685,742, filed on Aug. 24, 2017, now Pat. No. 10,501,508.
(Continued)

(51) Int. Cl.
| | | |
|---|---|---|
| *C12N 9/14* | (2006.01) | |
| *C07K 14/405* | (2006.01) | |
| *C10L 1/02* | (2006.01) | |
| *C12N 1/32* | (2006.01) | |
| *C12P 5/00* | (2006.01) | |
| *C12N 15/82* | (2006.01) | |
| *C12P 7/16* | (2006.01) | |
| *C12P 7/06* | (2006.01) | |
| *C12P 7/24* | (2006.01) | |

(Continued)

(52) U.S. Cl.
CPC .......... *C07K 14/405* (2013.01); *C07K 14/195* (2013.01); *C10L 1/02* (2013.01); *C12N 1/32* (2013.01); *C12N 9/14* (2013.01); *C12N 15/8261* (2013.01); *C12P 5/007* (2013.01); *C12P 7/065* (2013.01); *C12P 7/16* (2013.01); *C12P 7/24* (2013.01); *C07K 2319/00* (2013.01); *C12P 39/00* (2013.01); *Y02A 40/146* (2018.01); *Y02E 50/10* (2013.01); *Y02P 60/20* (2015.11)

(58) Field of Classification Search
None
See application file for complete search history.

(56) References Cited

U.S. PATENT DOCUMENTS

2018/0057546 A1 3/2018 Kerfeld et al.

FOREIGN PATENT DOCUMENTS

| WO | WO-2011094765 A2 | 8/2011 |
|---|---|---|
| WO | WO-2014182968 A2 | 11/2014 |
| WO | WO-2016077589 A1 | 5/2016 |

OTHER PUBLICATIONS

Gonzalez-Esquer et al. (Plant Cell, vol. 27, pp. 2637-2644, Sep. 2015, Epub Aug. 29, 2015).*

(Continued)

*Primary Examiner* — Richard G Hutson
(74) *Attorney, Agent, or Firm* — Schwegman Lundberg & Woessner, P.A.

(57) ABSTRACT

A fusion chimeric protein is described herein that can assemble a functional carboxysome core, which is able to fix carbon by taking atmospheric carbon dioxide and converting it into useful carbon-containing compounds such as 3-phosphoglycerate (3-PGA).

4 Claims, 9 Drawing Sheets
(4 of 9 Drawing Sheet(s) Filed in Color)
Specification includes a Sequence Listing.

Related U.S. Application Data

(60) Provisional application No. 62/378,979, filed on Aug. 24, 2016.

(51) Int. Cl.
    *C07K 14/195* (2006.01)
    *C12P 39/00* (2006.01)

(56) References Cited

OTHER PUBLICATIONS

Gonzalez-Esquer et al. (Plant Cell, vol. 27, Supplemental Data, Sep. 2015, Epub Aug. 29, 2015).*
"U.S. Appl. No. 15/685,742, Non Final Office Action dated Mar. 6, 2019", 16 pgs.
"U.S. Appl. No. 15/685,742, Notice of Allowability dated Sep. 19, 2019", 4 pgs.
"U.S. Appl. No. 15/685,742, Notice of Allowance dated Jul. 29, 2019", 9 pgs.
"U.S. Appl. No. 15/685,742, Response Filed Jan. 23, 2019 to Restriction Requriement dated Nov. 30, 2018", 6 pgs.
"U.S. Appl. No. 15/685,742, Response filed Jun. 6, 2019 to Non Final Office Action dated Mar. 6, 2019", 15 pgs.
"U.S. Appl. No. 15/685,742, Restriction Requirement dated Nov. 30, 2018", 7 pgs.
"U.S. Appl. No. 15/685,742, Supplemental Amendment Filed Jul. 15, 2019 to Non-Final Office Action dated Mar. 6, 2019", 4 pgs.
Aussignargues, Clement, et al., "Bacterial microcompartment assembly: The key role of encapsulation peptides", ommunicative & Integrative Biology 8:3, e1039755, (May/Jun. 2015).
Axen, Seth D., et al., "A Taxonomy of Bacterial Microcompartment Loci Constructed by a Novel Scoring Method", PLOS Comput. Biol. 10(10), e1003898., (Oct. 2014), 1-20.
Baker, Neil R., et al., "Chlorophyll Fluorescence: A Probe of Photosynthesis In Vivo", Annu. Rev. Plant Biol., 59, (2008), 89-113.
Biasini, Marco, et al., "SWISS-MODEL: modelling protein tertiary and quaternary structure using evolutionary information", Nucleic Acids Research, vol. 42, (2014), W252-W258.
Cai, Fei, et al., "Advances in Understanding Carboxysome Assembly in Prochlorococcus and Synechococcus Implicate CsoS2 as a Critical Componet", Life, 5, (2015), 1141-1171.
Cai, Fei, "Production and Characterization of Synthetic Carboxysome Shells with Incorporated Luminal Proteins1[OPEN]", Plant Physiology, vol. 170, (Mar. 2016), 1868-1877.
Cai, Fei, et al., "The Pentameric Vertex Proteins Are Necessary for the Icosahedral Carboxysome Shell to Function as a CO2 Leakage Barrier", PLoS ONE 4(10), e7521, (Oct. 2009), 1-9.
Cameron, Jeffrey C., "Biogenesis of a Bacterial Organelle: The Carboxysome Assembly Pathway", Cell, 155, (2013), 1131-1140.
Chen, Anna H., et al., "The Bacterial Carbon-Fixing Organelle is Formed by Shell Envelopment of Preassembled Cargo", PLoS ONE, 8(9), e76127, (Sep. 2013), 1-13.
Cheng, Shouqiang, et al., "Bacterial microcompartments: their properties and paradoxes", BioEssays, 30(11-12), (2008), 1084-1095.
Dragosits, Martin, et al., "Adaptive laboratory evolution—principles and applications for biotechnology", Microbial. Cell Factories, 12: 64, (2013), 17 pgs.
Drews, G., et al., "Beitrage zur Cytologie der Blaualgen [Cytology of Cyanophycea. II. Centroplasm and granular inclusions of Phormidium uncinatum].", Archiv fur Mikrobiologie, 24, II. Mitteilung Zentroplasma und granulare Einschlusse von Phormidium uncinatum, (1956), 147-162.
Frank, Stefanie, et al., "Bacterial microcompartments moving into a synthetic biological world", J. Biotechnol., 163(2), (2013), 273-279.
Gantt, E., et al., "Ultrastructure of Blue-Green Algae", J. Bacteriol., 97(3), (1969), 1486-1493.
Hunter, S., et al., "InterPro in 2011: new developments in the family and domain prediction database", Nucleic Acids Res., 40(Database Issue), (2012), D306-D312.
Kerfeld, Cheryl A., et al., "Bacterial microcompartments and the modular construction of microbial metabolism", Trends Microbiol., 23, (2015), 22-34.
Kinney, James N., et al., "Elucidating Essential Role of Conserved Carboxysomal Protein CcmN Reveals Common Feature of Bacterial Microcompartment Assembly", J. Biol. Chem. 287(21), (2012), 17729-17736.
Kufryk, G. I., "Transformation of the *Cyanobacterium synechocystis* sp. PCC 6803 as a tool for genetic mapping: optimization of efficiency", FEMS Microbiol. Lett., 206, (2002), 215-219.
Lagarde, Delphine, et al., "Increased Production of Zeaxanthin and Other Pigments by Application of Genetic Engineering Techniques to *Synechocystis* sp. Strain PCC 6803", Appl. Environ. Microbiol., 66(1), (2000), 64-72.
Landgraf, Dirk, et al., "Segregation of molecules at cell division reveals native protein localization", Nat. Methods, 9(5), (2012), 480-482.
Lawrence, Andrew D., et al., "Solution Structure of a Bacterial Microcompartment Targeting Peptide and Its Application in the Construction of an Ethanol Bioreactor", ACS Synthetic Biology, 3(7), (2014), 454-465.
Lichtenthaler, Hartmut K., "[34] Chlorophylls and Carotenoids: Pigments of Photosynthetic Biomembranes", Methods in Enzymology, 148, (1987), 350-382.
Lin, Myat T., et al., "A faster Rubisco with potential to increase photosynthesis in crops", Nature, 513(7519), (2014), 547-550.
Lin, Myat T., et al., "β-Carboxysomal proteins assemble into highly organized structures in Nicotiana chloroplasts", Plant J., 79(1), (2014), 1-12.
Lluch-Senar, Maria, et al., "Defining a minimal cell: essentiality of small ORFs and ncRNAs in a genome-reduced bacterium", Mol. Syst. Biol., 11: 780, (2015), 1-7.
Long, Benedict M., et al., "Analysis of Carboxysomes from Synechococcus PCC7942 Reveals Multiple Rubisco Complexes with Carboxysomal Proteins CcmM and CcaA", J. Biol. Chem., 282(40), (2007), 29323-29335.
Long, Benedict M., et al., "Functional Cyanobacterial b-Carboxysomes Have an Absolute Requirement for Both Long and Short Forms of the CcmM Protein1[W][OA]", Plant Physiology, 153, (May 2010), 285-293.
Marsh, Joseph A., "Protein Complexes Are under Evolutionary Selection to Assemble via Ordered Pathways", Cell, 153, (2013), 461-470.
Ngo, et al., "In the Protein Folding Problem and Tertiary Structure Prediction", K. Merz., and S. Le Grand (eds.), (1994), 492-495.
Pena, Kerry L., et al., "Structural basis of the oxidative activation of the carboxysomal ?-carbonic anhydrase,CcmM", Proc. Natl. Acad. Sci. USA, 107(6), (2010), 2455-2460.
Pettersen, Eric F., et al., "UCSF Chimera—a visualization system for exploratory research and analysis", J Comput Chem., 25(13), (2010), 1605-1612.
Price, G. Dean, et al., "Advances in understanding the cyanobacterial CO2-concentrating-mechanism (CCM): functional components, Ci transporters, diversity, genetic regulation and prospects for engineering into plants", Journal of Experimental Biology, 59(7), (2008), 1441-1461.
Price, G. D., et al., "Isolation and Characterization of High CO2-Requiing-Mutants of the Cyanobacterium Synechococcus PCC7942", Plant Physiology, 91, (1989), 514-525.
Price, G. Dean, et al., "The cyanobacterial CCM as a source of genes for improving photosynthetic CO2 fixation in crop species", Journal of Experimental Biology. 64(3), (2013), 753-768.
Reynolds, E. S., et al., "The use of lead citrate at high pH as an electron-opaque stain in electron microscopy", J. Cell Biol. 17, (1963), 208-212.
Rippka, Rosmarie, et al., "Generic Assignments, Strain Histories and Properties of Pure Cultures of Cyanobacteria", J. Gen. Microbiol., 111, (1979), 1-61.
Rokney, Assaf, "*E. coli* transports aggregated proteins to the poles by a specific and energy-dependent process", J. Mol. Biol., 392(3), (2009), 589-601.

(56) References Cited

OTHER PUBLICATIONS

Savage, Didi F., et al., "Spatially ordered dynamics of the bacterial carbon fixation machinery", Science, 327(5970), (2010), 1258-1261.
Schneider, C. A., et al., "NIH Image to ImageJ: 25 years of image analysis", Nat. Methods 9(7), (2012), 671-675.
So, Anthony K.-C., et al., "Characterization of a mutant lacking carboxysomal carbonic anhydrase from the cyanobacterium Synechocystis PCC6803", Planta 214(3), (2002), 456-467.
So, Anthony K.-C., et al., "Characterization of the C-terminal extension of carboxysomal carbonic anhydrase from *Synechocystis* sp. PCC6803", Funct. Plant Biol., 29(3), (2002), 183-194.
Takahashi, Shunichi, et al., "Interruption of the Calvin cycle inhibits the repair of Photosystem II from photodamage", Biochim. Biophys. Acta (BBA)—Bioenergetics, 1708(3), (2005), 352-361.
Zarzycki, Jan, et al., "Cyanobacteriai-based approaches to improving photosynthesis in plants", Journal of Experimental Botany, 64(3), (2013), 787-798.

\* cited by examiner

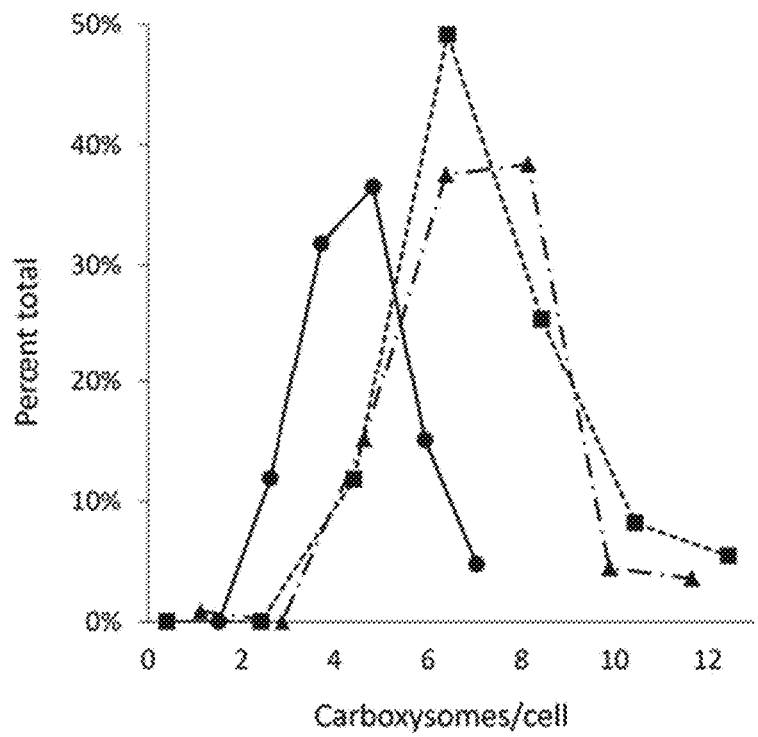
FIG. 4A
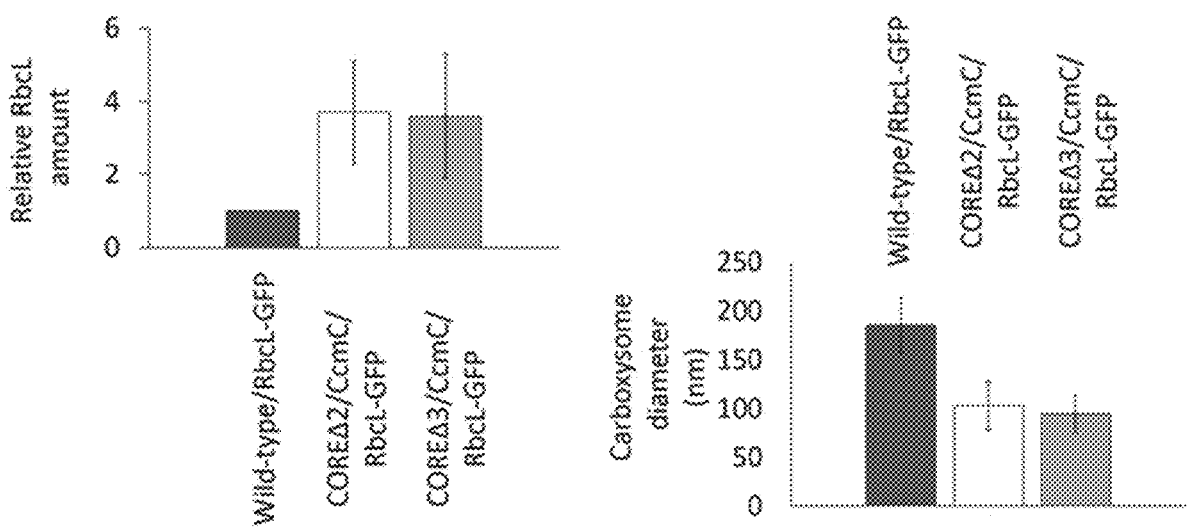
FIG. 4B
FIG. 4C

MINIMIZED CYANOBACTERIAL MICROCOMPARTMENT FOR CARBON DIOXIDE FIXATION

This application is a continuation of U.S. patent application Ser. No. 15/685,742, filed Aug. 24, 2017, which claims benefit of priority to the filing date of U.S. Provisional Application Ser. No. 62/378,979, filed Aug. 24, 2016, the contents of which are specifically incorporated herein by reference in their entirety.

FEDERAL FUNDING

This invention was made with government support under DE-FG02-91ER20021 awarded by the U.S. Department of Energy. The government has certain rights in the invention.

BACKGROUND OF THE INVENTION

Like plants and algae, cyanobacteria obtain energy from photosynthesis, utilizing energy from sunlight and electrons from water to reduce carbon dioxide ($CO_2$) and thereby 'fix' carbon into cell biomass. This photosynthetically-fixed carbon can then be used to make metabolites, such as carbohydrates, proteins, and fatty acids that are ultimately distributed to heterotrophic organisms. Besides their role as primary carbon fixation organisms, cyanobacteria can also be altered to produce useful products. For example, *Synechococcus elongatus* PCC 7942 has been engineered to produce isobutyraldehyde and butanol; *Synechocystis* sp. PCC 6803 has been modified produce ethanol and isoprene.

Cyanobacteria excel at carbon fixation, thanks to their complex carbon concentrating mechanism (ccm), which is comprised of bicarbonate pumps, carbon dioxide-uptake systems and the carboxysome. The carboxysome is an approximate 300 MDa compartment essential for carbon concentration, as it enhances carbon fixation by sequestering ribulose-1,5-bisphosphate carboxylase/oxygenase (Rubisco) and carbonic anhydrase (CA) within a protein shell. In the carboxysome lumen, bicarbonate is converted into carbon dioxide by carbonic anhydrase. Such conversion increases the proportion of carbon dioxide to oxygen in the vicinity of Rubisco, which favors Rubisco's carboxylase activity, while the shell limits the loss of carbon dioxide into the bulk cytosol (Cai et. al, 2009).

Researchers have explored ways to express the β-carboxysome shell and cyanobacterial form 1B Rubisco in chloroplasts (Lin et al., 2014b; Lin et al., 2014a). However, constructs have not been generated that can assemble the functional multi-protein metabolic carboxysome core.

SUMMARY

In cyanobacteria, the key enzyme for photosynthetic $CO_2$ fixation, ribulose-1,5-bisphosphate carboxylase/oxygenase (Rubisco), is bound within proteinaceous polyhedral microcompartments called carboxysomes. A streamlined carboxysome is described herein that was generated by fusing key domains from four proteins into a single protein. This chimeric protein assembles into a functional carboxysome core that can readily be transferred and utilized in other organisms. This is the first instance of the redesign and construction of a carboxysome core, the first instance of a re-design of a bacterial microcompartment core, and lays the base for the generation of novel compartments with industrially relevant functions based on the carboxysome and related bacterial microcompartment architectures.

Described herein are fusion proteins that include a polypeptide comprising at least two small subunit-like domains (SSLDs) from a carbon dioxide concentrating mechanism (CcmM) protein, at least one carbonic anhydrase domain, and at least one encapsulation peptide. The at least two small subunit-like domains (SSLDs) from a carbon dioxide concentrating mechanism (CcmM) protein can bind or nucleate with ribulose-1,5-bisphosphate carboxylase/oxygenase (Rubisco). The Rubisco can, for example, synthesize 3-phosphoglycerate (3-PGA). In some cases, the at least two small subunit-like domains (SSLDs) from a carbon dioxide concentrating mechanism (CcmM) protein can have a protein sequence with at least 95% sequence identity to any of SEQ ID NO:1-11, 37, 75, 76, or 77.

The at least one carbonic anhydrase domain is an enzyme that can convert bicarbonate to carbon dioxide. For example, the at least one carbonic anhydrase domain comprises at least 95% sequence identity to any of SEQ ID NO:17-21 or 71.

The at least one encapsulation peptide can interact with, nucleate, and/or bind one or more carboxysome shell protein. In some cases, the at least one encapsulation peptide comprises at least 95% sequence identity to any of SEQ ID NO:12-15 or 16.

Also described herein are expression cassettes that can include a promoter operably linked to a nucleic acid segment encoding such a fusion protein. Cells, plants, bacteria, algae, and/or microalgae can be modified to include such expression cassettes.

Methods are also described herein that can provide carbon fixation. Such methods can include culturing the cells that have nucleic acids or expression vectors that encode any of the fusion proteins described herein. The methods can involve cultivating one or more plants that have nucleic acids or expression vectors that encode any of the fusion proteins described herein. Such cells, plants, bacteria, algae, and/or microalgae can manufacture products such as 3-phosphoglycerate (3-PGA). Such cells, plants, bacteria, algae, and/or microalgae can be cultivated or cultured and then harvested. Products can be harvested from the cells, plants, bacteria, algae, and/or microalgae. Such products can include oils, carbohydrates, grains, vegetables, fruits and other components, as well as 3-phosphoglycerate (3-PGA).

DESCRIPTION OF THE FIGURES

The patent or application file contains at least one drawing executed in color. Copies of this patent or patent application publication with color drawing(s) will be provided by the Office upon request and payment of the necessary fee.

FIG. 1A is a schematic diagram of the architecture of domains in the CcmM, CcmN, CcaA and CcmC proteins that recruit Rubisco and assemble the carboxysome core. FIG. 1B schematically illustrates the architecture and structure of the domains of the constructed chimeric protein, CcmC. SSLD: Small subunit-like domain. EP: Encapsulation peptide. CA: Carbonic anhydrase. FIG. 1C is a schematic diagram of the native β-carboxysome core protein. The shell of the native β-carboxysome core protein includes the CcmL (pentagon), CcmO (hexagon), and CcmK (hexagon) polypeptides encoded by the ccm operon. The core of the native β-carboxysome core protein includes the other proteins encoded by the ccm operon. FIG. 1D is a schematic diagram of the CcaA-M35 construct, which is a fusion of CcaA and 3×SSLDs, and which was determined to not be a successful design. FIG. 1E is a schematic diagram of the M35-EP construct, which is a fusion of the Encapsulation peptide of CcmN and three SSLDs. and which was also determined to not be a successful design. FIG. 1F is a schematic diagram of the CcmC fusion of the Encapsulation peptide of CcmN, a shortened version of CcaA (central flattened circle linked to a pentagon), and three SSLDs (three rectangles at the bottom that bind or nucleate with the CcaA). The shell of the chimeric cyanobacterial carboxysome protein includes the CcmL (pentagon). CcmO (hexagon), and CcmK (hexagon) polypeptides encoded by the ccm operon. Gray shading between polypeptide domains denotes known non-covalent domain interactions. SSLD: small subunit-like domain. EP: Encapsulation peptide. FIG. 1G illustrates assembly of a native β-carboxysome core. FIG. 1H illustrates assembly of the designed carboxysome core by the chimeric protein CcmC (yellow). For FIGS. 1G and 1H, the small subunit-like domains (SSLDs) are numbered from the N-terminal (SSLD1) to C-terminal (SSLD3). The specific details of their interactions with the large subunit of Rubisco are unknown, but they may displace some of the RbcS subunits, which are not shown. Domains are colored as in FIGS. 1A and 1B. Shell proteins are shown in blue, while four RbcL subunits of the L8S8 complex of Rubisco are shown in green. Gray shading denotes known noncovalent domain interactions with a numbers in parenthesis for the corresponding reference: (1) and (2) from Kinney et al. (2012), (3) from Long et al. (2007) and (4) from Long et al. (2010).

FIG. 3 panels A-D show fluorescence of cyanobacteria strains expressing RbcL-GFP for carboxysome visualization by microscopy. FIG. 3 panel A illustrates fluorescence of wild-type/RbcL-GFP cyanobacteria. FIG. 3 panel B illustrates fluorescence of COREΔ2/RbcL-GFP cyanobacteria. FIG. 3 panel C illustrates fluorescence of COREΔ2/CcmC/RbcL-GFP cyanobacteria. FIG. 3 panel D illustrates fluorescence of COREΔ3/CcmC/RbcL-GFP cyanobacteria. Scale bar: 5 μm. FIG. 3 panels E-H show electron micrographs of the same strains after incubation for at least 12 hours in air. FIG. 3 panel E shows images of wild-type/RbcL-GFP cyanobacteria. FIG. 3 panel F shows images of COREΔ2/RbcL-GFP cyanobacteria. FIG. 3 panel G shows images of COREΔ2/CcmC/RbcL-GFP cyanobacteria. FIG. 3 panel H shows images of COREΔ3/CcmC/RbcL-GFP cyanobacteria. Arrowheads: carboxysomes. Scale bar: 500 nm.

FIG. 4A-4C illustrates the structural features of native and minimized carboxysomes. FIG. 4A graphically illustrates the distribution of the number of carboxysomes per cell (n≤100), where the solid line (solid circle symbols) shows results for wild-type/RbcL-GFP, the dash-dotted line (triangle symbols) shows results for COREΔ2/CcmC/RbcL-GFP, and the dashed line (square symbols) shows results for COREΔ3/CcmC/RbcL-GFP. FIG. 4B graphically illustrates the relative RbcL content in protein samples normalized to Chlorophyll a (n=3), where the dark gray bar shows results for wild-type/RbcL-GFP, the open (white) bar shows results for COREΔ2/CcmC/RbcL-GFP, and the light gray bar shows results for COREΔ3/CcmC/RbcL-GFP. FIG. 4C graphically illustrates the carboxysome diameters measured from electron micrographs (n=50), where the dark gray bar shows results for wild-type/RbcL-GFP, the open (white) bar shows results for COREΔ2/CcmC/RbcL-GFP, and the light gray bar shows results for COREΔ3/CcmC/RbcL-GFP. Error bars=std. dev.

FIG. 5A shows the changes in optical density (730 nm) over time of independent cultures grown in air (n=3). Wild type/RbcL-GFP (circles). COREΔ2/CcmC/RbcL-GFP (triangles), and COREΔ3/CcmC/RbcL-GFP (squares) show similar growth rates. Note that the COREΔ2/RbcL-GFP (without the CcmC construct; diamond symbols) failed to grow in air. The inset chart shows doubling times calculated by exponential regression curve fitting (see website at doubling-time.com/compute.php). FIG. 5B shows the changes in optical density (730 nm) over time of independent cultures grown in 5% $CO_2$ (n=3). Wild type/RbcL-GFP (circles). COREΔ2/CcmC/RbcL-GFP (triangles), and COREΔ3/CcmC/RbcL-GFP (squares) show similar growth rates when detected by optical density (730 nm). Error bars=std. dev. The inset chart shows doubling times calculated by exponential regression curve fitting (see website at doubling-time.com/compute.php).

FIG. 6A graphically illustrates the average absorbance spectra of whole cell suspensions normalized to Chla (663 nm), where the solid line shows data for wild-type/RbcL-GFP cells, and the dashed line shows data for COREΔ3/CcmC/RbcL-GFP cells (n=3). FIG. 6B graphically illustrates changes over time of $F_v/F_m$ in cultures grown at 3% $CO_2$ and transferred to air at time=0 h. where the solid line shows data for wild-type/RbcL-GFP cells (circle symbols), the dashed line shows data for COREΔ3/CcmC/RbcL-GFP cells (square symbols), and the dashed, dotted line shows data for COREΔ2/RbcL-GFP cells (triangle symbols) (n=3). FIG. 6C graphically illustrates oxygen evolution rates (normalized to Chl a) at high light intensity of strains grown in air and supplemented with 10 mM bicarbonate (left) with a comparison of Chl a per ml of $OD_{730}$ culture (right), where the dark grey bars are data for wild-type/RbcL-GFP cells and the light grey bars are data for COREΔ3/CcmC/RbcL-GFP cells. (n≤5). Error bars=std. dev.

DETAILED DESCRIPTION

A chimeric protein is described herein that can assemble into a functional carboxysome core and that is able to fix carbon by taking atmospheric carbon dioxide and converting it into useful carbon-containing molecules such as 3-phosphoglycerate (3-PGA or also referred to as glycerate 3-phosphate). 3PGA is a precursor for other useful molecules such as serine, which, in turn, can create cysteine and glycine through the homocysteine cycle.

Figure 1A:
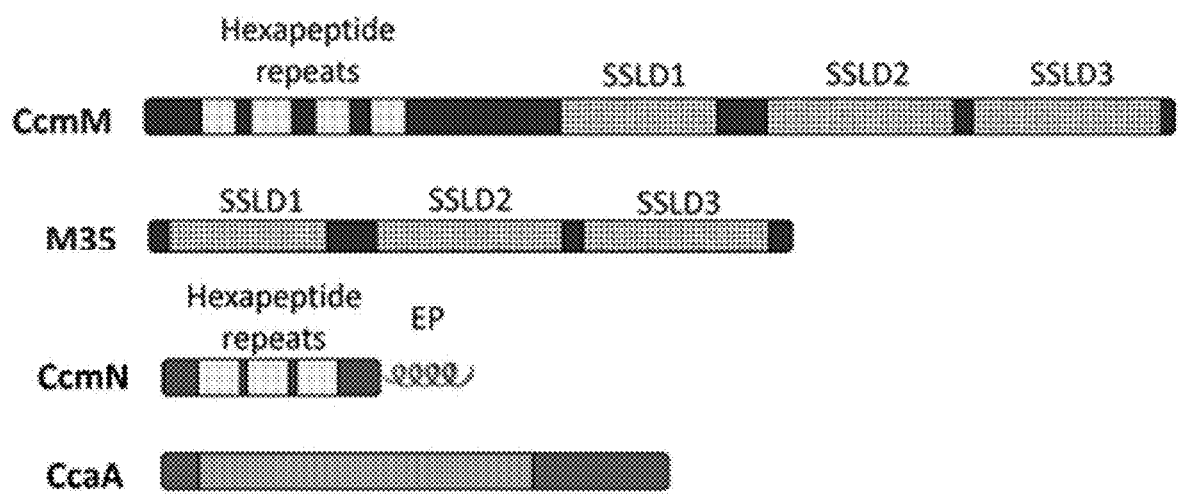
FIG. 1A-1H illustrate construction of a chimeric cyanobacterial carboxysome core.
Figure 1B:
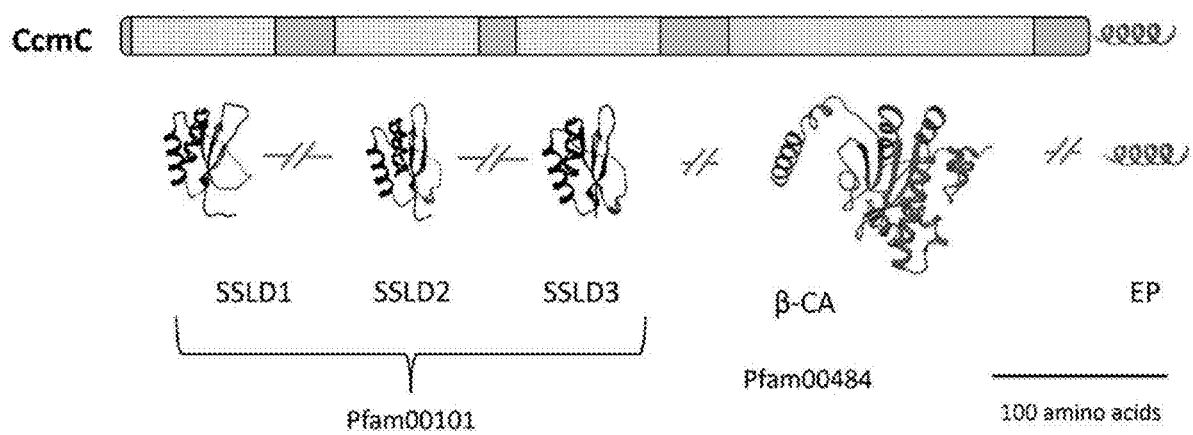
Figure 1C:
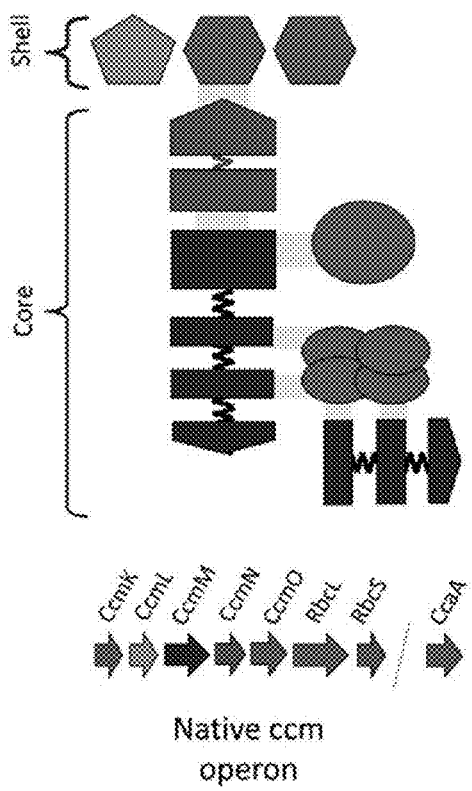

The chimeric protein is referred to as CcmC (where the final "C" is for chimeric). The CmcC protein structure is schematically illustrated in FIGS. 1B and 1H. The chimeric CcmC protein can be expressed in a variety of organisms. For example, although the CcmC protein has been generated from cyanobacterial components, it can be expressed in a variety of organisms such as bacteria, plants, microalgae and other organisms to assemble organelles that remove carbon dioxide from the atmosphere and provide organic carbon to facilitate growth and synthesis of useful products. The chimeric protein does not exist in nature, it was designed and synthesized recombinantly.

The chimeric protein structurally and functionally replaces four gene products required for carboxysome formation (see schematic illustrations in FIGS. 1B and 1H). The CcmC protein contains scaffolding domains (the Small RbcS subunit-like domains that are involved in nucleating Ribulose-1,5-bisphosphate carboxylase/oxygenase (commonly known by the abbreviation Rubisco), an enzymatic domain (carbonic anhydrase), and an encapsulating domain (the encapsulation peptide).

Functional carboxysomes are needed for the survival of a cyanobacterial host. As illustrated herein, the chimeric CcmC protein can replace the function of native carboxysomes in cyanobacteria.

In CcmC, the small subunit-like domains (SSLDs) and the Encapsulation peptide (EP) are fused to opposite ends of the beta-carbonic anhydrase (β-CA) domain. The SSLDs are available to interact with the large subunit of Rubisco and the Encapsulation peptide can interact with the shell (see FIGS. 1H and 1B). The resulting 67 kDa chimeric protein replaces the 58 kDa CcmM, the 35 kDa M35, the 16 kDa CcmN, and the 30 kDa CcaA proteins that are part of the native (wild type) cyanobacterial carboxysome core protein.

The CcmC construct reduces the genomic load required to assemble a carboxysome by about 1100 bp, which is about 18% of total message required for wild type carboxysomes. In addition, it reduces the number of proteins and, concomitantly, the need to balance the expression levels of four different genes.

Figure 5B:
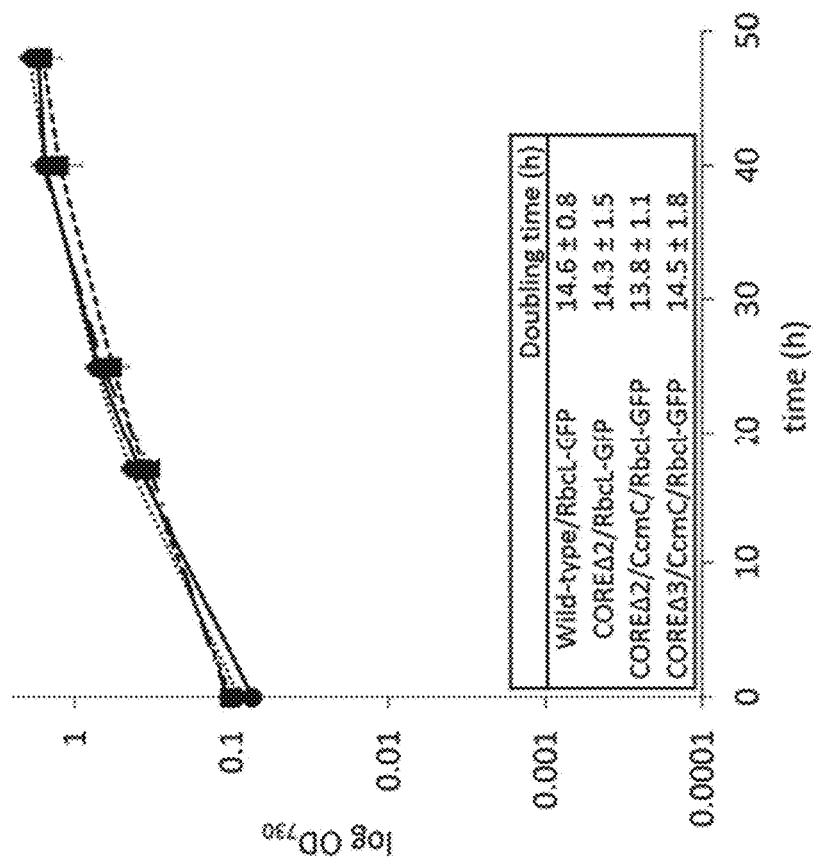
FIG. 5A-5B illustrate growth of CcmC strains compared to wild type showing that functional complementation has occurred of the carboxysome core deletion by the chimeric protein, CcmC.
Figure 5A:
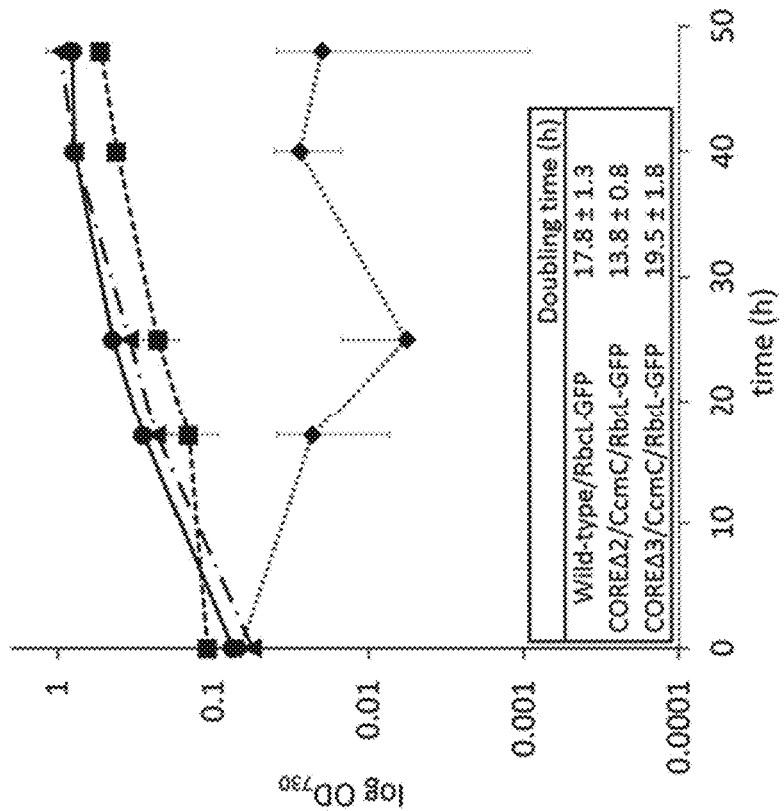

The chimeric CcmC carboxysomes, although smaller, morphologically resemble wild-type carboxysomes (FIG. 3) and they are able to support photosynthesis (FIG. 5A-5B). The results provided herein demonstrate that at least four protein domains can be combined into one, and that a non-native fusion protein can be enclosed in carboxysome shells by including a single encapsulating domain (the EP) as part of the chimeric CcmC protein.

Carboxysomes

Bacterial microcompartments (BMCs) are a family of architecturally similar but functionally diverse self-assembling organelles composed entirely of protein (Axen et al., 2014; Kerfeld and Erbilgin, 2015). The first BMC identified was the carboxysome (Drews and Niklowitz, 1956). Carboxysomes are about 300 MDa in size. Carboxysomes form compartments (Cheng et al., 2008) that are part of the cyanobacterial carbon concentrating mechanism (ccm) that enhance carbon fixation by sequestering ribulose-1,5-bisphosphate carboxylase/oxygenase (Rubisco) and carbonic anhydrase (CA) within a protein shell. In the carboxysome lumen, bicarbonate is converted into carbon dioxide by a carbonic anhydrase (CA), which increases the proportion of carbon dioxide to oxygen in the vicinity of Rubisco while the carboxysome shell limits the loss of carbon dioxide into the bulk cytosol (Cai et. al, 2009). Such increased concentration of carbon dioxide favors Rubisco's carboxylase activity. The product of carbon fixation, 3-phosphoglycerate (3-PGA), exits the carboxysome and can be used in the Calvin cycle or other biosynthetic pathways. Rubisco is the most abundant protein in the biosphere and is responsible for the majority of Earth's primary production of biomass.

Two types of carboxysomes are found in cyanobacteria: α-carboxysomes containing form 1A Rubisco, and β-carboxysomes containing form 1B Rubisco. The constituent core proteins also differ between the two types of carboxysomes, as well as the mode of assembly. Recently it was proposed that a large, conserved multi-domain protein (CsoS2) organizes the Rubisco in the α-carboxysome core (Cai et al., 2015). In contrast, assembly of the β-carboxysome involves a sequence of protein domain interactions among multiple core proteins (Cameron et al., 2013).

In *Synechococcus elongatus* PCC 7942, the β-carboxysome shell is formed by the structural proteins CcmK, CcmL and CcmO. The core of native carboxysomes is composed of CcmM, M35 and CcmN as well as the enzymes Rubisco (form 1B) and the β-carbonic anhydrase, CcaA (FIG. 1G).

CcmM Protein

The carbon dioxide concentrating mechanism protein, CcmM, can exist as 58-kDa and 35-kDa protein products in *Synechococcus elongatus* PCC 7942. The relative composition of the 58-kDa and 35-kDa CcmM proteins is not affected by protease inhibitors. FIG. 1A shows a schematic diagram of the CcmM protein.

An amino acid sequence for a *Synechococcus elongatus* PCC 7942 carbonate dehydratase (CcmM: Synpcc7942_1423; 57833 daltons) is available as accession number ABB57453 (see website at uniprot.org/uniprot/Q03513)(SEQ ID NO:1).

```
  1  MPSPTTVPVA TAGRLAEPYI DPAAQVHAIA SIIGDVRIAA
 41  GVRVAAGVSI RADEGAPFQV GKESILQEGA VIHGLEYGRV
 81  LGDDQADYSV WIGQRVAITH KALIHGPAYL GDDCFVGFRS
121  TVFNARVGAG SVIMMHALVQ DVEIPPGRYV PSGAIITTQQ
161  QADRLPEVRP EDREFARHII GSPPVIVRST PAATADFHST
201  PTPSPLRPSS SEATTVSAYN GQGRLSSEVI TQVRSLLNQG
241  YRIGTEHADK RRFRTSSWQP CAPIQSTNER QVLSELENCL
281  SEHEGEYVRL LGIDTNTRSR VFEALIQRPD GSVPESLGSQ
321  PVAVASGGGR QSSYASVSGN LSAEVVNKVR NLLAQGYRIG
361  TEHADKRRFR TSSWQSCAPI QSSNERQVLA ELENCLSEHE
401  GEYVRLLGID TASRSRVFEA LIQDPQGPVG SAKAAAAPVS
441  SATPSSHSYT SNGSSSSDVA GQVRGLLAQG YRISAEVADK
481  RRFQTSSWQS LPALSGQSEA TVLPALESIL QEHKGKYVRL
521  IGIDPAARRR VAELLIQKP
```

A related CcmM protein from *Synechococcus elongatus* has a sequence has at least 99% sequence identity to SEQ ID NO: 1, as illustrated below (SEQ ID NO:2).

```
99.8% identity in 539 residues overlap; Score: 2722.0; Gap frequency: 0.0%
Seq1    1   MPSPTTVPVATAGRLAEPYIDPAAQVHAIASIIGDVRIAAGVRVAAGVSIRADEGAPFQV
Seq2    1   MPSPTTVPVATAGRLAEPYIDPAAQVHAIASIIGDVRIAAGVRVAAGVSIRADEGAPFQV
            ************************************************************
```

```
Seq1    61    GKESILQEGAVIHGLEYGRVLGDDQADYSVWIGQRVAITHKALIHGPAYLGDDCFVGFRS
Seq2    61    GKESILQEGAVIHGLEYGRVLGDDQADYSVWIGQRVAITHKALIHGPAYLGDDCFVGFRS
              ************************************************************

Seq1   121    TVFNARVGAGSVIMMHALVQDVEIPPGRYVPSGAIITTQQQADRLPEVRPEDREFARHII
Seq2   121    TVFNARVGAGSVIMMHALVQDVEIPPGRYVPSGAIITTQQQADRLPEVRPEDREFARHII
              ************************************************************

Seq1   181    GSPPVIVRSTPAATADFHSTPTPSPLRPSSSEATTVSAYNGQGRLSSEVITQVRSLLNQG
Seq2   181    GSPPVIVRSTPAATADFHSTPTPSPLRPSSSEATTVSAYNGQGRLSSEVITQVRSLLNQG
              ************************************************************

Seq1   241    YRIGTEHADKRRFRTSSWQPCAPIQSTNERQVLSELENCLSEHEGEYVRLLGIDTNTRSR
Seq2   241    YRIGTEHADKRRFRTSSWQPCAPIQSTNERQVLSELENCLSEHEGEYVRLLGIDTNTRSR
              ************************************************************

Seq1   301    VFEALIQRPDGSVPESLGSQPVAVASGGGRQSSYASVSGNLSAEVVNKVRNLLAQGYRIG
Seq2   301    VFEALIQRPDGSVPESLGSQPVAVASGGGRQSSYASVSGNLSAEVVNKVRNLLAQGYRIG
              ************************************************************

Seq1   361    TEHADKRRFRTSSWQSCAPIQSSNERQVLAELENCLSEHEGEYVRLLGIDTASRSRVFEA
Seq2   361    TEHADKRRFRTSSWQSCAPIQSSNERQVLAELENCLSEHEGEYVRLLGIDTASRSRVFEA
              ************************************************************

Seq1   421    LIQDPQGPVGSAKAAAAPVSSATPSSHSYTSNGSSSSDVAGQVRGLLAQGYRISAEVADK
Seq2   421    LIQDPQGPVGSAKAAAAPVSSATPSSHSYTSNGSSSSDVAGQVKGLLAQGYRISAEVADK
              ******************************************* ****************

Seq1   481    RRFQTSSWQSLPALSGQSEATVLPALESILQEHKGKYVRLIGIDPAARRRVAELLIQKP
Seq2   481    RRFQTSSWQSLPALSGRSEATVLPALESILQEHKGKYVRLIGIDPAARRRVAELLIQKP
              **************** ******************************************
```

This related protein has a sequence that is available from the National Center for Biotechnology Information database (see website at ncbi.nlm.nih.gov) with accession number WP_011242447.1 (GI:499561664), and with the sequence shown below (SEQ ID NO:2)

```
  1   MPSPTTVPVA TAGRLAEPYI DPAAQVHAIA SIIGDVRIAA
 41   GVRVAAGVSI RADEGAPFQV GKESILQEGA VIHGLEYGRV
 81   LGDDQADYSV WIGQRVAITH KALIHGPAYL GDDCFVGFRS
121   TVFNARVGAG SVIMMHALVQ DVEIPPGRYV PSGAIITTQQ
161   QADRLPEVRP EDREFARHII GSPPVIVRST PAATADFHST
201   PTPSPLRPSS SEATTVSAYN GQGRLSSEVI TQVRSLLNQG
241   YRIGTEHADK RRFRTSSWQP CAPIQSTNER QVLSELENCL
281   SEHEGEYVRL LGIDTNTRSR VFEALIQRPD GSVPESLGSQ
321   PVAVASGGGR QSSYASVSGN LSAEVVNKVR NLLAQGYRIG
361   TEHADKRRFR TSSWQSCAPI QSSNERQVLA ELENCLSEHE
401   GEYVRLLGID TASRSRVFEA LIQDPQGPVG SAKAAAAPVS
441   SATPSSHSYT SNGSSSSDVA GQVRGLLAQG YRISAEVADK
481   RRFQTSSWQS LPALSGRSEA TVLPALESIL QEHKGKYVRL
521   IGIDPAARRR VAELLIQKP
```

A related CcmM protein from *Prochlorothrix hollandica* has a sequence has at least 53% sequence identity to SEQ ID NO: 1.as illustrated below (SEQ ID NO:3).

```
51.5% identity in 563 residues overlap; Score: 1331.0; Gap frequency: 4.8%
Seq1     3    SPTTVPVATAGRLAEPYIDPAAQVHAIASIIGDVRIAAGVRVAAGVSIRADEGAPFQVGK
Seq3     5    SSAAPPTPWSRGLAEPQIDGSAYVHAFSNVIGDVWIGENVLIAPGTSIRADEGAPFHIGS
              *    *    **** **  * ***    **** *    * * * *********     *

Seq1    63    ESILQEGAVIHGLEYGRVLGDDQADYSVWIGQRVAITHKALIHGPAYLGDDCFVGFRSTV
Seq3    65    STNIQDGVVIHGLEQGRVLGDDQKEYSVWVGRDSSLTHKALIHGPAYVGDECFIGFRSTV
              *   * ****** ********    *** *     *********** ** ** ******

Seq1   123    FNARVGAGSVIMMHALVQDVEIPPGRYVPSGAIITTQQQADRLPEVRPEDREFARHIIGS
Seq3   125    FNARVGHGCIVMMHALIQDVEIPPGKYVPSGAIITSQQQADRLPDVRQEDKDFAHHVVGI
              ****** *  ****** ******** ******** ******** ** ** ** *  *

Seq1   183    PPVIVRSTPAATADFHSTPTPSPLRPSSSEAT-----------TVSAYNGQGRLSSEVI
Seq3   185    NEALLAGYHCARSSACINPIRAGLSQTFQGSTPGTHGLEESINGTTNTMNNGYGLSPALI
                                           *  *       *  *    * *   **  *

Seq1   231    TQVRSLLNQGYRIGTEHADKRRFRTSSWQPCAPIQSTNERQVLSELENCLSEHEGEYVRL
Seq3   245    SQVRSLLAQGYRIGTEHATPRRFKTSSWESCAPIESKNEGQVLSALSGCLQEHQGEYVRL
              ****** ***********  *** ****  **** * ** *** *  ** ** ******
```

```
Seq1  291  LGIDTNTRSRVFEALIQRPDGSVPE--SLGSQPVAVASGGGRQSSYASVSGNLSAEVVNK
Seq3  305  LGIDVQARRRVLEVLIQRPDGKPTSLSTRGTVSVAAPSASNGHRSSTAGTSNGGGSLADQ
           ****  *  **  *  *******        **  *       *        *

Seq1  349  VRNLLAQGYRIGTEHADKRRFRTSSWQSCAPIQSSNERQVLAELENCLSEHEGEYVRLLG
Seq3  365  VRGLLQQGCRITTEHADKRRFKTSSWQVGAVIESSNFNQVMAALDSAMQQYSGEYVRLIA
           ** ** ** ** ********* *****  *  *** ** * *         ******

Seq1  409  IDTASRSRVFEALIQDPQGPVGSAKAAAAPVSSATPSSHSYTSNGSSSS----------
Seq3  425  VDPLAKRRVAEVLIHRPDKPVATTAASKGSTYSSNGASNGASSNGYGGGSVSGLS
            *    ** ** **  * *        **         *** **

Seq1  458  -DVAGQVRGLLAQGYRISAEVADKRRFQTSSWQSLPALSGQSEATVLPALESILQEHKGK
Seq3  485  GETANQVRGWLGQGYRISAEYADKRRFKTGSWQTHGTLEGRGDQ-VLGSISTVLSTHSGN
                 **** * ******** ****** *  ***       *    **    * *

Seq1  517  YVRLIGIDPAARRRVAELLIQKP
Seq3  544  YVRLVGVDPQAKRRVGQVIIQRP
           ****  * ** * ***     ** *
```

This related CcmM protein from *Prochlorothrix hollandica* has a sequence that is available from the National Center for Biotechnology Information database (see website at ncbi.nlm.nih.gov) with accession number WP_017713783.1 (GI:516317089), and with the sequence shown below (SEQ ID NO:3).

```
  1  MAGYSSAAPP TPWSRGLAEP QIDGSAYVHA FSNVIGDVWI
 41  GENVLIAPGT SIRADEGAPF HIGSSTNIQD GVVIHGLEQG
 81  RVLGDDQKEY SVWVGRDSSL THKALIHGPA YVGDECFIGF
121  RSTVFNARVG HGCIVMMHAL IQDVEIPPGK YVPSGAIITS
161  QQQADRLPDV RQEDKDFAHH VVGINEALLA GYHCARSSAC
201  INPIRAGLSQ TFQGSTPGTH GLEESINGTT NTMNNGYGLS
241  PALISQVRSL LAQGYRIGTE HATPRREKTS SWESCAPIES
281  KNEGQVLSAL SGCLQEHQGE YVRLLGIDVQ ARRRVLEVLI
321  QRPDGKPTSL STRGTVSVAA PSASNGHRSS TAGTSNGGGS
361  LADQVRGLLQ QGCRITTEHA DKRRFKTSSW QVGAVIESSN
401  FNQVMAALDS AMQQYSGEYV RLIAVDPLAK RRVAEVLIHR
441  PDGKPVATTA ASKGSTYSSN GASNGASNGA SSNGYGGGSV
481  SGLSGETANQ VRGWLGQGYR ISAEYADKRR FKTGSWQTHG
521  TLEGRGDQVL GSISTVLSTH SGNYVRLVGV DPQAKRRVGQ
561  VIIQRP
```

A related CcmM protein from *Hassallia byssoidea* has a sequence has at least 53% sequence identity to SEQ ID NO:1, as illustrated below. Asterisks below the compared sequences indicate amino acid identity at that position (SEQ ID NO:4).

```
52.5% identity in 541 residues overlap; Score: 1402.0; Gap frequency: 1.1%

Seq1    3  SPTTVPVATAGRLAEPYIDPAAQVHAIASIIGDVRIAAGVRVAAGVSIRADEGAPFQVGK
Seq4    5  STAAPPTPWSRNLAEPNIDATAYIHPFSNVIGDVRIGANVTVAPGTSIRADEGTPFNISE
            *  *   **** **  *      ****** *  ** * ******** **  **

Seq1   63  ESILQEGAVIHGLEYGRVLGDDQADYSVWIGQRVAITHKALIHGPAYLGDDCFVGFRSTV
Seq4   65  NINLQDGVVIHGLEQGKVIGDDDNQYSVWIGKNASITHMALIHGPAYVGDDCELGEKSTV
           **  * ****** ** *  ****    ****  *** * ****** *******  ***

Seq1  123  FNARVGAGSVIMMHALVQDVEIPPGRYVPSGAIITTQQQADRLPEVRPEDREFARHIIGS
Seq4  125  FNARVGNGCIVMMHALIQDVEIPPGKYVPSGAIITNQQQADRLPDVQVQDREFSHHVVGI
           ****** *  ****** ******** *********  *********  * ****    *  *

Seq1  183  PPVIVRSTPAATADFHSTPTPSPLRPSSSFATTVSAYNGQG----RLSSEVITQVRSLLN
Seq4  185  NQAL-RSGYLCAADNKCIKNIRNEMTSSYKTNGSNGYSGNGYVSSNLSSETVQQVRHLLE
                **       **           **    *   *    ****    *** **

Seq1  239  QGYRIGTEHADKRRFRTSSWQPCAPIQSTNERQVLSELENCLSEHEGEYVRLLGIDTNTR
Seq4  244  QGYRIGTEHVDQRRFRTGSWASCSPIATNSTSEAIAALESCLAEHSGEFVRLFGIDPKGK
           *** *****  * ****  * * ***  * **      *  **** ***  ***  ***

Seq1  299  SRVFEALIQRPDGSVPESLGSQPVAVASGGGRQSSYASVSGNLSAEVVNKVRNLLAQGYR
Seq4  304  RRVLETIIQRPDGVVQNGT-TPKLGVKSASYSGGNSYSGSSTLSGEAIEQVRQLLAGGYK
            ** *  ****** *         *   *  ***    **     **  ** *** * *

Seq1  359  IGTEHADKRRFRTSSWQSCAPIQSSNERQVLAELENCLSEHEGEYVRLLGIDTASRSRVF
Seq4  363  IGMEHVDKRRFRTGSWQSCTPIASSNEKEVISALEACVASHTGEYVRLVGIEPKARKRVL
           ** ** *******  ***** *** ***  *    *** *     ******* **   *  * **
```

```
Seq1  419  EALIQDPQGPVGSAKAAAAPVSSATPSSHSYTSNGSSSSDVAGQVRGLLAQGYRISAEVA
Seq4  423  ESIIQRPDGNVAEGSSNKFVASSSSESRTSTNASTRLSPEVIDQLRQLINQGSKISAEHV
           *  ** * *           **  *  *       *  *  * *  **  ****

Seq1  479  DKRRFQTSSWQSLPALSGQSEATVLPALESILQEHKGKYVRLIGIDPAARRRVAELLIQK
Seq4  483  DKRRFRTGSWASCGQIQGNSEREAIAALEGYLREYQGEYVRLIGIEPKAKKRVLESIIQR
           ***** * **  *     * **       *** * *  ******* *  ** *  ** **

Seq1  539  P
Seq4  543  P
           *
```

This related CcmM protein from *Hassallia byssoidea* has a sequence that is available from the National Center for Biotechnology Information database (see website at ncbi.nlm.nih.gov) with accession number WP_039748670.1 (GI:748175120), and with the sequence shown below (SEQ ID NO:4).

```
  1  MAVRSTAAPP TPWSRNLAEP NIDATAYIHP FSNVIGDVRI
 41  GANVIVAPGT SIRADEGIPE NiSENTNLQD GVVIHGLEQG
 81  RVIGDDDNQY SVWIGKNASI THMALIHGPA YVGDDCFIGF
121  RSTVFNARVG NGCIVMMHAL IQDVEIPPGK YVPSGAIITN
161  QQQADRLPDV QVQDREFSHH VVGINQALRS GYLCAADNKC
201  IKNIRNEMTS SYKTNGSNGY SGNGSVSSNL SSETVQQVRH
241  LLEQGYQIGT EHVDQRRFRT GSWASCSPIA TNSTSEAIAA
281  LESCLAEHSG EFVRLFGIDP KGKRRVLETI IQRPDGVVQN
321  GTTPKLGVKS ASYSGGNSYS GSSTLSGEAI EQVRQLLAGG
361  YKIGMEHVDK RRFRTGSWQS CTPIASSNEK EVISALEACV
401  ASHTGEYVRL VGIEPKARKR VLESIIQRPD GNVAEGSSNK
441  FVASSSSESR TSTNASTRLS PEVIDQLRQL INQGSKISAE
481  HVDKRRFRTG SWASCGQIQG NSEREAIAAL EGYLREYQGE
521  YVRLIGIEPK AKKRVLESII QRPDDSVAQS SRSDNQVVAS
561  SSSSTSKTSN TATSTRLSSE VVDQLRQLRN QGSKISVEHV
601  DQRRFRTGSW TSGGQIQGNS EREAIAALEG YLREYEGEYV
641  RLIGINPKDK RRVLETIIQR P
```

CcmM comprises an N-terminal γ-CA domain followed by three small subunit-like domains (SSLDs) with sequence homology to RbcS the small subunit of Rubisco (Long et al., 2007).

M35S Protein

The ccmM gene encodes two essential carboxysome components, the full-length protein and a truncated form containing only the SSLDs (known as M35 in *Synechococcus elongatus* PCC 7942). In *Synechococcus*, the short form is composed of three SSLDs, which are believed to aggregate Rubisco. An amino acid sequence for the CcmM short form from *Synechococcus elongatus* PCC 7942 is shown below as SEQ ID NO:5, where the SSLD domains are identified in bold and with underlining.

```
215  TVSAYN GQGRLSSEVI TQVRSLLNQG YRIGTEHADK
251  RRFRTSSWQP CAPIQSTNER QVLSELENCL SEHEGEYVRL
291  LGIDTNTRSR VFEALIQRPD GSVPESLGSQ PVAVASGGGR
331  QSSYASVSGN LSAEVVNKVR NLLAQGYRIG TEHADKRRFR
371  TSSWQSCAPI QSSNERQVLA ELENCLSEHE GEYVRLLGID
411  TASRSRVFEA LIQDPQGPVG SAKAAAAPVS SATPSSHSYT
451  SNGSSSSDVA GQVRGLLAQG YRISAEVADK RRFQTSSWQS
491  LPALSGQSEA TVLPALESIL QEHKGKYVRL IGIDPAARRR
531  VAELLIQKP
```

As illustrated, an SSLD can include any of SEQ ID NOs: 75-77.

```
                                            (SEQ ID NO: 75)
215       TVSAYN GQGRLSSEVI TQVRSLLNQG YRIGTEHADK
251  RRFRTSSWQP CAPIQSTNER QVLSELENCL SEHEGEYVRL
291  LGIDTNTRSR VFEALIQRP (SEQ ID NO: 76)
331            SAEVVNKVR NLLAQGYRIG TEHADKRRFR
371  TSSWQSCAPI QSSNERQVLA ELENCLSEHE GEYVRLLGID
411  TASRSRVFEA LIQDP (SEQ ID NO: 77)
451       SSSDVA GQVRGLLAQG YRISAEVADK RRFQTSSWQS
491  LPALSGQSEA TVLPALESIL QEHKGKYVRL IGIDPAARRR
531  VAELLIQKP
```

```
57.1% identity in 326 residues overlap; Score: 877.0; Gap frequency: 4.0%
Seq5   11  LSSEVITQVRSLLNQGYRIGTEHADKRRFRTSSWQPCAPIQSTNERQVLSELENCLSEHE
Seq6  228  LDAAIVSQVRSLLAQGYRIGSEHADKRRFQTSSWQSCPSITSTNESQVLAGIESCMSEHQ
             *   ****** ******** ******** ***** * *  **** ***      *** ***

Seq5   71  GEYVRLLGIDTNTRSRVFEALIQRPDGSVPESLGSQPVAVASGGGRQSSYASVSGNLSAE
Seq6  288  GEYVRLIGIDTQARQRVLETIIQRPDGPVKSASISSVTKTIK--NYTTSHISSSGNIDAE
           ****** ****  *  * * * ******  *  *  *           *   *  *** ***
```

-continued

```
Seq5  131  VVNKVRNLLAQGYRIGTEHADKRRFRTSSWQSCAPIQSSNERQVLAELENCLSEHEGEYV
Seq6  346  TIAHVRSLLGQGYRIGTEHADARRFQTSSWQSCSPIASQQESQVVAALEACIVEHQGEYV
           ** ** *********** *** ****** **  *  * ** ** *  ** ****

Seq5  191  RLLGIDTASRSRVFEALIQDPQGPVGSAKAAAAPVSSATPSSH----SYTSNGSSS----
Seq6  406  RMLGIDTQAKQRVFEAIIQRPSDKPKAAPKASRPASTSSSSSSYASPSYASSSPNSGTST
           * *****     ***** ** *     *   * *   **     ** **     *

Seq5  243  ---SDVAGQVRGLLAQGYRISAEVADKRRFQTSSWQSLPALSGQSEATVLPALESILQEH
Seq6  466  GLGADAIAQVRSLLAQGYRVGYEYADKRRFQTSSWQSCTPINSQQESQVIAALESCIAEH
              *  *** *******  * * ************** *  * ****  *  ****  **

Seq5  300  KGKYVRLIGIDPAARRRVAELLIQKP
Seq6  526  PGNYVRLIGIDPKAKRRVLEVIIQRP
             * ********* *  *** * ** *
```

This related protein from *Acaryochoris marina* has a sequence that is available from the National Center for Biotechnology Information database (see website at ncbi.nhn.nih.gov) with accession number WP_012165581.1 (GI:501116295), and with the full length sequence shown below (SEQ ID NO:6).

```
  1  MVIHSPSTSA SMQAGNLPDP RVSSSAYVHS FAKVMGDVHV
 41  GANALIAPGS TIQADQGLPF HIGDNVNIQD GAVIHAIEPG
 81  QVRGKDGQNY AVWIGNNSCV THMALIHGPA FIGDNCFIGE
121  RSTVFNAKVG DNCVIMMHAL IQGVEIPPGK YVPSGAVITK
161  QEQANLLPDV LESDRKFTQQ IIHVNEALKS EISGASTKTS
201  IRPARANIGH SQSHRFTTDT KPMNHTTLDA AIVSQVRSLL
241  AQGYRIGSEH ADKRRFQTSS WQSCPSITST NESQVLAGIE
281  SCMSEHQGEY VRLIGIDTQA RQRVLETIIQ RPDGPVKSAS
321  ISSVTKTIKN YTTSHISSSG NIDAETIAHV RSLLGQGYRI
361  GTEHADARRF QTSSWQSCSP IASQQESQVV AALEACIVEH
401  QGEYVRMLGI DTQAKQRVFE AIIQRPSDKP KAAPKASRPA
441  STSSSSSSYA SPSYASSSPN SGTSTGLGAD AIAQVRSLLA
481  QGYRVGYEYA DKRRFQTSSW QSCTPINSQQ ESQVIAALES
521  CIAEHPGNYV RLIGIDPKAK RRVLEVIIQR PDSNSKASPS
561  APKARPASSS SSYSSKVESN SSSYRPAPSA GLDGTVVNQI
601  RSLLAQGYRI GTEYADKRRF QTSSWQSCTP IASQQESQVI
641  AGVEACMAEH PNDYVRLIGI DKRAKRRMSE TTIQRPGGST
681  ATSSSVKTSS SRSYQAPAAK SSRGRGFSPR NGGSLDADTV
721  AQVRSLLAQG YRISTEYADK RRFQTSSWQS CPPIKTQQES
761  QVIAALESCM ADHQKEYVRL IGIDTNAKRR VLESVIQKPV
801  AAH
```

The short form CcmM portion of this *Acarvychloris marina* related protein contains five SSLDs and is shown below as SEQ ID NO:7.

```
                                    KPMNHTTLDA AIVSQVRSLL
241  AQGYRIGSEH ADKRRFQTSS WQSCPSITST NESQVLAGIE
281  SCMSEHQGEY VRLIGIDTQA RQRVLETIIQ RPDGPVKSAS
321  ISSVTKTIKN YTTSHISSSG NIDAETIAHV RSLLGQGYRI
361  GTEHADARRF QTSSWQSCSP IASQQESQVV AALEACIVEH
401  QGEYVRMLGI DTQAKQRVFE AIIQRPSDKP KAAPKASRPA
441  STSSSSSSYA SPSYASSSPN SGTSTGLGAD AIAQVRSLLA
481  QGYRVGYEYA DKRRFQTSSW QSCTPINSQQ ESQVIAALES
521  CIAEHPGNYV RLIGIDPKAK RRVLEVIIQR PDSNSKASPS
561  APKARPASSS SSYSSKVESN SSSYRPAPSA GLDGTVVNQI
601  RSLLAQGYRI GTEYADKRRF QTSSWQSCTP IASQQESQVI
641  AGVEACMAEH PNDYVRLIGI DKRAKRRMSE TTIQRPGGST
681  ATSSSVKTSS SRSYQAPAAK SSRGRGFSPR NGGSLDADTV
721  AQVRSLLAQG YRISTEYADK RRFQTSSWQS CPPIKTQQES
761  QVIAALESCM ADHQKEYVRL IGIDTNAKRR VLESVIQKPV
801  AAH
```

Some forms of CcmM can have a few aminoacids missing from the N-terminus or the C-terminus of the short form CcmM protein. In addition, the N-terminus of the short form CcmM protein can have a methionine.

A related short form CcmM protein from *Thermosynechococcus elongatus* BP-1 has a sequence has at least 49% sequence identity to SEQ ID NO:5, as illustrated below.

```
48.1% identity in 316 residues overlap; Score: 685.0; Gap frequency: 3.8%
Seq5   11  LSSEVITQVRSLLNQGYRIGTEHADKRRFRTSSWQPCAPIQSTNERQVLSELENCLSEHE
Seq8  229  MTTDYGTHVRQLLQQGYQISLEYADARRYRTSSWQSGPTLTGQQESQVMAAIAQLLKEHE
           * **  ** ***  ***  * ** ** ******    *  *  **  *       * ***

Seq5   71  GEYVRLLGIDTNTRSRVFEALIQRP-DGSVPESLGSQPVAVASGGGRQSSYASVSGNLSA
Seq8  289  GEYVRLIGVDPKAKRRVFEEIIQRPGQAAVASSSSSRPSATVN--------ASPVGSLDA
           ****** * *    ****  ****     * *            *        **    * **  * *
```

-continued

```
Seq5  130  EVVNKVRNLLAQGYRIGTEHADKRRFRTSSWQSCAPIQSSNERQVLAELENCLSEHEGEY
Seq8  341  AVVAQVRQLLQQGYQIGTEHADARRYRTSSWTSCAPIQSKQEPEVLAALEACLQEHAGEY
           **  ** *** ******* **  ***** *******   *   *** ** ** ** ***

Seq5  190  VRLLGIDTASRSRVFEALIQDPQGPVGSAKAAAAPVSSATPSSHSYTSNGSSSSDVAGQV
Seq8  401  VRLIGIDQKQKRRVLEQIIQRPQGPVAIAPKTPTPVATSHASVSSGGNDTLLSADLVNQI
           *** ***        ** * ** *****  *       **      * *    **   *

Seq5  250  RGLLAQGYRISAEVADKRRFQTSSWQSLPALSGQSEATVLPALESILQEHKGKYVRLIGI
Seq8  461  QDLLRQGCQVITEYADQRRFRTSSWQSGIKITSAQQ---INDLRSFLAEHQRDYIRLVGV
            * **   *    * **  ** ****** *  *   ***     * *  ** *  ** **   *

Seq5  310  DPAARRRVAELLIQKP
Seq8  518  NPQAKQRVLETIIHRP
           *  * ** ** * *
```

This related protein from *Thermosynechococcus elongatus* BP-J has a sequence that is available from the National Center for Biotechnology Information database (see website at ncbi.nlm.nih.gov) with accession number NP_681734.1 (GI:22298487) and with the sequence shown below (SEQ ID NO:8).

```
  1  MAVQSYAAPP TPWSRDLAEP EIAPTAYVHS FSNLIGDVRI
 41  KDYVHIAPGT SIRADEGTPF HIGSRTNIQD GVVIHGLQQG
 81  RVIGDDGQEY SVWIGDNVSI THMALIHGPA YIGDCFIGF
121  RSTVFNARVG AGCVVMMHVL IQDVEIPPGK YVPSGMVITT
161  QQQADRLPNV EESDIHFAQH VVGINEALLS GYQCAENIAC
201  IAPIRNELQR QEDPPTLHVE MLTGEKNTMT TDYGTHVRQL
241  LQQGYQISLE YADARRYRTS SWQSGPTLTG QQESQVMAAI
281  AQLLKEHEGE YVRLIGVDPK AKRRVFEEii QRPGQAAVAS
321  SSSSRPSATV NASPVGSLDA AVVAQVRQLL QQGYQIGTEH
361  ADARRYRTSS WTSCAPIQSK QEPEVLAALE ACLQEHAGEY
401  VRLIGIDQKQ KRRVLEQIIQ RPQGPVAIAP KTPTPVATSH
441  ASVSSGGNDT LLSADLVNQI QDLLROGCQV ITEYADQRRF
481  RTSSWQSGIK ITSAQQINDL RSFLAEHQRD YIRLVGVNPQ
521  AKQRVLETII HRPNGKAASN GNSTRGQGFT PRPTASSQGS
561  PSTHSLSQEV IEQVRQLLQQ GYTLGLEHVD ARRYRTNSWQ
601  SGPRIEAKNL NEALAAIQAC LQEYSGEYVR LIGINPAGKQ
641  RVAEILLQQA AK
```

The short form CcmM portion of this *Thermosynechococcus elongatus* BP-1 related protein has four SSLDS and is shown below as SEQ ID NO:9.

```
201                                              THVRQL
241  LQQGYQISLE YADARRYRTS SWQSGPTLTG QQESQVMAAI
281  AQLLKEHEGE YVRLIGVDPK AKRRVFEEII QRPGQAAVAS
321  SSSSRPSATV NASPVGSLDA AVVAQVRQLL QQGYQIGTEH
361  ADARRYRTSS WTSCAPIQSK QEPEVLAALE ACLQEHAGEY
401  VRLIGIDQKQ KRRVLEQIIQ RPQGPVAIAP KTPTPVATSH
441  ASVSSGGNDT LLSADLVNQI QDLLRQGCQV ITEYADQRRF
481  RTSSWQSGIK ITSAQQINDL RSFLAEHQRD YIRLVGVNPQ
521  AKQRVLETII HRPNGKAASN GNSTRGQGFT PRPTASSQGS
561  PSTHSLSQEV IEQVRQLLQQ GYTLGLEHVD ARRYRTNSWQ
601  SGPRIEAKNL NEALAAIQAC LQEYSGEYVR LIGINPAGKQ
641  RVAEILLQQA AK
```

Some short forms of CcmM can have a few amino acids missing from the N-terminus or the C-terminus of the M35 protein. In addition, the N-terminus of the short form protein can have a methionine.

A related short form CcmM protein from *Trichormus azollae* has a sequence has at least 52% sequence identity to SEQ ID NO:5, as illustrated below.

```
51.1% identity in 321 residues overlap; Score: 798.0; Gap frequency: 1.9%
Seq5    10  RLSSEVITQVRSLLNQGYRIGTEHADKRRFRTSSWQPCAPIQSTNERQVLSELENCLSEH
Seq10  233  KLGAEIVDQVRYLLNQGYKIGTEHVDQRRFRTGSWQSCQPIETRSLGEAITALESCLIDH
            *  *  *** ****** * ***** * *** ** *****    *       * **   ** ** *

Seq5    70  EGEYVRLLGIDTNTRSRVFEALIQRPDGSVPESLGSQPVAVAS----GGGRQSSYASVSG
Seq10  293  SGEYVRLFGID-NGRKRVLETIIQRPDGVVATSSSFKTPAASYSSYNGNGNSNGAVASG
            ****** ***  *  ** * ******  *   *     *         *  *  *  **

Seq5   126  NLSAEVVNKVRNLLAQGYRIGTEHADKRRFRTSSWQSCAPIQSSNERQVLAELENCLSEH
Seq10  352  SLSAETVNQIRQLLANGYKIGTEHVDQRRFRTSSWQSCNPIEATSANDVVAALEECMTSH
            ****  * ***  ** ** ***** * **********  ***       * *** ** * *

Seq5   186  EGEYVRLLGIDTASRSRVFEALIQDPQGPVGSARAAAAPVSSATPSSHSYTSNGSS-SSD
Seq10  412  QGEYVRLIGIDSKAKRRVLEAIIQRPNGQVVSSGSAKTSGTLYSGATASATATSTRLSTE
             ****** ***    * ** *  **  *  * *   *  *         *    *     *
```

```
Seq5    245   VAGQVRGLLAQGYRISAEVADKRRFQTSSWQSLPALSGQSEATVLPALESILQEHKGKYV
Seq10   472   VVDQLKQLLTGGFKISVEHVDQRRFRTGSWVSCGQIQATSERDVLAALEAVISEYAGEYV
               *  *  **  *  ** *  * *** *  ** *      ** ** ***   *  * **

Seq5    305   RLIGIDPAARRRVAELLIQKP
Seq10   532   RLIGIDPVAKRRVLEAIIQRP
              ******* * *** *  ** *
```

This short form CcmM related protein from *Trichormus azollae* has a sequence that is available from the National Center for Biotechnology Information database (see website at ncbi.nlm.nih.gov) with accession number WP_013190978.1 (GI:502956002), and with the sequence shown below (SEQ ID NO:10).

```
  1   MVVRSTAAPP TPWSRSLAEP DIHQTAFVHS SCNLIGDVHL
 41   GQNVIIAPGT SIRADEGTPF FIGENTNIQD GVVIHGLEQG
 81   RVIGDDGKNY SVWVGKDASI THMALIHGPA YVGESCFIGF
121   RSIVENARVG AGCIVMMHAL IQDVEIPPGK YVASGSIITM
161   QQQADRLPDV QAQDQQFAHH VVGINQALRA GYRCVEDIKC
201   IAPIRDELNL SGDRSYTSII VDELERSSEV ASKLGAEIVD
241   QVRYLLNQGY KIGTEHVDQR RFRTGSWQSC QPIETRSLGE
281   AITALESCLI DHSGEYVRLF GIDNGRKRVL ETIIQRPDGV
321   VATSTSSFKT PAASYSSYNG NGNSNGAVAS GSLSAETVNQ
361   IRQLLANGYK IGTEHVDQRR FRTGSWQSCN PIEATSANDV
401   VAALEECMTS HQGEYVRLIG IDSKAKRRVL EAIIQRPNGQ
441   VVSSGSAKTS GTLYSGATAS ATATSTRLST EVVDQLKQLL
481   TGGFKISVEH VDQRRFRTGS WVSCGQIQAT SERDVLAALE
521   AVISEYAGEY VRLIGIDPVA KRRVLEAIIQ RP
```

The short form portion of this *Trichormus azollae* related protein contains three SSLDs and is shown below as SEQ ID NO:11.

```
233                                    V ASKLGAEIVD
241   QVRYLLNQGY KIGTEHVDQR RFRTGSWQSC QPIETRSLGE
281   AITALESCLI DHSGEYVRLE GIDNGRKRVL ETIIQRPDGV
321   VATSTSFKT PAASYSSYNG NGNSNGAVAS GSLSAETVNQ
361   IRQLLANGYK IGTEHVDQRR FRTGSWQSCN PIEATSANDV
401   VAALEECMTS HQGEYVRLIG IDSKAKRRVL EAIIQRPNGQ
441   VVSSGSAKTS GTLYSGATAS ATATSTRLST EVVDQLKQLL
481   TGGFKISVEH VDQRRFRTGS WVSCGQIQAT SERDVLAALE
521   AVISEYAGEY VRLIGIDPVA KRRVLEAIIQ RP
```

Some short forms of CcmM can have a few amino acids missing from the N-terminus or the C-terminus of the protein. In addition, the N-terminus of the short form CcmM protein can have a methionine.

CcmN Protein—Encapsulation Peptide (EP)

CcmN contains multiple hexapeptide-repeats and, at its C-terminus, an encapsulation peptide (EP), which is a short α-helical segment linked to the hexapeptide-repeat domains by a flexible linker sequence (Kinney et al., 2012). In general, encapsulation peptides have poorly conserved sequences but are amphipathic in nature (Aussignargues et al., 2015) A schematic diagram of the CcmN protein is shown in FIG. 1A.

An amino acid sequence for a *Synechococcus elongatus* PCC 7942 carbon dioxide concentrating mechanism protein (CcmN: Synpcc7942_1424) is available as accession number ABB57454 (SEQ ID NO:12).

```
  1   MHLPPLEPPI SDRYFASGEV TIAADVVIAP GVLLIAEADS
 41   RIEIASGVCI GLGSVIHARG GAIIIQAGAL LAAGVLIVGQ
 81   SIVGRQACLG ASTTLVNTSI EAGGVTAPGS LLSAETPPTI
121   ATVSSSEPAG RSPQSSAIAH PTKVYGKEQF LRMRQSMFPD
161   R
```

As illustrated herein, SSLDs domains are fused with an encapsulation peptide from a CcmN protein. Such an encapsulation peptide can have the following sequence (SEQ ID NO:13).

```
  1          VYGKEQFLRM RQSMFPDR
```

A related CcmN encapsulation peptide is available from *Prochlorothrix hollandica* that has at least 65% sequence identity to SEQ ID NO:13, as illustrated below.

| Score | Expect | Identities | Positives | Gaps |
|---|---|---|---|---|
| 30.8 bits(65) | 0.32 | 11/17(65%) | 13/17(76%) | 0/17(0%) |

```
Seq 13   VYGKEQFLRMRQSMFPD      17
Seq 14   VYGRDYFLQMRFSLFPD     414
         ***  **  ** * ***
```

This *Prochlorothrix hollandica* related encapsulation peptide has the following sequence: VYGRDYFLQMRFSLFPD (SEQ ID NO:14).

A related CcmN encapsulation peptide is available from *Halothece* sp. PCC 7418 (Cai et al. 2016) that has at least 27% sequence identity to SEQ ID NO:13, as illustrated below.

```
Seq13    VYGKEQFLRMRQSMFPDR-------------------------   18
Seq15    IYGQTHIERLMVTLFPHKEKFKKKTNDWFLVLGSLLFDDFPNNE   44
         :**: :: *:   ::**.:
```

The *Halothece* sp. PCC 7418 related encapsulation peptide has the following sequence: IYGQTHIERLMVTLFPHKEKFKKKTNDWFLVLGSLLFDDFPNNE (SEQ ID NO:15).

A related CcmN encapsulation peptide is available from *Moorea producens* that has at least 56% sequence identity to SEQ ID NO:13, as illustrated below.

| Score | Expect | Identities | Positives | Gaps |
|---|---|---|---|---|
| 28.2 bits(59) | 2.6 | 10/18(56%) | 12/18(66%) | 4/18(22%) |

```
Seq13           EQFLR-MRQSM---FPDR        18
Seq16    606    EQFFRRMRQSLNRAFSER       623
                *** * ****    *  *
```

The *Moorea producens* related encapsulation peptide has the following sequence: EQFFRRMRQSLNRAFSER (SEQ ID NO:16).

CcaA Carbonate Dehydratase (Carbonic Anhydrase)

While the CcmM and CcmN are typically conserved and are needed for native carboxysome formation (Long et al., 2010; Kinney et al., 2012), CcaA deletion mutant cell lines can still form carboxysomes (So et al., 2002b). Such CcaA deletion mutant cells exhibit a high carbon dioxide-requiring (hcr) phenotype. The CcaA genes encode carbonic anhydrase, also called carbonate dehydratase. A schematic diagram of the carbonate dehydratase, CcaA, protein is shown in FIG. 1A.

An amino acid sequence for a *Synechococcus elongatus* PCC 7942 carbonate dehydratase (CcaA; Synpcc7942_1447; 30185 daltons) is available as accession number ABB57477.1 (see website at uniprot.org/uniprot/P27134)(SEQ ID NO:17).

```
  1   MRKLIEGLRH FRTSYYPSHR DLFEQFAKGQ HPRVLFITCS

41   DSRIDPNLIT QSGMGELFVI RNAGNLIPPF GAANGGEGAS

81   IEYAIAALNI EHVVVCGHSH CGAMKGLLKL NQLQEDMPLV

121   YDWLQHAQAT RRLVLDNYSG YETDDLVEIL VAENVLTQIE

161   NLKTYPIVRS RLFQGKLQIF GWIYEVESGE VLQISRTSSD

201   DTGIDECPVR LPGSQEKAIL GRCVVPLTEE VAVAPPEPEP

241   VIAAVAAPPA NYSSRGWLAP EQQQRIYRGN AS
```

A related CcaA carbonate dehydratase is available from *Synechococcus elongatus* that has at least 99% sequence identity to SEQ ID NO:17, as illustrated below.

```
99.6% identity in 272 residues overlap; Score: 1415.0; Gap frequency: 0.0%
Seq17    1   MRKLIEGLRHFRTSYYPSHRDLFEQFAKGQHPRVLFITCSDSRIDPNLITQSGMGELFVI
Seq18    1   MRKLIEGLRHFRTSYYPSHRDLFEQFAKGQHPRVLFITCSDSRIDPNLITQSGMGELFVI
             ************************************************************

Seq17   61   RNAGNLIPPFGAANGGEGASIEYAIAALNIEHVVVCGHSHCGAMKGLLKLNQLQEDMPLV
Seq18   61   RNAGNLIPPFGAANGGEGASIEYAIAALNIEHVVVCGHSHCGAMKGLLKLNQLQEDMPLV
             ************************************************************

Seq17  121   YDWLQHAQATRRLVLDNYSGYETDDLVEILVAENVLTQIENLKTYPIVRSRLFQGKLQIE
Seq18  121   YDWLQHAQATRRLVLDNYSGYETDDLVEFLVAENVLTQIENLKTYPIVRSRLFQGKLQIE
             **************************** *******************************

Seq17  181   GWIYEVESGEVLQISRTSSDDTGIDECPVRLPGSQEKAILGRCVVPLTEEVAVAPPEPEP
Seq18  181   GWIYEVESGEVLQISRTSSDDTGIDECPVRLPGSQEKAILGRCVVPLTEEVAVAPPEPEP
             ************************************************************

Seq17  241   VIAAVAAPPANYSSRGWLAPEQQQRIYRGNAS
Seq18  241   VIAAVAAPPANYSSRGWLAPEQQQRIYRGNAS
             ********************************
```

This CcaA related protein from *Synechococcus elongatus* has a sequence that is available from the National Center for Biotechnology Information database (see website at ncbi.nlm.nih.gov) with accession number WP_011242423.1 (GI:499561640), and with the sequence shown below (SEQ ID NO:18).

```
  1  MRKLIEGLRH FRTSYYPSHR DLFEQFAKGQ HPRVLFITCS
 41  DSRIDPNLIT QSGMGELFVI RNAGNLIPPF GAANGGEGAS
 81  IEYAIAALNI EHVVVCGHSH CGAMKGLLKL NQLQEDMPLV
121  YDWLQHAQAT RRLVLDNYSG YETDDLVEFL VAENVLTQIE
161  NLKTYPIVRS RLFQGKLQIF GWIYEVESGE VLQISRTSSD
201  DTGIDECPVR LPGSQEKAIL GRCVVPLTEE VAVAPPEPEP
241  VIAAVAAPPA NYSSRGWLAP EQQQRIYRGN AS
```

A related CcaA carbonate dehydratase is available from *Geminocystis herdnanii* that has at least 55% sequence identity to SEQ ID NO:17, as illustrated below.

```
58.3% identity in 278 residues overlap; Score: 779.0; Gap frequency: 2.9%
Seq17    1  MRKLIEGLRHFRTSYYPSHRDLFEQFAKGQHPRVLFITCSDSRIDPNLITQSGMGELFVI
Seq19    1  MKKIIEGLHRFQAGYFESHRDLFEQLSHGQHPRILFITCSDSRIDPNLITQANVGELFVI
            * * ****  *   *  ********  ***** ******************  ******

Seq17   61  RNAGNLIPPFGAANGGEGASIEYAIAALNIEHVVVCGHSHCGAMKGLLKLNQLQEDMPLV
Seq19   61  RNAGNIIPPFGATNGGEGASIEYAITALDIEQVIVCGHSHCGAMKGLLKMSKLADKMPLV
            ***** ****** ************ ** ** * *************  *    ****

Seq17  121  YDWLQHAQATRRLVLDNYSGYETDDLVEILVAENVLTQIENLKTYPIVRSRLFOGKLQIF
Seq19  121  YEWLKQAEATRRLIIDNYSHLEGEELLQITVAENVLTQLENLNTYPIVRSRLHQGRLSLH
            * **  * *****  ****      *    * ********  ***  *********  * *

Seq17  181  GWIYEVESGEVLQISRTSSDDTGID------ECPVRLPGSQEKAILGRCVVPLTEEVAVA
Seq19  181  GWIYGIETGEVLTYDPKVHDFVNLESRTDNSEYIYNLHPSCSVAKSMFYGIPDENDDRVQ
            ****  * ****         *          *   *       *        *

Seq17  235  PPEPEPVIAAVAAPPANYSSR--GWLAPEQQQRIYRGN
Seq19  241  PSEPIPQTINPNLPRSRSGAARSNRLSPEQEQRIYRGS
            * ** *      *             * *** ******
```

This CcaA related protein from *Geminocystis herdmanii* has a sequence that is available from the National Center for Biotechnology Information database (see website at ncbi.nlm.nih.gov) with accession number WP_017295030.1 (GI:515864402), and with the sequence shown below (SEQ ID NO:19).

```
  1  MKKIIEGLHR FQAGYFESHR DLFEQLSHGQ HPRILFTTCS
 41  DSRIDPNLIT QANVGELFVI RNAGNIIPPF GATNGGEGAS
 81  IEYAITALDI EQVIVCGHSH CGAMKGLLKM SKLADKMPLV
121  YEWLKQAEAT RRLIIDNYSH LEGEELLQIT VAENVLTQLE
161  NLNTYPIVRS RLHQGRLSLH GWIYGIETGE VLTYDPKVHD
201  FVNLESRTDN SEYIYNLHPS CSVAKSMFYG IPDENDDKVQ
241  PSEPIPQTIN PNLPRSRSGA ARSNRLSPEQ EQRIYRGST
```

A related CcaA carbonate dehydratase is available from *Aliterella atlantica* that has at least 74% sequence identity to SEQ ID NO:17, as illustrated below.

```
57.2% identity in 271 residues overlap; Score: 786.0; Gap frequency: 0.4%
Seq17    1  MRKLIEGLRHFRTSYYPSHRDLFEQFAKGQHPRVLFITCSDSRIDPNLITQSGMGELFVI
Seq20    1  MRKLIKGLRAFKDNYYSNHLELFEKLTHAQKPRVLFITCSDSRIDPNLITQAAVGELFVI
            ***** *** *  **  *  *    * *  *********************  ******

Seq17   61  RNAGNLIPPFGAANGGEGASIEYAIAALNIEHVVVCGHSHCGAMKGLLKLNQLQEDMPLV
Seq20   61  RNAGNIIPPFGATNGGEGATVEYAVHALGIEQIVVCGHSHCGAMKGLLKLNKLQQDMPLV
            ***** ****** ******  ***  **  ** ***************** ** *****

Seq17  121  YDWLQHAQATRRLVLDNYSGYETDDLVEILVAENVLTQIENLKTYPIVRSRLFQGKLQIE
Seq20  121  YNWLQYAESTRRLVQENYNSYSEEELVEIAVAENVLTQIENLKTYPVVRSKLYOGKLQIY
            * ***  *  ****    *     ****  *************** *** * *****
```

```
-continued
Seq17    181   GWIYEVESGEVLQISRTSSDDTGIDECPVRLPGSQE-KAILGRCVVPLTEEVAVAPPEPE
Seq20    181   AWIYHLETGEVLAYDPQSHAYVAPQSQLMNGDTTESIETRIANTSAPIVACEFPSRHKQR
               ***  * ****        *                               *

Seq17    240   PVIAAVAAPPANYSSRGWLAPEQQQRLIRGN
Seq20    241   QVAHNTANNDGDTLPDMWLSPQQAERIYRGS
                *     *         **  *   *****
```

This CcaA related protein from *Aliterella atlantica* has a sequence that is available from the National Center for Biotechnology Information database (see website at ncbi.nlm.nih.gov) with accession number WP_045053064.1 (GI:769918643), and with the sequence shown below (SEQ ID NO:20).

```
  1   MRKLIKGLRA   FKDNYYSNHL   ELFEKLTHAQ   KPRVLFITCS
 41   DSRIDPNLIT   QAAVGELFVI   RNAGNIIPPF   GATNGGEGAT
 81   VEYAVHALGI   EQIVVCGHSH   CGAMKGLLKL   NKLQQDMPLV
121   YNWLQYAEST   RRLVQENYNS   YSEEELVEIA   VAENVLTQIE
161   NLKTYPVVRS   KLYQGKLQIY   AWIYHLETGE   VLAYDPQSHA
201   YVAPQSQLMN   GDTTESIETR   IANTSAPIVA   CEFPSRHKQR
241   QVAHNTANND   GDTLPDMWLS   PQQAERIYRG   SNGNR
```

A related CcaA carbonate dehydratase is available from *Leptolyngbya boryana* that has at least 74% sequence identity to SEQ ID NO:17, as illustrated below.

```
74.5% identity in 192 residues overlap; Score: 794.0; Gap frequency: 0.0%
Seq17    1    MRKLIEGLRHFRTSYYPSHRDLFEQFAKGQHPRVLFITCSDSRIDPNLITQSGMGELFVI
Seq21    1    MKKLIQGHQQFWESYVPSHLDQLEELSHGQKPRVLFITCSDSRIDPNLITQAGIGELFVI
              * ***  *  *  ** ***  *       **********************  * ******

Seq17   61    RNAGNLIPPFGAANGGEGASIEYAIAALNIEHVVVCGHSHCGAMKGLLKLNQLQEDMPLV
Seq21   61    RNAGNIIPPFGAANGGEGAAVEYAIAALDIQQIIVCGHSHCGAMKGLLKLNKLQEDMPLV
              ***** *************   ******* *    *****************  *******

Seq17  121    YDWLQHAQATRRLVLDNYSGYETDDLVEILVAENVLTQIENLKTYPIVRSRLFQGKLQIE
Seq21  121    YDWLKHAEATRRLVKENYSQYSGEELLEITIAENVLTQIENLKTYPVVHSRLYQGKLEIY
              **** **  ****** *** *    *  ** ***************  ** ***  *** *

Seq17  181    GWIYEVESGEVL
Seq21  181    GWVYHIETGELL
              ** *  * ** *
```

This CcaA related protein from *Leptolyngbya boryana* has a sequence that is available from the National Center for Biotechnology Information database (see website at ncbi.nlm.nih.gov) with accession number WP_017285834.1 (GI:515855206), and with the sequence shown below (SEQ ID NO:21).

```
  1   MKKLIQGHQQ   FWESYVPSHL   DQLEELSHGQ   KPRVLFITCS
 41   DSRIDPNLIT   QAGIGELFVI   RNAGNIIPPF   GAANGGEGAA
 81   VEYAIAALDI   QQIIVCGHSH   CGAMKGLLKL   NKLQEDMPLV
121   YDWLKHAEAT   RRLVKENYSQ   YSGEELLEIT   IAENVLTQIE
161   NLKTYPVVHS   RLYQGKLEIY   GWVYHIETGE   LLAFDPETHA
201   YVPPQSQLSP   RELGAFYEKT   SAPPVACNLP   HKEDNGNGQL
241   RQPVTIRSQV   KSAEPVPQTE   VMPWLTAEQA   QRIYQGSKR
```

Many cyanobacteria lack CcaA (Zarzycki et al., 2013) and its function can be replaced by the γ-CA domain of CcmM (Peña 2010).

CcmC Chimeric Protein

A streamlined carboxysome core, referred to as CcmC, is described herein that combines segments of several carboxysome components into a single chimeric protein. CcmC contains scaffolding domains (the SSLDs that are involved in nucleating Rubisco), an enzymatic domain (carbonic anhydrase), and an encapsulating domain (the EP). FIG. 1B shows a schematic diagram of the chimeric protein. The following is an amino acid sequence for a CcmC gene (SEQ ID NO:22).

```
  1   MTVSAYNGQG   RLSSEVITQV   RSLLNQGYRI   GTEHADKRRF
 41   RTSSWQPCAP   IQSTNERQVL   SELENCLSEH   EGEYVRLLGI
 81   DTNTRSRVFE   ALIQRPDGSV   PESLGSQPVA   VASGGGRQSS
121   YASVSGNLSA   EVVNKVRNLL   AQGYRIGTEH   ADKRRFRTSS
```

```
-continued
161   WQSCAPIQSS   NERQVLAELE   NCLSEHEGEY   VRLLGIDTAS
201   RSRVFEALIQ   DPQGPVGSAK   AAAAPVSSAT   PSSHSYTSNG
241   SSSSDVAGQV   RGLLAQGYRI   SAEVADKRRF   QTSSWQSLPA
281   LSGQSEATVI   PALESILQEH   KGKYVRLIGI   DPAARRRVAE
321   LLIQKPGSRK   LIEGLRHFRT   SYYPSHRDLF   EQFAKGQHPR
361   VLFITCSDSR   IDPNLITQSG   MGELFVIRNA   GNLIPPFGAA
401   NGGEGASIEY   AIAALNIEHV   VVCGHSHCGA   MKGLLKLNQL
441   QEDMPLVYDW   LQHAQATRRL   VLDNYSGYET   DDLVEILVAE
481   NVLTQIENLK   TYPIVRSRLF   QGKLQIFGWI   YEVESGEVLQ
521   ISRTSSDDTG   IDECPVRLPG   SQEKAILGRC   VVPLTEEVAV
```

```
561  APPEPEPVIA AVAAPPANYS SRGWLGSGGS VYGKEQFLRM
601  RQSMFPDR
```

Note that amino acids 2-326 of the CcmC protein (with SEQ ID NO:22) are the same as the CcmM short form from *Synechococcus elongatus* PCC 7942 provided as SEQ ID NO:5. Similarly, amino acids 1-328 of the CcmC protein (with SEQ ID NO:22) are the same as amino acids 1-328 of the M35-EP protein with SEQ ID NO:37. The central amino acids 329-585 of the SEQ ID NO:38 CcmC protein correspond to amino acids 2-258 of the carbonate dehydratase (CcaA) with SEQ ID NO:71. Amino acids 591-608 of the SEQ ID NO:38 CcmC protein correspond to the encapsulation peptide (EP) from a CcmN protein, which has SEQ ID NO:13. Other M35, CcaA, and EP polypeptide segments can substitute for these M35. CcaA, and EP segments to form related CmcC proteins.

Such synthetic CcmC core proteins can support the assembly of functionally competent carboxysomes in cyanobacteria.

Such synthetic CcmC core proteins can have some sequence variation. For example, a CcmC core protein can have at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity sequence identity (or complementarity) with SEQ ID NO:22. Related CcmC proteins can have, for example, 60-99% sequence identity, or 70-99% sequence identity, or 80-99% sequence identity, or 90-95% sequence identity, or 90-99% sequence identity, or 95-97% sequence identity, or 95-98% sequence identity, or 97-99% sequence identity, or 95-99% sequence identity, or 95-100% sequence identity, or 96-100% sequence identity, or 97-100% sequence identity, or 100% sequence identity (or complementarity) with SEQ ID NO:22.

Expression of multiple genes has previously been deemed to be necessary to assemble a BMC core in heterologous systems. However, the construct described herein has a streamlined design that functions to fix carbon even though it is smaller, and consists of a single polypeptide that has small subunit-like domains (SSLDs), Encapsulation peptide (EP), and carbonic anhydrase domains.

The more compact CcmC core protein can accommodate domain components with a variety sequences related to those described herein. For example, a CcmC core protein can have SSLDs (small subunit-like domains), encapsulation peptide (EP), and carbonic anhydrase domains that have at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of the SEQ ID NOs described herein.

Previous attempts to engineer bacterial microcompartments have focused on associating heterologous proteins to shell proteins using encapsulation peptides (EPs). For example, through the addition of two different EPs to pyruvate decarboxylase and alcohol dehydrogenase, Lawrence et al. were able to repurpose a propanediol utilization (PDU) compartment for ethanol production (Lawrence et al., 2014). Lin et al. showed that the encapsulation peptide from CcmN targets yellow fluorescent protein into carboxysome-like structures formed in mutant tobacco (*Nicotiana benthamiana*) plants (Lin et al., 2014b).

In contrast to such previous studies the approach reported here focuses on assembling a multifunctional bacterial microcompartment core using a single polypeptide to nucleate assembly and provide key functions: CcmC nucleates Rubisco, supplies carbonic anhydrase activity, and recruits the shell. This approach allows the packaging of multiple protein domains within a shell using only a single encapsulation peptide (EP).

Shell Proteins

In some cases, it may be useful to express carboxysome shell protein(s) along with the CcmC chimeric core protein.

For example, a carbon dioxide concentrating mechanism protein CcmK and/or CcmL shell protein from *Synechococcus elongatus* PCC 7942 can be expressed along with the CcmC chimeric core protein. An example of a sequence for such a CcmK shell protein from *Synechococcus elongatus* PCC 7942 is provided below as SEQ ID NO:23 (see NCBI accession number (ABB56317.1; GI:81167977).

```
 1   MSQQAIGSLE TKGFPPILAA ADAMVKAGRI TIVSYMRAGS
41   ARFAVNIRGD VSEVKTAMDA GIEAAKNTPG GTLETWVIIP
81   RPHENVEAVF PIGFGPEVEO YRLSAEGTGS GRR
```

An example of a sequence for such a CcmL shell protein from *Synechococcus elongatus* PCC 7942 is provided below as SEQ ID NO:24 (see NCBI accession number (ABB57452.1; GI:81169112).

```
 1   MRIAKVRGTV VSTYKEPSLQ GVKFLVVQFL DEAGQALQEY
41   EVAADMVGAG VDEWVLISRG SQARHVRDCQ ERPVDAAVIA
81   IIDTVNVENR SVYDKREHS
```

Such shell proteins can have some sequence variation. For example, such shell proteins can have at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with SEQ ID NO:23 and/or SEQ ID NO:24.

Rubisco

In some cases, ribulose-1,5-bisphosphate carboxylase/oxygenase, abbreviated as Rubisco herein (also abbreviated as RuBPCase), can also be expressed with the chimeric core carboxysome CcmC protein. Rubisco is an enzyme that can be involved carbon fixation, to provide building blocks for energy-rich molecules such as glucose. Rubisco can catalyze the carboxylation of ribulose-1,5-bisphosphate, and may be one of the most abundant enzymes on Earth.

For example, a ribulose-1,5-bisphosphate carboxylase/oxygenase (Rubisco) protein can be expressed along with the CcmC chimeric core protein. An example of a sequence for such a Rubisco protein from *Synechococcus elongatus* PCC 7942 is provided below as SEQ ID NO:25 (see NCBI accession number (ABB57456.1; GI:81169116).

```
  1  MPKTQSAAGY KAGVKDYKLT YYTPDYTPKD TDLLAAFRFS
 41  PQPGVPADEA GAAIAAESST GTWTTVWTDL LTDMDRYKGK
 81  CYHIEPVQGE ENSYFAFIAY PLDLFEEGSV TNILTSIVGN
121  VFGFKAIRSL RLEDIRFPVA LVKTFQGPPH GIQVERDLLN
161  KYGRPMLGCT IKPKLGLSAK NYGRAVYECL RGGLDFTKDD
201  ENINSQPFQR WRDRFLFVAD AIHKSQAETG EIKGHYLNVI
241  APTCEEMMKR AEFAKELGMP IIMHDFLTAG FTANTTLAKW
281  CRDNGVLLHI HRAMHAVIDR QRNHGIHFRV LAKCLRLSGG
321  DHLHSGTVVG KLEGDKASTL GFVDLMREDH IEADRSRGVF
361  FTQDWASMPG VLPVASGGIH VWHMPALVEI FGDDSVLQFG
401  GGTLGHPWGN APGATANRVA LEACVQARNE GRDLYREGGD
441  ILREAGKWSP ELAAALDLWK EIKFEFETMD KL
```

Expression

The chimeric carboxysome core protein, shell protein(s), Rubisco protein(s), and combinations thereof can be expressed from an expression cassette or expression vector. An expression cassette can include a nucleic acid segment that encodes a chimeric carboxysome core protein, shell protein, or Rubisco protein operably linked to a promoter to drive expression. In some cases, such polypeptide(s) can be expressed using convenient vectors, or expression systems. The invention therefore provides expression cassettes or vectors useful for expressing one or more chimeric carboxysome core protein, shell protein. Rubisco protein.

For example, a nucleotide sequence that encodes the chimeric core carboxysome CcmC protein and that can be expressed in a variety of organisms, including *Synechococcus elongatus* PCC 7942, is shown below as SEQ ID NO:26.

```
   1  ATGACCGTGA GCGCTTATAA CGGCCAAGGC CGACTCAGTT
  41  CCGAAGTCAT CACCCAAGTC CGGAGTTTGC TGAACCAGGG
  81  CTATCGGATT GGGACGGAAC ATGCGGACAA GCGCCGCTTC
 121  CGGACTAGCT CTTGGCAGCC CTGCGCGCCC ATTCAAAGCA
 161  CGAACGAGCG CCAGGTCTTG AGCGAACTGG AAAATTGTCT
 201  GAGCGAACAC GAAGGTGAAT ACGTTCGCTT GCTCGGCATC
 241  GATACCAATA CTCGCAGCCG TGTTTTTGAA GCCCTGATTC
 281  AACGGCCCGA TGGTTCGGTT CCTGAATCGC TGGGGAGCCA
 321  ACCGGTGGCA GTCGCTTCCG GTGGTGGCCG TCAGAGCAGC
 361  TATGCCAGCG TCAGCGGCAA CCTCTCAGCA GAAGTGGTCA
 401  ATAAAGTCCG CAACCTCTTA GCCCAAGGCT ATCGGATTGG
 441  GACGGAACAT GCAGACAAGC GCCGCTTTCG GACTAGCTCT
 481  TGGCAGTCCT GCGCACCGAT TCAAAGTTCG AATGAGCGCC
 521  AGGTTCTGGC TGAACTGGAA AACTGTCTGA GCGAGCACGA
 561  AGGTGAGTAC GTTCGCCTGC TGGGCATCGA CACTGCTAGC
 601  CGCAGTCGTG TTTTTGAAGC CCTGATCCAA GATCCCCAAG
 641  GACCGGTGGG TTCCGCCAAA GCGGCCGCCG CACCTGTGAG
 681  TTCGGCAACG CCCAGCAGCC ACAGCTACAC CTCAAATGGA
 721  TCGAGTTCGA GCGATGTCGC TGGACAGGTT CGGGGTCTGC
 761  TAGCCCAAGG CTACCGGATC AGTGCGGAAG TCGCCGATAA
 801  GCGTCGCTTC CAAACCAGCT CTTGGCAGAG TTTGCCGGCT
 841  CTGAGTGGCC AGAGCGAAGC AACTGTCTTG CCTGCTTTGG
 881  AGTCAATTCT GCAAGAGCAC AAGGGTAAGT ATGTGCGCCT
 921  GATTGGGATT GACCCTGCGG CTCGTCGTCG CGTGGCTGAA
 961  CTGTTGATTC AAAAGCCGGG ATCTCGCAAG CTCATCGAGG
1001  GGTTACGGCA TTTCCGTACG TCCTACTACC CGTCTCATCG
1041  GGACCTGTTC GAGCAGTTTG CCAAAGGTCA GCACCCTCGA
1081  GTCCTGTTCA TTACCTGCTC AGACTCGCGC ATTGACCCTA
1121  ACCTCATTAC CCAGTCGGGC ATGGGTGAGC TGTTCGTCAT
1161  TCGCAACGCT GGCAATCTGA TCCCGCCCTT CGGTGCCGCC
1201  AACGGTGGTG AAGGGGCATC GATCGAATAC GCGATCGCAG
1241  CTTTGAACAT TGAGCATGTT GTGGTCTGCG GTCACTCGCA
1281  CTGCGGTGCG ATGAAAGGGC TGCTCAAGCT CAATCAGCTG
1321  CAAGAGGACA TGCCGCTGGT CTATGACTGG CTGCAGCATG
1361  CCCAAGCCAC CCGCCGCCTA GTCTTGGATA ACTACAGCGG
1401  TTATGAGACT GACGACTTGG TAGAGATTCT GGTCGCCGAG
1441  AATGTGCTGA CGCAGATCGA GAACCTTAAG ACCTACCCGA
1481  TCGTGCGATC GCGCCTTTTC CAAGGCAAGG TGCAGATTTT
1521  TGGCTGGATT TATGAAGTTG AAAGCGGCGA GGTCTTGCAG
1561  ATTAGCCGTA CCAGCAGTGA TGCACAGGC ATTGATGAAT
1601  GTCCAGTGCG TTTGCCCGGC AGCCAGGAGA AAGCCATTCT
1641  CGGTCGTTGT GTCGTCCCCC TGACCGAAGA AGTGGCCGTT
1681  GCTCCACCAG AGCCGGAGCC TGTGATCGCG GCTGTGGCGG
1721  CTCCACCCGC CAACTACTCC AGTCGCGGTT GGTTGGGATC
1761  TGGAGGCAGT GTCTACGGCA AGGAACAGTT TTTGCGGATG
1801  CGCCAGAGCA TGTTCCCCGA TCGCTAA
```

Another nucleotide sequence is provided below that encodes the chimeric core carboxysome CcmC protein and that has been codon-optimized for expression in *Escherichia coli* (SEQ ID NO:27).

```
   1  ATGACCGTTT CCGCGTACAA CGGACAGGGC AGACTTTCGA
  41  GTGAAGTTAT AACCCAGGTC CGGTCTTTGT TGAACCAAGG
  81  CTATCGCATC GGGACCGAAC ATGCCGATAA GCGCCGTTTC
 121  CGGACCTCAA GTTGGCAACC GTGCGCGCCC ATCCAGTCAA
```

```
161  CCAATGAACG CCAGGTATTG TCTGAATTAG AGAATTGCTT
201  ATCGGAACAC GAAGGAGAAT ACGTTCGCTT GTTAGGAATT
241  GACACTAACA CAAGAAGTCG GGTTTTCGAA GCACTGATCC
281  AGCGCCCGGA CGGGTCTGTT CCTGAATCTT TGGGCAGCCA
321  GCCAGTAGCA GTGGCTTCCG GAGGCGGAAG ACAATCGTCC
361  TATGCATCTG TTTCCGGCAA CTTGTCTGCT GAGGTTGTTA
401  ATAAGGTGCG CAACCTGCTT GCCCAGGGTT ACAGAATTGG
441  CACGGAGCAC GCCGATAAGC GCCGTTTTAG AACCAGCTCG
481  TGGCAGTCTT GTGCGCCGAT ACAGTCCTCG AATGAACGGC
521  AGGTGCTGGC AGAGTTAGAG AATTGCCTGA GTGAGCATGA
561  AGGAGAATAC GTCCGCCTTC TGGGCATTGA CACCGCTTCC
601  CGTTCGCGTG TTTTCGAAGC CCTTATTCAG GATCCGCAAG
641  GCCCCGTGGG TTCCGCCAAA GCTGCCGCAG CACCTGTATC
681  AAGTGCTACC CCTTCGTCCC ACAGTTATAC GTCGAACGGC
721  AGCTCATCAT CTGACGTGGC GGGCCAGGTT CGTGGGTTGT
761  TGGCTCAAGG GTATCGGATA TCGGCTGAGG TTGCGGATAA
801  ACGTCGGTTC CAAACATCGT CGTGGCAGTC CTTGCCTGCA
841  TTATCGGGTC AATCGGAAGC AACGGTCCTT CCTGCGCTGG
881  AGAGTATCCT TCAGGAGCAC AAGGGCAAGT ACGTCAGATT
921  GATAGGGATC GATCCGGCGG CGCGGAGACG GGTGGCAGAA
961  TTGCTTATCC AAAAACCCGG TTCGCGCAAG TTGATCGAAG
1001 GATTAAGAGA TTTTAGAACC TCATATTACC CGAGTCATAG
1041 AGATTTATTC GAGCAGTTTG CAAAGGGTCA ACACCCTAGA
1081 GTCCTGTTCA TCACTTGCTC GGATTCACGG ATCGATCCTA
1121 ATTTGATCAC GCAGTCTGGT ATGGGAGAGC TTTTCGTCAT
1161 CCGTAACGCA GGTAACCTGA TTCCACCTTT CGGCGCGGCA
1201 AATGGGGGTG AGGGTGCGTC CATTGAATAT GCCATCGCCG
1241 CATTGAATAT CGAACACGTA GTTGTATGTG GCCACTCGCA
1281 CTGTGGAGCG ATGAAGGGC TGCTGAAGCT TAACCAGCTG
1321 CAAGAAGACA TGCCCCTTGT TTACGATTGG TTGCAACACG
1361 CGCAGGCCAC GAGACGTCTG GTCCTTGACA ACTACAGCGG
1401 ATATGAAACG GACGACCTTG TCGAGATCCT GGTCGCCGAG
1441 AACGTATTGA CCCAAATAGA GAATCTGAAG ACCTACCCAA
1481 TTGTGCGCTC GCGCTTGTTC CAGGGTAAGT TACAAATTTT
1521 CGGTTGGATC TATGAAGTGG AAAGTGGAGA GGTCTTGCAA
1561 ATCTCACGTA CATCCTCGGA CGACACAGGA ATAGACGAGT
1601 GCCCCGTCCG TTTACCGGGA TCGCAAGAGA AGGCCATTTT
1641 AGGACGGTGC GTCGTGCCAC TGACAGAGGA AGTGGCTGTT
1681 GCCCCTCCAG AACCAGAGCC TGTCATTGCT GCGGTGGCCG
1721 CACCACCCGC GAATTACTCC AGTCGCGGTT GGCTGGGCTC
1761 TGGAGGCTCT GTCTACGGAA AGGAACAATT CCTTCGTATG
1801 CGGCAATCAA TGTTCCCGGA CCGCTAA
```

Another nucleotide sequence is provided below that encodes the chimeric core carboxysome CcmC protein and that has been codon-optimized for expression in *Nicotiana tabacum* (SEQ ID NO:28).

```
1    ATGACTGTGA GTGCATATAA TGGACAAGGT AGATTGAGTT
41   CTGAAGTGAT AACTCAAGTG CGTAGCCTTT TGAATCAAGG
81   ATACAGAATT GGGACCGAAC ACGCAGATAA AAGAAGGTTT
121  AGAACCAGTT CATGGCAGCC ATGCGCCCCC ATCCAGTCTA
161  CTAATGAAAG ACAAGTGCTT TCTGAGCTGG AAAACTGTCT
201  TAGTGAACAT GAAGGCGAGT ATGTGCGATT GCTGGGTATC
241  GATACTAACA CTCGTAGCCG TGTTTTTGAA GCTCTGATAC
281  AACGACCTGA CGGTAGTGTC CCCGAATCAC TGGGTAGCCA
321  GCCCGTAGCA GTAGCTAGCG GGGGCGGGCG ACAGTCCTCC
323  GCCCGTAGCA GTAGCTAGCG GGGGCGGGCG ACAGTCCTCC
361  TACGCCTCTG TTAGCGGCAA CCTCTCAGCC GAAGTAGTGA
401  ACAAAGTAAG AAACCTCCTC GCCCAGGGTT ACCGTATAGG
441  AACCGAGCAC GCAGACAAAC GAAGATTCAG GACTAGCAGC
481  TGGCAATCCT GCGCACCCAT ACAATCTTCC AACGAAAGAC
521  AGGTACTGGC AGAATTGGAA AACTGTCTTT CAGAACATGA
561  AGGCGAGTAC GTCCGTCTGC TGGGGATCGA CACAGCAAGC
601  AGAAGCCGAG TATTTGAAGC CCTCATTCAA GATCCACAGG
641  GGCCAGTAGG TAGTGCAAAG GCAGCTGCAG CTCCCGTTTC
681  ATCTGCTACT CCCAGCAGTC ACAGCTACAC TTCTAATGGG
721  TCTTCCAGTA GTGACGTCGC CGGACAGGTA AGAGGCCTGT
763  TGGCACAGGG TTACCGAATA TCTGCCGAAG TAGCTGATAA
801  AAGGCGATTC CAGACTTCAT CCTGGCAGTC CCTTCCTGCA
841  TTGTCTGGCC AATCTGAAGC CACTGTTCTT CCTGCACTTG
881  AATCCATTTT GCAGGAACAT AAAGGTAAGT ATGTTCGATT
921  GATCGGTATC GATCCAGCTG CACGTAGAAG GGTTGCAGAG
961  TTATTGATTC AGAAGCCAGG ATCTCGAAAA TTAATAGAGG
1001 GTTTACGACA TTTCAGAACT TCTTACTACC CTTCCCATCG
1041 TGACTTATTC GAGCAATTTG CAAAAGGCCA ACATCCCAGA
1081 GTCTTGTTTA TCACTTGTTC AGACTCTCGA ATAGACCCCA
1121 ATCTCATAAC ACAGTCTGGA ATGGGCGAGC TTTTCGTGAT
1161 AGGTAACGCC GGCAACCTCA TTCCTCCCTT TGGTGCAGCT
1201 AACGGGGGCG AGGGGGCTTC AATAGAGTAC GCTATCGCTG
1241 CCCTCAATAT CGAACACGTC GTAGTATGCG GACATTCACA
1281 TTGCGGGGCC ATGAAGGGAC TGTTGAAGCT GAATCAACTC
1321 CAAGAGGACA TGCCCCTGGT CTATGATTGG TTGCAGCACG
```

-continued

```
1361 CCCAAGCTAC TAGGAGATTA GTTTTAGACA ACTACTCTGG
1401 CTATGAAACT GATGACCTGG TAGAAATACT GGTCGCAGAA
1441 AACGTATTAA CTCAGATAGA AAATTTAAAG ACTTATCCCA
1481 TAGTCCGTAG CCGATTGTTC CAAGGAAAAT TGCAAATATT
1521 CGGGTGGATC TATGAGGTTG AGTCCGGAGA GGTCTTGCAG
1561 ATAAGTCGAA CTAGCTCCGA CGACACAGGG ATAGACGAAT
1601 GCCCAGTCAG GTTGCCCGGG TCTCAAGAGA AAGCTATCTT
1641 GGGGAGGTGT GTCGTTCCTT TAACCGAGGA AGTTGCTGTC
1681 GGCCCCCCTG AGCCTGAACC TGTGATAGCT GCCGTAGCCG
1721 CACCCCCTGC CAACTATTCA TCACGAGGCT GGCTTGGCTC
1761 AGGGGGCTCA GTTTATGGGA AGGAACAATT CCTGAGGATG
1801 AGACAGTCAA TGTTCCCCGA TAGATAA
```

Another nucleotide sequence is provided below that encodes the chimeric core carboxysome CcmC protein and that has been codon-optimized for expression in *Chlamydomonas reinhardtii* (SEQ ID NO:29).

```
   1 ATGACGGTGT CGGCTTACAA CGGCCAGGGC CGCCTCTCGT
  41 CCGAGGTCAT TACGCAGGTC CGGAGCCTCC TGAACCAGGG
  81 GTACCGGATT GGTACCGAGC ATGCCGACAA GCGGCGCTTT
 121 CGGACGTCGT CCTGGCAGCC CTGCGCGCCC ATTCAGAGCA
 161 CCAACGAGCG GCAGGTCCTC TCCGAGCTGG AGAACTGCCT
 201 CAGCGAGCAT GAGGGGGAGT ACGTCCGCCT GCTGGGGATC
 241 GATACGAACA CGCGCTCCCG GGTCTTCGAG GCTCTCATCC
 281 AGCGCCCTGA CGGCTCGGTG CCTGAGAGCC TCGGCTCGCA
 321 GCCTGTGGCC GTGGCGAGCG GCGGTGGGCG GCAGTCCAGC
 361 TACGCCAGCG TGTCGGGTAA CCTCTCCGCC GAGGTCGTCA
 401 ACAAGGTGCG GAACCTCCTG GCCCAGGGCT ACCGGATCGG
 441 TACCGAGCAC GCCGACAAGC GCCGCTTTCG CACGAGCTCG
 481 TGGCAGAGCT GCGCCCCCAT TCAGTCGAGC AACGAGCGGC
 521 AGGTGCTCGC TGAGCTGGAG AACTGCCTCT CCGAGCATGA
 561 GGGCGAGTAC GTGCGGCTGC TCGGGATTGA TACGGCCTCG
 601 CGGTCGCGCG TGTTTGAGGC GCTGATCCAG GACCCCCAGG
 641 GTCCTGTCGG TTCGGCTAAG GCTGCGGCTG CCCCTGTGTC
 681 CTCGGCCACC CCCAGCTCGC ATTCGTACAC CTCGAACGGC
 721 TCCTCGTCGT CCGATGTGGC GGGTCAGGTG CGCGGGCTCC
 761 TCGCTCAGGG CTACCGCATC AGCGCTGAGG TCGCCGATAA
 801 GCGGCGGTTT CAGACGAGCT CGTGGCAGTC CCTCCCGGCG
 841 CTCTCGGGTC AGAGCGAGGC CACCGTCCTC CCTGCTCTCG
 881 AGTCGATTCT CCAGGAGCAT AAGGGGAAGT ACGTCCGGCT
 921 CATCGGGATT GACCCGGCTG CTCGGCGCCG CGTGGCGGAG
 961 CTGCTGATTC AGAAGCCTGG CAGCCGGAAG CTCATCGAGG
1001 GGCTCCGCCA TTTCCGGACG TCCTACTACC CCTCCCACCG
1041 CGATCTCTTC GAGCAGTTTG CCAAGGGGCA GCACCCGCGG
1081 GTCCTGTTCA TTACGTGCTC CGATAGCCGC ATTGACCCGA
1121 ACCTCATCAC GCAGAGCGGT ATGGGTGAGC TCTTTGTGAT
1161 TCGCAACGCT GGTAACCTCA TTCCTCCCTT TGGGGCGGCG
1201 AACGGCGGCG AGGGTGCGTC GATTGAGTAC GCTATCGCCG
1241 CCCTCAACAT TGAGCATGTC GTGGTGTGCG GTCATAGCCA
1281 TTGCGGCGCG ATGAAGGGCC TCCTCAAGCT GAACCAGCTG
1321 CAGGAGGACA TGCCTCTGGT GTACGACTGG CTGCAGCATG
1361 CTCAGGCTAC GCGGCGCCTC GTCCTGGACA ACTACTCGGG
1401 CTACGAGACC GATGACCTCG TCGAGATCCT CGTGGCGGAG
1441 AACGTGCTGA CCCAGATTGA GAACCTCAAG ACGTACCCCA
1481 TCGTGCGCTC GCGCCTCTTC CAGGGCAAGC TGCAGATCTT
1521 CGGTTGGATT TACGAGGTGG AGTCGGGGGA GGTCCTGCAG
1561 ATCAGCCGGA CGAGCTCCGA CGACACCGGG ATCGATGAGT
1601 GCCCTGTCCG CCTGCCGGGC TCGCAGGAGA AGGCCATTCT
1641 GGGTCGGTGC GTGGTCCCCC TGACGGAGGA GGTGGCTGTG
1681 GCTCCTCCCG AGCCTGAGCC CGTCATTGCG GCGGTCGCCG
1721 CCCCTCCGGC TAACTACTCC AGCCGGGGGT GGCTCGGCTC
1761 CGGGGGGAGC GTCTACGGCA AGGAGCAGTT TCTGCGCATG
1801 CGGCAGTCGA TGTTCCCGGA TCGCTAA
```

The expression cassettes or vectors can include a promoter that is operably linked to a nucleic acid segment that encodes the chimeric core carboxysome CcmC protein. A promoter is a nucleotide sequence that controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell.

Any promoter able to direct transcription of an encoded peptide or polypeptide may be used. Accordingly, many promoters may be included within the expression cassette. Some useful promoters include constitutive promoters, inducible promoters, regulated promoters, cell specific promoters, viral promoters, and synthetic promoters. Particularly useful promoters are inducible promoters, especially those induced by inexpensive signals, or promoters that are auto-inducing under certain environmental conditions (e.g. a relatively dense cyanobacterial population).

For expression of one or more chimeric carboxysome core protein, shell protein, Rubisco protein, or combinations thereof in a host cell, one or more expression cassette can be used that has a nucleic acid segment encoding such protein(s) and a promoter operably linked thereto. Such a promoter can be any DNA sequence capable of binding a RNA polymerase and initiating the downstream (3") transcription of a coding sequence into mRNA. A promoter has a transcription initiation region that is usually placed proximal to the 5' end of the coding sequence. This transcription initiation region usually includes an RNA polymerase binding site and a transcription initiation site. A second domain called an operator may be present and overlap an adjacent RNA polymerase binding site at which RNA synthesis begins. The operator permits negatively regulated (inducible) transcription, as a gene repressor protein may bind the operator and thereby inhibit transcription of a specific gene.

Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* (Raibaud et al., *Ann. Rev. Genet.*, 18:173 (1984)). Regulated expression may therefore be positive or negative, thereby either enhancing or reducing transcription.

Other examples of promoters that can be employed include promoters of sugar metabolizing enzymes, such as galactose, lactose (lac) (Chang et al., *Nature*, 198:1056 (1977), and maltose. Additional examples include promoter sequences derived from biosynthetic enzymes such as tryptophan (Trp) (Goeddel et al., *Nuc. Acids Res.*, 8:4057 (1980); Yelverton et al., *Nuc. Acids Res.*, 9:731 (1981); U.S. Pat. No. 4,738,921; and EPO Publ. Nos. 036 776 and 121 775). The β-lactamase (bla) promoter system (Weissmann, "The cloning of interferon and other mistakes", in: Interferon 3 (ed. I. Gresser), 1981), and bacteriophage lambda $P_L$ (Shimatake et al., *Nature*, 292:128 (1981)) and T5 (U.S. Pat. No. 4,689,406) promoter systems also provide useful promoter sequences. Another example is the *Chlorella* virus promoter (U.S. Pat. No. 6,316,224).

Synthetic promoters that do not occur in nature also function as promoters in host cells. For example, transcription activation sequences of a promoter may be joined with the operon sequences of another promoter, creating a synthetic hybrid promoter (U.S. Pat. No. 4,551,433). For example, the tac promoter is a hybrid trp-lac promoter comprised of both trp promoter and lac operon sequences that is regulated by the lac repressor (Amann et al., Gene, 25:167 (1983); de Boer et al., Proc. Natl. Acad. Sci. USA, 80:21 (1983)). Furthermore, a promoter can include naturally occurring promoters of non-bacterial origin that have the ability to bind RNA polymerase and initiate transcription in cyanobacteria or other types of host cells. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., *J. Mol. Biol.*, 189:113 (1986); Tabor et al., *Proc. Natl. Acad. Sci. USA*, 82:1074 (1985)). In addition, a hybrid promoter can also be comprised of a bacteriophage promoter and an *E. coli* operator region (EPO Publ. No. 267 851).

In some cases, quorum sensing-responsive promoters can be employed in the expression cassettes/vectors. Quorum sensing is a mechanism whereby bacteria are able to indirectly detect the concentration of neighboring cells. A quorum sensing pathway is one that is usually activated when a bacterial population becomes concentrated. For example, biofilm formation is controlled often by quorum sensing. Such quorum sensing promoters can make bacteria, cyanobacteria, or other cells self-induce the genes of interest when a certain cell concentration is reached (e.g., when the cells are ready, or will soon be ready, to be harvested), without the addition of chemical inducers. See, e.g., Miller, Melissa B., and Bonnie L. Bassler. "Quorum sensing in bacteria." Annual Reviews in Microbiology 55(1): 165-199 (2001).

In some cases, the promoter can become active at certain times during culture or fermentation. For example, the promoter can in some cases be active before, during, or after log phase growth of the cells during culture or fermentation.

For example. LuxI/LuxR genes are a family of genes that produce quorum sensing behavior in bacteria. See, e.g., Waters & Bassler, "Quorum sensing: cell-to-cell communication in bacteria." Ann Rev Cell Dev Biol 21: 319-46 (2005). Quorum sensing pathways in natural contexts involve a microbe that is capable of producing a diffusible molecule that can pass through the cell membrane, such as the class of molecules called acyl-homoserine lactones (AHL). These molecules can diffuse from the cell that produces them to the outside environment, and then back into other neighboring bacteria. When the concentration of AHL of a specific type becomes high enough, it can stabilize a transcription factor that turns on specific genes. Usually, quorum sensing pathways are utilized for bacteria to sense how large its population is—the more surrounding bacteria in the environment, the higher the AHL levels. At a certain cell density, the AHL builds up to a level that it can bind a receptor protein (e.g. LuxR), stabilizing it and allowing for downstream gene regulation.

Quorum sensing-responsive promoters can be used in any of the expression cassettes or expression vectors described herein. For example, host cells expressing LuxI (or similar protein) can make an AHL signal that could then build up as the cell density increases. When the cells become dense enough, they can turn on the expression of chimeric carboxysome core protein(s), shell protein(s), Rubisco protein(s), or combinations thereof.

One example of a protein that can modulate quorum sensing-responsive promoters is the LuxI from *Vibrio fishcheri*, with the following sequence (SEQ ID NO:30).

```
  1  MIKKSDFLGI PSEEYRGILS LRYQVFKRRL EWDLVSEDNL

41  ESDEYDNSNA EYIYACDDAE EVNGCWRLLP TTGDYMLKTV

81  FPELLGDQVA PRDPNIVELS RFAVGKNSSK INNSASEITM

121  KLFQAIYKHA VSQGITEYVT VTSIAIERFL KRIKVPCHRI

161  GDKEIHLLGN TRSVVLSMPI NDQFRKAVSN
```

A nucleic acid encoding this *Vibrio fishcheri* LuxI protein shown below (SEQ ID NO:31).

```
  1  ATGATAAAAA AATCGGACTT TTTGGGCATT CCATCAGAGG

41  AGTATAGAGG TATTCTTAGT CTTCGTTATC AGGTATTTAA

81  ACGAAGACTG GAGTGGGACT TGGTAAGTGA GGATAATCTT

121  GAATCAGATG AAATATGATAA CTCAAATGCA GAATATATTT

161  ATGCTTGTGA TGATGCGGAA GAGGTAAATG GCTGTTGGCG

201  TTTGTTACCT ACAACGGGTG ATTACATGTT AAAAACTGTT
```

```
241 TTTCCTGAAT TGCTCGGAGA TCAAGTAGCC CCAAGAGATC
281 CAAATATAGT CGAATTAAGC CGTTTTGCTG TGGGAAAAAA
321 TAGCTCAAAA ATAAATAACT CTGCTAGTGA AATAACAATG
361 AAATTGTTTC AAGCTATATA TAAACACGCA GTTAGTCAAG
401 GTATTACAGA ATATGTAACA GTAACATCAA TAGCAATAGA
441 GCGATTTCTG AAACGTATTA AAGTTCCTTG TCATCGCATT
481 GGTGATAAGG AGATTCATTT ATTAGGTAAT ACTAGATCTG
521 TTGTATTGTC TATGCCTATT AATGATCAGT TTAGAAAAGC
561 TGTATCAAAT TAA
```

A sequence of a LuxR receptor protein from *Vibrio fishcheri* is shown below (SEQ ID NO:32).

```
  1 MIYNTQNLRQ TIGKDKEMGM KNINADDTYR IINKIKACRS
 41 NNDINQCLSD MTKMVHCEYY LLAIIYPHSM VKSDISILDN
 81 YPKKWRQYYD DANLIKYDPI VDYSNSNHSP INWNIFENNA
121 VNKKSPNVIK EAKTSGLITG FSFPIHTANN GFGMLSFAHS
161 EKDNYIDSLF LHACMNIPLI VPSLVDNYRK INIANNKSNN
201 DLTKREKECL AWACEGKSSW DISKILGCSE RTVTFHLTNA
241 QMKLNTTNRC QSISKAILTG AIDCPYFKN
```

A nucleic acid sequence for this LuxR protein from *Vibrio fishcheri* is provided below as SEQ ID NO:33.

```
  1 ATGATATATA ACACGCAAAA CTTGCGACAA ACAATAGGTA
 41 AGGATAAAGA GATGGGTATG AAAAACATAA ATGCCGACGA
 81 CACATACAGA ATAATTAATA AAATTAAAGC TTGTAGAAGC
121 AATAATGATA TTAATCAATG CTTATCTGAT ATGACTAAAA
161 TGGTACATTG TGAATATTAT TTACTCGCGA TCATTTATCC
201 TCATTCTATG GTTAAATCTG ATATTTCAAT TCTAGATAAT
241 TAGCCTAAAA AATGGAGGCA ATATTATGAT GACGCTAATT
281 TAATAAAATA TGATCCTATA GTAGATTATT CTAACTCCAA
321 TCATTCACCA ATTAATTGGA ATATATTTGA AAACAATGCT
361 GTAAATAAAA AATCTCCAAA TGTAATTAAA GAAGCGAAAA
401 CATCAGGTCT TATCACTGGG TTTAGTTTCC CTATTCATAC
441 GGCTAACAAT GGCTTCGGAA TGCTTAGTTT TGCACATTCA
481 GAAAAAGACA ACTATATAGA TAGTTTATTT TTACATGCGT
521 GTATGAACAT ACCATTAATT GTTCCTTCTC TAGTTGATAA
561 TTATCGAAAA ATAAATATAG CAAATAATAA ATCAAACAAC
601 GATTTAACCA AAAGAGAAAA AGAATGTTTA GCGTGGGCAT
641 GCGAAGGAAA AAGCTCTTGG GATATTTCAA AAATATTAGG
681 CTGCAGTGAG CGTACTGTCA CTTTCCATTT AACCAATGCG
721 CAAATGAAAC TCAATACAAC AAACCGCTGC CAAAGTATTT
761 CTAAAGCAAT TTTAACAGGA GCAATTGATT GCCCATACTT
801 TAAAAATTAA
```

An example of a LuxR-responsive promoter from *Vibrio fishcheri* is shown below as (SEQ ID NO:34).

```
  1 TGTCGCAAGT TTTGCGTGTT ATATATCATT AAAACGGTAA
 41 TGGATTGACA TTTGATTCTA ATAAATTGGA TTTTTGTCAC
 81 ACTATTGTAT CGCTGGGAAT ACAATTACTT AACATAAGCA
121 CCTGTAGGAT CGTACAGGTT TACGCAAGAA AATGGTTTGT
161 TATAGTCGAA TGAATTCATT AAAGAGGAGA AAGGTACC
```

When LuxR is expressed and stabilized (because AHL is present), the LuxR protein binds to a promoter sequence like that shown above as (SEQ ID NO:34) and drives gene expression from it.

It is understood that many promoters and associated regulatory elements may be used within the expression cassette/vector to transcribe an RNA encoding a chimeric carboxysome core protein. The promoters described above are provided merely as examples and are not to be considered as a complete list of promoters that are included within the scope of the invention.

The expression cassette of the invention may contain a nucleic acid sequence for increasing the translation efficiency of an mRNA encoding a chimeric carboxysome core protein. Such increased translation serves to increase production of the protein. The presence of an efficient ribosome binding site is useful for gene expression in prokaryotes. In bacterial mRNA, a conserved stretch of six nucleotides, the Shine-Dalgarno sequence, is usually found upstream of the initiating AUG codon. (Shine et al., *Nature.* 254:34 (1975)). This sequence is thought to promote ribosome binding to the mRNA by base pairing between the ribosome binding site and the 3' end of *Escherichia coli* 16S rRNA. (Steitz et al., "Genetic signals and nucleotide sequences in messenger RNA", in: Biological Regulation and Development: Gene Expression (ed. R. F. Goldberger), 1979)). Such a ribosome binding site, or operable derivatives thereof, are included within the expression cassette of the invention.

A translation initiation sequence can be derived from any expressed gene and can be used within an expression cassette/vector of the invention. Preferably the gene from which the translation initiation sequence is obtained is a highly expressed gene. A translation initiation sequence can be obtained via standard recombinant methods, synthetic techniques, purification techniques, or combinations thereof, which are all well known. (Ausubel et al., *Current Protocols in Molecular Biology*, Green Publishing Associates and Wiley Interscience, N.Y. (1989); Beaucage and Caruthers. *Tetra. Letts.,* 22:1859 (1981); VanDevanter et al., *Nucleic Acids Res.,* 12:6159 (1984). Alternatively, translational start sequences can be obtained from numerous commercial vendors. (Operon Technologies: Life Technologies Inc. Gaithersburg. Md.). In some embodiments, the T7 translation initiation sequence is used. The T7 translation initiation sequence is derived from the highly expressed T7 Gene 10 cistron and can have a sequence that includes TCTAGAAATAATTTTGTTTAACTTTAAGAA GGAGATATA (SEQ ID NO:35). Other examples of translation initiation sequences include, but are not limited to, the maltose-binding protein (Mal E gene) start sequence (Guan et al., *Gene*, 67:21 (1997)) present in the pMalc2 expression vector (New England Biolabs, Beverly, Mass.) and the translation initiation sequence for the following genes: thioredoxin gene (Novagen, Madison, Wis.), Glutathione-S-transferase gene (Pharmacia, Piscataway, N.J.), β-galactosidase gene, chloramphenicol acetyltransferase gene and *E. coli* Trp E gene (Ausubel et al., 1989, *Current Protocols in Molecular Biology*, Chapter 16, Green Publishing Associates and Wiley Interscience, N.Y.).

The invention therefore provides an expression cassette or vector that includes a promoter operable in a selected host and a nucleic acid encoding one of the chimeric carboxysome core proteins described herein. The expression cassette can have other elements, for example, termination signals, origins of replication, enhancers, and the like as described herein. The expression cassette can also be placed in a vector for easy replication and maintenance.

An expression cassette or nucleic acid construct of the invention is thought to be particularly advantageous for inducing expression of the polypeptides.

Host Organisms

The chimeric carboxysome core protein can be expressed by a variety of organisms. Examples of organisms that can be modified to express the chimeric carboxysome core protein can include microorganisms, plants (including land-based plants and aqueous plants), and fungi. For example, bacteria, cyanobacteria, algae, microalgae, seaweed, plankton, single-celled fungal cells, multi-celled fungi, plant cells, and multi-celled plants can be modified to express the chimeric carboxysome core protein.

In some cases, the chimeric carboxysome core protein can be expressed in addition to native or endogenous carboxysome components.

Any cyanobacteria can be modified to express the chimeric carboxysome core protein, either permanently or transiently.

Examples of cyanobacterial species that can be changed include *Synechococcus elongatus* sp. PCC 7942; *Synechococcus elongatus* 7002: *Synechococcus elongatus* UTEX 2973; *Anthropira platensis*; and *Leptolyngbya* sp. strain BL0902. *Synechococcus elongatus* sp. PCC 7942 is one of the dominant model organisms, providing a variety of useful genetic tools. *Synechococcus elongatus* 7002 is a well-developed model organism with improved productivity and resilience. *Synechococcus elongatus* UTEX 2973 is related to *S. elongatus* 7942, and it has greatly improved growth properties. *Anthropira platensis* is perhaps the most broadly utilized cyanobacteria in scaled applications. *Leptolyngbya* sp. strain BL0902 is a bioindustrial strain whose genetic make-up is not as well-studied as some of the model cyanobacterial species.

Further examples of cyanobacterial species that can be modified include, for example, any of those in Table 1.

TABLE 1

Types of Cyanobacteria

| Species | Lineage | Release |
|---|---|---|
| *Synechococcus elongatus* sp. PCC 7942 | Cyanobacteria; Oscillatoriophycideae; Chroococcales; *Synechococcus* | American Type Culture Collection, ATCC accession No. 33912. |
| *Synechococcus elongatus* UTEX 2973 | Cyanobacteria; Oscillatoriophycideae; Chroococcales; *Synechococcus* | UTEX Culture Collection of Algae, University of Texas at Austin |
| *Anthropira platensis* | Cyanobacteria; Oscillatoriophycideae; Oscillatoriales; *Arthrospira* | American Type Culture Collection, ATCC accession No. 29408. |
| *Prochlorococcus marinus* str. AS9601 | Cyanobacteria; Prochlorales; Prochlorococcaceae; *Prochlorococcus* | The Gordon and Betty Moore Foundation Marine Microbiology Initiative (2007) |
| *Acaryochloris marina* MBIC11017 | Cyanobacteria; *Acaryochloris* | TGen Sequencing Center (2008) |
| *Anabaena* sp. PCC 7120 | Cyanobacteria; Nostocales; Nostocaceae; *Nostoc* | Kazusa (2001) |
| *Anabaena variabilis* ATCC 29413 | Cyanobacteria; Nostocales; Nostocaceae; *Anabaena* | JGI (2007) |
| *Synechococcus* sp. CC9311 | Cyanobacteria; Chroococcales; *Synechococcus* | TIGR (2006) |
| *Cyanothece* sp. ATCC 51142 | Cyanobacteria; Chroococcales; *Cyanothece* | Washington University (2008) |
| *Chlorobium tepidum* TLS | Chlorobi; Chlorobia; Chlorobiales; Chlorobiaceae; *Chlorobaculum* | TIGR (2002) |
| *Synechococcus* sp. JA-3-3Ab | Cyanobacteria; Chroococcales; *Synechococcus* | TIGR (2007) |
| *Cyanothece* sp. PCC 7425 | Cyanobacteria; Chroococcales; *Cyanothece* | |
| *Synechococcus* sp. JA-2-3B'a(2-13) | Cyanobacteria; Chroococcales; *Synechococcus* | TIGR (2007) |
| *Gloeobacter violaceus* PCC 7421 | Cyanobacteria; Gloeobacteria; Gloeobacterales; *Gloeobacter* | Kazusa(2003) |
| *Prochlorococcus marinus* MED4 | Cyanobacteria; Prochlorales; Prochlorococcaceae; *Prochlorococcus* | JGI (2003) |
| *Microcystis aeruginosa* NIES-843 | Cyanobacteria; Chroococcales; *Microcystis* | Kazusa, Tsukuba, NIES (2007) |
| *Prochlorococcus marinus* MIT9313 | Cyanobacteria; Prochlorales; Prochlorococcaceae; *Prochlorococcus* | JGI (2003) |

TABLE 1-continued

Types of Cyanobacteria

| Species | Lineage | Release |
|---|---|---|
| *Prochlorococcus marinus* str. NATL1A | Cyanobacteria; Prochlorales; Prochlorococcaceae; *Prochlorococcus* | The Gordon and Betty Moore Foundation Marine Microbiology Initiative (2007) |
| *Arthrospira platensis* NIES-39 | Cyanobacteria; Oscillatoriales; *Arthrospira*; *Arthrospira platensis* | |
| *Nostoc punctiforme* ATCC 29133 | Cyanobacteria; Nostocales; Nostocaceae; *Nostoc* | JGI (2008) |
| *Prochlorococcus marinus* str. MIT 9211 | Cyanobacteria; Prochlorales; Prochlorococcaceae; *Prochlorococcus* | The Gordon and Betty Moore Foundation Marine Microbiology Initiative (2008) |
| *Prochlorococcus marinus* str. MIT 9215 | Cyanobacteria; Prochlorales; Prochlorococcaceae; *Prochlorococcus* | JGI (2007) |
| *Prochlorococcus marinus* str. MIT 9301 | Cyanobacteria; Prochlorales; Prochlorococcaceae; *Prochlorococcus* | The Gordon and Betty Moore Foundation Marine Microbiology Initiative (2007) |
| *Prochlorococcus marinus* str. MIT 9303 | Cyanobacteria; Prochlorales; Prochlorococcaceae; *Prochlorococcus* | The Gordon and Betty Moore Foundation Marine Microbiology Initiative (2007) |
| *Prochlorococcus marinus* str. MIT 9515 | Cyanobacteria; Prochlorales; Prochlorococcaceae; *Prochlorococcus* | The Gordon and Betty Moore Foundation Marine Microbiology Initiative (2007) |
| *Synechococcus elongatus* PCC 6301 | Cyanobacteria; Chroococcales; *Synechococcus* | Nagoya U. (2007) |
| *Cyanothece* sp. PCC 7424 | Cyanobacteria; Chroococcales; *Cyanothece* | |
| *Cyanothece* sp. PCC 8801 | Cyanobacteria; Chroococcales; *Cyanothece* | |
| *Prochlorococcus marinus* str. NATL2A | Cyanobacteria; Prochlorales; Prochlorococcaceae; *Prochlorococcus* | JGI (2007) |
| *Prochlorococcus marinus* str. MIT 9312 | Cyanobacteria; Prochlorales; Prochlorococcaceae; *Prochlorococcus* | JGI (2007) |
| *Rhodopseudomonas palustris* CGA009 | Proteobacteria; Alphaproteobacteria; Rhizobiales; Bradyrhizobiaceae; *Rhodopseudomonas* | JGI (2003) |
| *Prochlorococcus marinus* SS120 | Cyanobacteria; Prochlorales; Prochlorococcaceae; *Prochlorococcus* | Genoscope (2003) |
| *Synechococcus* sp. CC9605 | Cyanobacteria; Chroococcales; *Synechococcus* | JGI (2007) |
| *Synechococcus* sp. CC9902 | Cyanobacteria; Chroococcales; *Synechococcus* | JGI (2007) |
| *Synechocystis* sp. PCC 6803 | Cyanobacteria; Chroococcales; *Synechocystis* | Kazusa (1996, 2002, 2003) |
| *Synechococcus* sp. PCC 7002 | Cyanobacteria; Chroococcales; *Synechococcus* | Penn State University (2008) |
| *Synechococcus elongatus* PCC 7942 | Cyanobacteria; Chroococcales; *Synechococcus* | JGI (2007) |
| *Synechococcus* sp. RCC307 | Cyanobacteria; Chroococcales; *Synechococcus* | Genoscope (2007) |
| *Synechococcus* sp. WH 7803 | Cyanobacteria; Chroococcales; *Synechococcus* | Genoscope (2007) |
| *Trichodesmium erythraeum* IMS101 | Cyanobacteria; Oscillatoriales; *Trichodesmium*; *Trichodesmium erythraeum* | |
| *Thermosynechococcus elongatus* BP-1 | Cyanobacteria; Chroococcales; *Thermosynechococcus* | Kazusa (2002) |
| *Synechococcus* sp. WH8102 | Cyanobacteria; Chroococcales; *Synechococcus* | JGI (2003) |

Useful Products

The cells, plants, cyanobacteria, bacteria, algae, microalgae and other cells/organisms that express the fusion proteins described herein can produce a variety of products such as oils, carbohydrates, grains, vegetables, fruits and other components, as well as 3-phosphoglycerate (3-PGA). Examples include oils (fatty acids), alkenes, polyhydroxybutyrate, biomass, carbohydrates, phycocyanin, ethanol, hydrogen, isobutanol, ethylene, and combinations thereof. Products such as oils (fatty acids), alkenes, ethanol, hydrogen, isobutanol, ethylene, and combinations thereof can be used in manufacturing and as biofuels. For example, ethanol, carbohydrate feedstocks, and biomass can be used to make bioethanol. Polyhydroxybutyrate is useful, for example, in bioplastics. Biomass, carbohydrates, and ethanol can also be used in foods and food manufacturing. Ethanol, hydrogen, isobutanol, and ethylene are useful in manufacturing, as a source of energy, and/or for making fuel.

The following non-limiting Examples describe some of the experiments performed.

Example 1: Materials and Methods

This Example describes some of the methods that were used during development of the invention.

Cyanobacterial Strain and Growth Conditions

*Synechococcus elongatus* PCC 7942 (Syn 7942) cultures were grown in 250 ml baffled Erlenmeyer flasks with 60 ml BG-11 medium (Rippka et al., 1979) buffered with 10 mM HEPES pH 8.0 under the following growth chamber settings: temperature of 30° C., light intensity of 40 µmoles photons $m^{-2}s^{-1}$, shaking at 150 rpm and $CO_2$ concentrations of 5%, 3% or air. Unless otherwise indicated, experiments were performed in cultures at exponential growth phase ($OD_{730}$=0.4-0.7).

Mutant Generation

*Synechococcus elongatus* PCC 7942 cells were transformed as described by Kufryk et al. (2002). Cultures were grown to $OD_{730}$=0.5 and concentrated to $OD_{730}$=2.5 by centrifugation at 5000 relative centrifugal force (rcf) for 5 minutes. Five microliters of plasmids (~1 µg of DNA) prepared from *E. coli* DH5α cells were added to 400 µl of the cyanobacterial cell suspension and incubated for 6 hours. The 400 µl-aliquots were dried on Nucleopore track-etched polycarbonate membranes (GE Healthcare) on top of BG-11 plates and incubated for 12-24 hours. The membranes were transferred to BG-11 plates with the proper selectable marker until resistant colonies were obtained.

All mutant strains were transformed with pJCC008 plasmid (rbcL-GFP placed under the control of the ccmk2 promoter) (Cameron et al., 2013) for GFP-labeling of the large subunit of Rubisco (RbcL) to enable carboxysome visualization by fluorescence microscopy. The carboxysome-minus strain COREΔ2/RbcL-GFP was generated by replacing synpcc7942_1423 and synpcc7942_1424 genes with a kanamycin resistance/sucrose sensitivity cassette obtained from the pPSBAII-KS plasmid (Lagarde et al., 2000) and using synpcc7942_1422 and synpcc7942_1425 sequences as flanking regions for double homologous recombination. Domains for the generation of chimeric proteins were assigned using the InterPro software (Hunter et al., 2012) and the HMM tool from JCVI institute (see website at blast.jcvi.org/web-hmm).

DNA was obtained from Cyanobase (see website at genome.microbedb.jp/cyanobase) and cloned by methods involving restriction digestion and ligation (see, e.g., Sambrook and Russell, 2001) as follows.

Plasmids with genes coding for the chimeric proteins had the following amino acid sequences.

The following is an amino acid sequence for a CcaA-M35 gene (SEQ ID NO:36).

```
  1   MRKLIEGLRH FRISYYPSHR DLFEQFAKGQ HPRVLFITCS
 41   DSRIDPNLIT QSGMGELFVI RNAGNLIPPE GAANGGEGAS
 81   IEYAIAALNI EHVVVCGHSH CGAMKGLLKL NQLQEDMPLV
121   YDWLQHAQAT RRLVLDNYSG YETDDLVEIL VAENVLTQIE
141   NLKTYPIVRS RLFQGKLQIF GWIYEVESGE VLQISRTSSD
181   DTGIDECPVR LPGSQEKAIL GRCVVPLTEE VAVAPPEPEP
221   VIAAVAAPPA NYSSRGWLAP EQQQRIYRGN ASGSVSAYNG
261   QGRLSSEVIT QVRSLLNQGY RIGTEHADKR RFRTSSWQPC
281   APIQSTNERQ VLSELENCLS EHEGEYVRLL GIDTNTRSRV
321   FEALIQRPDG SVPESLGSQP VAVASGGGRQ SSYASVSGNL
361   SAEVVNKVRN LLAQGYRIGT EHADKRRFRT SSWQSCAPIQ
401   SSNERQVLAE LENCLSEHEG EYVRLLGIDT ASRSRVFEAL
441   IQDPQGPVGS AKAAAAPVSS ATPSSHSYTS NGSSSSDVAG
481   QVRGLLAQGY RISAEVADKR RFQTSSWQSL PALSGQSEAT
521   VLPALESILQ EHKGKYVRLI GIDPAARRRV AELLIQKP

1   MTVSAYNGQG RLSSEVITQV RSLLNQGYRI GTEHADKRRF
 41   RTSSWQPCAP IQSTNERQVL SELENCLSEH EGEYVRLLGI
 81   DTNTRSRVFE ALIQRPDGSV PESLGSQPVA VASGGGRQSS
121   YASVSGNLSA EVVNKVRNLL AQGYRIGTEH ADKRRFRTSS
161   WQSCAPIQSS NERQVLAELE NCLSEHEGEY VRLLGIDTAS
201   RSRVFEALIQ DPQGPVGSAK AAAAPVSSAT PSSHSYTSNG
241   SSSSDVAGQV RGLLAQGYRI SAEVADKRRF QTSSWQSLPA
281   LSGQSEATVL PALESILQEH KGKYVRLIGI DPAARRRVAE
321   LLIQKPGSGG SVYGKEQFLR MRQSMFPDR
```

The following is an amino acid sequence for a CcmC protein (SEQ ID NO:38).

```
  1   MTVSAYNGQG RLSSEVITQV RSLLNQGYRI GTEHADKRRF
 41   RTSSWQPCAP IQSTNERQVL SELENCLSEH EGEYVRLLGI
 81   DTNTRSRVFE ALIQRPDGSV PESLGSQPVA VASGGGRQSS
121   YASVSGNLSA EVVNKVRNLL AQGYRIGTEH ADKRRFRTSS
161   WQSCAPIQSS NERQVLAELE NCLSEHEGEY VRLLGIDTAS
201   RSRVFEALIQ DPQGPVGSAK AAAAPVSSAT PSSHSYTSNG
241   SSSSDVAGQV RGLLAQGYRI SAEVADKRRF QTSSWQSLPA
281   LSGQSEATVL PALESILQEH KGKYVRLIGI DPAARRRVAE
321   LLIQKPGSRK LIEGLRHFRT SYYPSHRDLF EQFAKGQHPR
361   VLFITCSDSR IDPNLITQSG MGELFVIRNA GNLIPPFGAA
401   NGGEGASIEY AIAALNIEHV VVCGHSHCGA MKGLLKLNQL
441   QEDMPLVYDW LQHAQATRRL VLDNYSGYET DDLVEILVAE
481   NVLTQIENLK TYPIVRSRLE QGKLQIFGWI YEVESGEVLQ
521   ISRTSSDDTG IDECPVRLPG SQEKAILGRC VVPLTEEVAV
```

-continued

561 APPEPEPVIA AVAAPPANYS SRGWLGSGGS VYGKEQFLRM

601 RQSMFPDR

Note that amino acids 1-328 of the CcmC protein (with SEQ ID NO:38) are the same as amino acids 1-328 of the M35-EP protein with SEQ ID NO:37. The central amino acids 329-585 (in bold) of the SEQ ID NO:38 CcmC protein correspond to amino acids 2-258 of the carbonate dehydratase (CcaA) with SEQ ID NO:71. Amino acids 591-608 of the SEQ ID NO:38 CcmC protein correspond to the encapsulation peptide from a CcmN protein, which has SEQ ID NO: 13.

Note also that in the case of CcmC the C-terminal extension of the β-CA was used as linker and its terminal 14 amino acids were replaced by 18 amino acids comprising the EP with synpcc7942_1422 and synpcc7942_1425 sequences as flanking regions were transformed into the COREΔ2/RbcL-GFP strain.

Growth in air was used for positive selection and growth in 5% sucrose as confirmation. The COREΔ2/CcmC/RbcL-GFP strain is obtained after CcmC restores growth in air. CcaA (Synpcc7942_1447) was interrupted in the COREΔ2/CcmC/RbcL-GFP strain and in Wild-type/RbcL-GFP by insertion of a gentamycin resistance cassette and selection with 5 μg/ml gentamycin in solid BG-11 plates (resulting in COREΔ3/CcmC/RbcL-GFP strain and ΔCcaA/RbcL-GFP strain, respectively). Primers used are described in Table 2.

TABLE 2

Primers

| Primer ID | Purpose | Sequence |
|---|---|---|
| pUC19 spel fwd | CcmM-N deletion | GGTGCACTACTAGTACAATCTGC (SEQ ID NO: 39) |
| pUC19 spel rv | CcmM-N deletion | GTGAAATACCGCACTAGTGCGTAAG (SEQ ID NO: 40) |
| FR left (ccmL-O) fwd | CcmM-N deletion | CTTTCATCTTGAATTCCGACTCTTTAGG (SEQ ID NO: 41) |
| FR left (ccmL-O) rv | CcmM-N deletion | GCTCGGCATATGCTAACCTC (SEQ ID NO: 42) |
| FR right (ccmL-O) fwd | CcmM-N deletion | GGGAGGTTAGCATATGCTCTAGAAGCTGCAGG (SEQ ID NO: 43) |
| FR right (ccmL-O) rv | CcmM-N deletion | CTACTGAGTCCGAAGCTTTCAGC (SEQ ID NO: 44) |
| Km$^R$/SacB fwd | CcmM-N deletion | GAATTATAACCATATGCATCCTAGG (SEQ ID NO: 45) |
| Km$^R$/SacB rv | CcmM-N deletion | TCCCGTCTAGACAGCGTAATG (SEQ ID NO: 46) |
| CcaA ndeI fwd | ccmC, ccaA-M35 | GAGTATCACTCATATGCGCAAGC (SEQ ID NO: 47) |
| CcaA BamHI rv | ccaA-M35 | CTTCGGGATCCGCTAGCATTG (SEQ ID NO: 48) |
| SSLDs-CcmN bglII fwd- | ccaA-M35 | TAGCGAGGCAAGATCTGTGAGC (SEQ ID NO: 49) |
| SSLDs-CcmN xhoI rv- | ccaA-M35 | CCTGCAGCTTCTAGAGCTGCTGTG (SEQ ID NO: 50) |
| CcaA$_{(short)}$ bamHI rv | ccmC | GTTGTTGTTCGGATCCCAACCAAC (SEQ ID NO: 51) |
| EP bglII fwd | ccmC, M35-EP | CCCAGATCTGGAGGCAGTGTCTACGGCAAGGAAC (SEQ ID NO: 52) |
| EP NcoI rv | ccmC, M35-EP | CGTGGCCATGGCTTCTTGGGAGAGC (SEQ ID NO: 53) |
| ccaA$_{(short)}$ bglII fwd | ccmC | GCCCTTGTCAGATCTCGCAAGCTCATCG (SEQ ID NO: 54) |
| SSLDs ndeI fwd | ccmC, M35-EP | CTAGCGAGCATATGACCGTGAGCGC (SEQ ID NO: 55) |
| SSLDs bamHI rv | ccmC, M35-EP | CAGGATCCTCCCGGCTTTTGTTAGAGC (SEQ ID NO: 56) |
| FR left (ccaA) notI fwd | CcaA deletion | CAGCGGCCGCGCCTAGTGC (SEQ ID NO: 57) |

TABLE 2-continued

Primers

| Primer ID | Purpose | Sequence |
|---|---|---|
| FR left (ccaA) xhoI rv | CcaA deletion | GCTTGCGCATCTCGAGTGATACTCGGGAC (SEQ ID NO: 58) |
| FR right (ccaA) xbaI fwd | CcaA deletion | GCGGCAATTCTAGATAGGATCGAAGCATC (SEQ ID NO: 59) |
| FR right (ccaA) ncoI rv | CcaA deletion | TACCCATGGACTCAAGCGCTCATTGCCAG (SEQ ID NO: 60) |
| $Gm^R$ xhoI fwd | CcaA deletion | GGTACCGAGCTCGAGTTGACATAAGC (SEQ ID NO: 61) |
| $Gm^R$ xbaI rv | CcaA deletion | TCCGCGGCTCTAGAGCCGATC (SEQ ID NO: 62) |
| Primer A | Screening | TGCCTATTGCGGTTGGAATG (SEQ ID NO: 63) |
| Primer B | Screening | AATCATGATGCACGCCCTTG (SEQ ID NO: 64) |
| Primer C | Screening | AATCATGATGCACGCCCTTG (SEQ ID NO: 65) |
| Primer D | Screening | TTAGCCGATTTGAGCATGGC (SEQ ID NO: 66) |
| Primer E | Screening | CAGCTTTGAACATTGAGCATGTTGTG (SEQ ID NO: 67) |
| Primer F | Screening | ATTGCCGCGATAAATCCGCTG (SEQ ID NO: 68) |

Structural Modeling

The predicted domains obtained (FIG. 1A) were used as input for the automated mode of the SwissModel (Biasini et al., 2014) server. The EP was manually added to the predicted structure of CcmC using the software Chimera (Pettersen et al., 2004).

Spectrophotometric Measurements

Culture growth was monitored as the change in optical density at 730 nm ($OD_{730}$). Chl a concentration was determined by absorbance measurements (at 663 nm) of methanol extracts from 1-ml culture aliquots and calculated according to Lichtenthaler (Lichtenthaler, 1987). Total cell spectra were obtained from 1-ml aliquots of cultures in exponential growth phase, which were diluted to $OD_{730}$=0.3, and the obtained spectra were normalized to that of Chl a ($OD_3$). Doubling times were calculated using the exponential regression curve fitting online tool available at website doubling-time.com/compute.php. All measurements were performed at least in triplicate from aliquots from different cultures (using the same inoculum from a BG-11 agar plate). All measurements were performed in a Nanodrop2000C spectrophotometer (Thermo Scientific. USA).

PCR and Immunoblot Analysis

Standard PCR was performed as described in the manufacturer's protocol using EconoTaq Plus Green 2X (Lucigen, USA) and gene-specific primer pairs (Table 2). For protein extraction, pellets from 50 ml culture aliquots were resuspended in 1 ml of lysis buffer (25 mM HEPES-NaOH pH 7.15 mM $CaCl_2$, 5 mM $MgCl_2$, 15% Glycerol, 200 µM PMSF and cOmplete, Mini protease inhibitor (Roche)) and broken in a BeadBug homogenizer (Biospec Products, USA), by beating for 6 cycles of 30 seconds and 2 minutes of incubation in ice between each cycle. After 20 minutes of centrifugation at 20000 rcf, 15-µl aliquots plus SDS loading dye were loaded onto an acrylamide gel (without boiling the sample) for SDS-PAGE. SDS-PAGE and immunoblot analysis were performed according to the manufacturer's protocol (BioRad's bulletin 6376) using a polyclonal antibody from rabbit against Syn 7942 CcmM (dilution 1:5000) (Rothamstead Research, UK) as a primary antibody and Goat Anti-Rabbit IgG-HRP (Dilution 1:7000) (Life Tech. #656120) as secondary antibody and 1-Step Ultra TMB-Blotting Solution as substrate (Thermo #37574). For densitometries, total protein extract samples from three independent cultures were normalized according to the peak absorbance at 663 nm, loaded at four decreasing serial dilutions, and blotted as described using Anti-RbcL antibody (Agrisera Cat. AS03 037) at a dilution of 1:10000. Densitometry measurements were performed on the different immunoblots using ImageJ software (Schneider et al., 2012).

Oxygen Evolution

Two-ml aliquots were harvested from exponential-phase cultures, supplemented with 10 mM bicarbonate prior to the measurement, and the steady-state rate of oxygen evolution was determined at saturating light intensity (950 µmoles photons $m^{-2}$ $s^{-1}$) and 30° C. using an LMI-6000 illuminator (Dolan-Jenner, USA) and an Oxygraph Plus Clark-type electrode (Hansatech. UK).

Fluorescence and Electron Microscopy

Cultures grown to $OD_{730}$=0.5 in 3% $CO_2$ were transferred to air and grown overnight. For fluorescence microscopy, 1-ml aliquots were concentrated by centrifugation (1500 rcf for 5 minutes and resuspended in 100 µl of BG11) and visualized (autofluorescence and GFP) using a Zeiss Axio Observer.D1 inverted microscope. For electron microscopy, pellets from 50-ml aliquots were chemically fixed with 2% glutaraldehyde in 50 mM phosphate buffer for 2 hours at room temperature, followed by 1% osmium tetroxide for 2 hours at room temperature, and block stained with 2% aqueous uranyl acetate overnight at 4° C. Cells were dehydrated in an increasing acetone series (2 minutes at 37° C.; 20% acetone increments) and embedded in Spurr's resin (15 minutes at 37° C.; 25% increments) using an MS-9000 Laboratory Microwave Oven (Electron Microscopy Science, USA). Sections (70 nm thick) were cut on a MYX ultramicrotome (RMC Products. USA), positively stained with 6% uranyl acetate and Reynolds lead citrate (Reynolds, 1963) and visualized on a JEM 100CX II transmission electron microscope (JEOL) equipped with an Orius SC200-830 CCD camera (Gatan Inc., USA).

Quantum Efficiency of Photosystem II $F_v/F_m$ was determined in triplicate using 4-ml culture aliquots from biological replicates at exponential phase in cells dark adapted for three minutes as described previously (Cameron et al., 2013). Briefly, aliquots were diluted with BG-11 immediately before dark adaptation to a chlorophyll concentration of ~1-2 µg/ml and measured using an Aquapen AP100 (Photon Systems Instruments. Czech Republic). Measurement started at time=0 h when the cultures were transferred from 3% $CO_2$ to air.

Sequences

Sequences can be found in the GenBank/EMBL data libraries. For example, an amino acid sequence for a *Synechococcus elongatus* PCC 7942 carbonate dehydratase (CcmM: Synpcc7942_1423) is available as accession number ABB57453 (SEQ ID NO:69).

```
  1  MPSPTTVPVA TAGRLAEPYI DPAAQVHAIA SIIGDVRIAA
 41  GVRVAAGVSI RADEGAPFQV GKESILQEGA VIHGLEYGRV
 81  LGDDQADYSV WIGQRVAITH KALIHGPAYL GDDCFVGFRS
121  TVFNARVGAG SVIMMHALVQ DVEIPPGRYV PSGAIITTQQ
161  QADRLPEVRP EDREFARHII GSPPVIVRST PAATADFHSI
201  PTPSPLRPSS SEATTVSAYN GQGRLSSEVI TQVRSLLNQG
241  YRIGTEHADK RRFRTSSWQP CAPIQSTNER QVLSELENCL
281  SEHEGEYVRL LGIDTNTRSR VFEALIQRPD GSVPESLGSQ
321  PVAVASGGGR QSSYASVSGN LSAEVVNKVR NLLAQGYRIG
361  TEHADKRRFR TSSWQSCAPI QSSNERQVLA ELENCLSEHE
401  GEYVRLLGID TASRSRVFEA LIQDPQGPVG SAKAAAAPVS
441  SATPSSHSYT SNGSSSSDVA GQVRGLLAQG YRISAEVADK
481  RRFQTSSWQS LPALSGQSEA TVLPALESIL QEHKGKYVRL
521  IGIDPAARRR VAELLIQKP
```

An amino acid sequence for a *Synechococcus elongatus* PCC 7942 carbon dioxide concentrating mechanism protein (CcmN: Synpcc7942_1424) is available as accession number ABB57454 (SEQ ID NO:70).

```
  1  MHLPPLEPPI SDRYFASGEV TIAADVVIAP GVLLIAEADS
 41  RIEIASGVCI GLGSVIHARG GAIIIQAGAL LAAGVLIVGQ
 81  SIVGRQACLG ASTTLVNTSI EAGGVTAPGS LLSAETPPTI
```

```
121  ATVSSSEPAG RSPQSSAIAH PTKVYGKEQF LRMRQSMFPD
161  R
```

An amino acid sequence for a *Synechococcus elongatus* PCC 7942 Carbonate dehydratase (CcaA; Synpcc7942_1447) is available as accession number ABB57477.1 (SEQ ID NO:71).

```
  1  MRKLIEGLRH FRTSYYPSHR DLEEQFAKGQ HPRVLFITCS
 41  DSRIDPNLIT QSGMGELFVI RNAGNLIPPF GAANGGEGAS
 81  IEYAIAALNI EHVVVCGHSH CGAMKGLLKL NQLQEDMPLV
121  YDWLQHAQAT RRLVLDNYSG YETDDLVEIL VAENVLTQIE
161  NLKTYPIVRS RLFQGKLQIF GWIYEVESGE VLQISRTSSD
201  DTGIDECPVR LPGSQEKAIL GRCVVPLTEE VAVAPPEPEP
241  VIAAVAAPPA NYSSRGWLAP EQQQRIYRGN AS
```

Example 2: Design of a Chimeric Protein that Supports Native Core Assembly and Cell Growth in Air This Example describes construction of chimeric proteins that assemble into a carboxysome core.

Figure 1D:
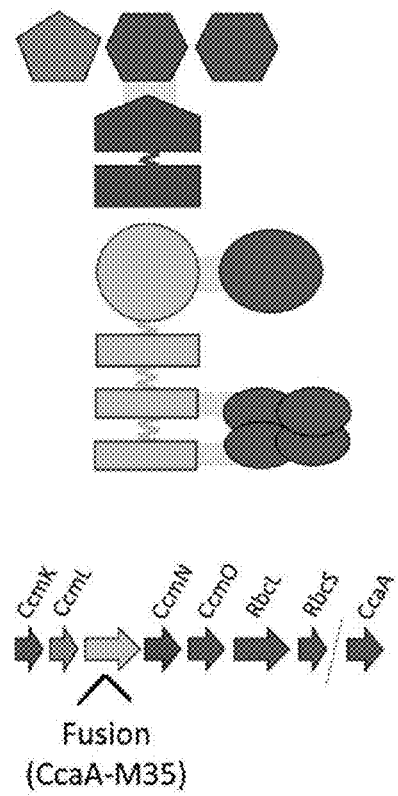
Figure 1E:
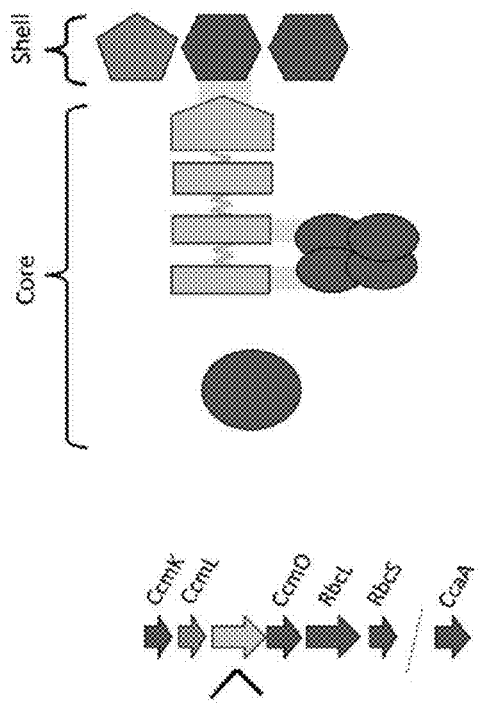
Figure 1F:
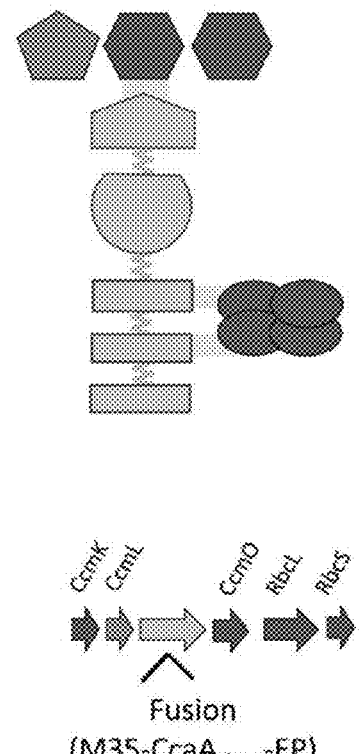
Figure 1H:
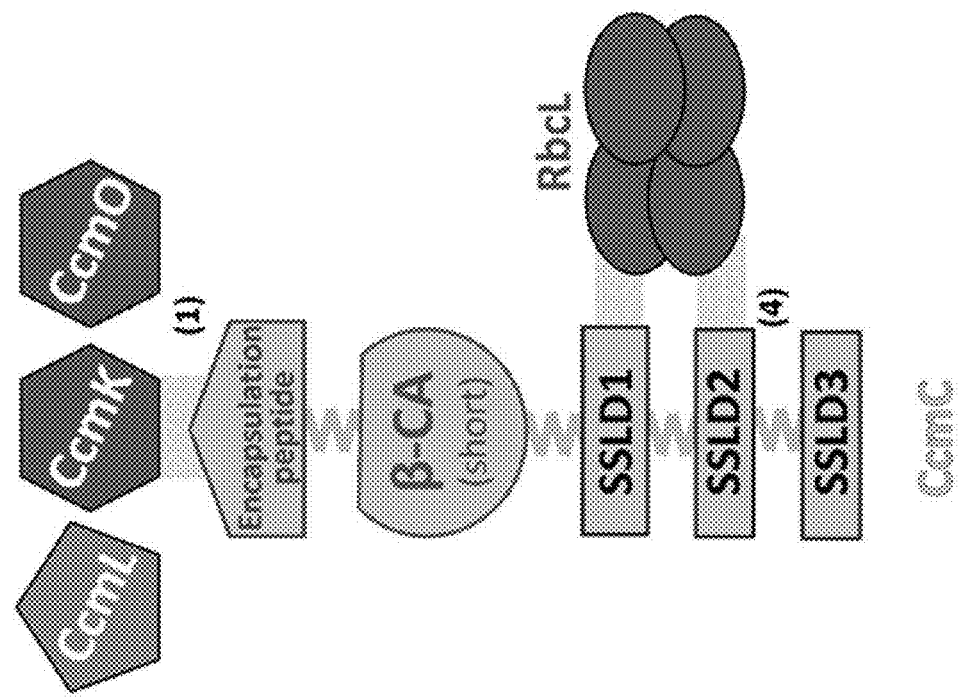
Figure 1G:
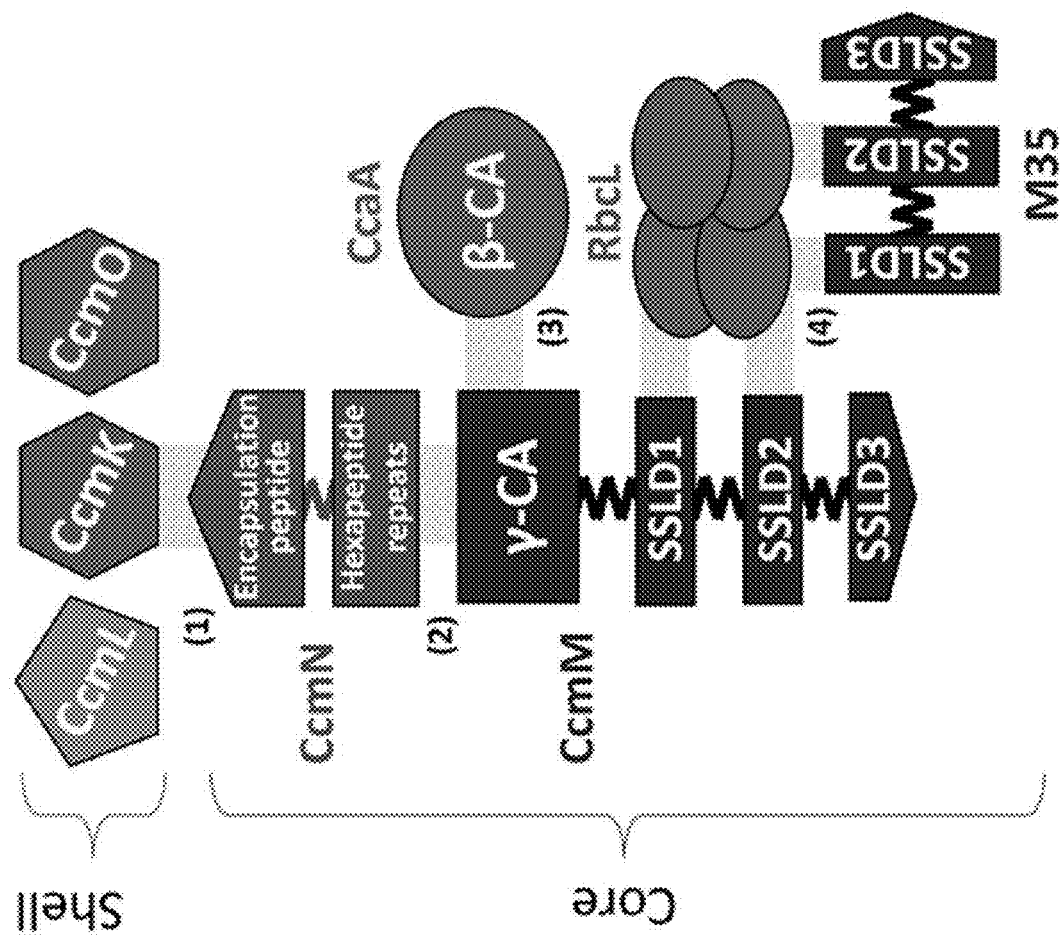

The design took into consideration observations that proteins evolve via domain fusions that are reflective of protein-protein interactions. The inventors predicted the domain boundaries in the CcmM, CcmN and CcaA proteins from *Synechococcus elongatus* PCC 7942 (FIG. 1A) using InterPro (Hunter et al., 2012). Three chimeric genes were then constructed encoding proteins that could assemble into a carboxysome core:

1) a ccaA-M35 fusion construct, where the γ-CA domain (Pfam00132) of CcmM was replaced by β-CA (Pfam00484) (FIG. 1D);

2) a M35-EP fusion construct, where three SSLD domains (Pfam00101) and their native linkers were fused to the EP (FIG. 1E); and 3) M35-ccaA$_{(short)}$-EP fusion construct, containing three SSLDs and their native linkers, the β-CA, CcaA with a short segment of its C-terminal tail as a linker, and the EP from the C-terminus of CcmN (FIG. 1B, 1F-1H).

A gene coding for a green fluorescent protein (GFP)-labeled large subunit of Rubisco (rbcL-GFP) was inserted into each strain for in vivo visualization of carboxysome formation by fluorescence microscopy (Savage et al., 2010). To test whether the chimeric proteins can assemble into a carboxysome core, the *Synechococcus elongatus* PCC 7942 ccmM and ccmN were replaced with selectable marker genes (COREΔ2/RbcL-GFP strain; her phenotype). The chimeric genes were then transformed via double homologous recombination to replace the selectable markers of the COREΔ2/RbcL-GFP strain (placing the genes under the same regulation of the ccm operon genes) using growth in air for positive selection. In the case of ccaA-M35, the ccmN gene was reintroduced in the same vector.

Only M35-ccaA$_{(short)}$-EP expression was able to rescue the her phenotype. This construct was named CcmC where the final "C" was for chimeric (FIG. 1H). The resulting strain (COREΔ2/CcmC/RbcL-GFP) contained the original ccaA in its genome. Therefore, to further substantiate the evident functional rescue by CcmC, the native caA was replaced with agent amycin resistance gene (resulting in strain COREΔ3/CcmCRbcL-GFP). This triple mutant strain was able to grow in air.

The presence or absence of ccmM, ccmN and ccaA was confirmed by PCR. Sequencing of the region between ccmL and ccmO further indicated that ccmnC was integrated into the ccm operon. The CCM insertion site sequence is shown below (SEQ ID NO:72), where the ccmC DNA insert is identified in bold and with underlining, and the portion of the genomic ccmK2 gene disrupted by the ccmC DNA insert is shown in bold (at the beginning of the SEQ ID NO:72 sequence).

```
   1  AGCCGCGGCA GTCAAGCGCG CCATGTGCGC GATTGTCAGG
  41  AACGACCGGT TGATGCAGCT GTCATTGCCA TCATCGATAC
  81  GGTCAACGTG GAAAACCGCT CCGTCTACGA CAAACGCGAG
 121  CACAGCTAAT GGGCAGGGAT TGAATCCCTG CTGGTCATTG
 161  ATCTGGATTG AGCCCAGGCT TGGGAGGTTA GCATATGACC
 201  GTGAGCGCTT ATAACGGCCA AGGCCGACTC AGTTCCGAAG
 241  TCATCACCCA AGTCCGGAGT TTGCTGAACC AGGGCTATCG
 281  GATTGGGACG GAACATGCGG ACAAGCGCCG CTTCCGGACT
 321  AGCTCTTGGC AGCCCTGCGC GCCGATTCAA AGCACGAACG
 361  AGCGCCAGGT CTTGAGCGAA CTGGAAAATT GTCTGAGCGA
 401  ACACGAAGGT GAATACGTTC GCTTGCTCGG CATCGATACC
 441  AATACTCGCA GCCGTGTTTT TGAAGCCCTG ATTCAACGGC
 481  CCGATGGTTC GGTTCCTGAA TCGCTGGGGA GCCAACCGGT
 521  GGCAGTCGCT TCCGGTGGTG GCCGTCAGAG CAGCTATGCC
 561  AGCGTCAGCG GCAACCTCTC AGCAGAAGTG GTCAATAAAG
 601  TCCGCAACCT CTTAGCCCAA GGCTATCGGA TTGGGACGGA
 641  ACATGCAGAC AAGCGCCGCT TCCGGACTAG CTCTTGGCAG
 681  TCCTGCGCAC CGATTCAAAG TTCGAATGAG CGCCAGGTTC
 721  TGGCTGAACT GGAAAACTGT CTGAGCGAGC ACGAAGGTGA
 761  GTACGTTCGC CTGCTGGGCA TCGACACTGC TAGCCGCAGT
 801  CGTGTTTTTG AAGCCCTGAT CCAAGATCCC CAAGGACCGG
 841  TGGGTTCCGC CAAAGCGGCC GCCGCACCTG TGAGTTCGGC
 881  AACGCCCAGC AGCCACAGCT ACACCTCAAA TGGATCGAGT
 921  TCGAGCGATG TCGCTGGACA GGTTCGGGGT CTGCTAGCCC
 961  AAGGCTACCG GATCAGTGCG GAAGTCGCCG ATAAGCGTCG
1001  CTTCCAAACC AGCTCTTGGC AGAGTTTGCC GGCTCTGAGT
1041  GGCCAGAGCG AAGCAACTGT CTTGCCTGCT TTGGAGTCAA
1081  TTCTGCAAGA GCACAAGGGT AAGTATGTGC GCCTGATTGG
1121  GATTGACCCT GCGGCTCGTC GTCGCGTGGC TGAACTGTTG
1161  ATTCAAAAGC CGGGATCTCG CAAGCTCATC GAGGGGTTAC
1201  GGCATTTCCG TACGTCCTAC TACCCGTCTC ATCGGGACCT
1241  GTTCGAGCAG TTTGCCAAAG GTCAGCACCC TCGAGTCCTG
1281  TTCATTACCT GCTCAGACTC GCGCATTGAC CCTAACCTCA
1321  TTACCCAGTC GGGCATGGGT GAGCTGTTCG TCATTCGCAA
1361  CGCTGGCAAT CTGATCCCGC CCTTCGGTGC CGCCAACGGT
1401  GGTGAAGGGG CATCGATCGA ATACGCGATC GCAGCTTTGA
1441  ACATTGAGCA TGTTGTGGTC TGCGGTCACT CGCACTGCGG
1481  TGCGATGAAA GGGCTGCTCA AGCTCAATCA GCTGCAAGAG
1521  GACATGCCGC TGGTCTATGA CTGGCTGCAG CATGCCCAAG
1561  CCACCCGCCG CCTAGTCTTG GATAACTACA GCGGTTATGA
1601  GACTGACGAC TTGGTAGAGA TTTCTGGTCGC CGAGAATGTG
1641  CTGACGCAGA TCGAGAACCT TAAGACCTAC CCGATCGTGC
1681  GATCGCGCCT TTTCCAAGGC AAGCTGCAGA TTTTTGGCTG
1721  GATTTATGAA GTTGAAAGCG GCGAGGTCTT GCAGATTAGC
1761  CGTACCAGCA GTGATGACAC AGGCATTGAT GAATGTCCAG
1801  TGCGTTTGCC CGGCAGCCAG GAGAAAGCCA TTCTCGGTCG
1841  TTGTGTCGTC CCCCTGACCG AAGAAGTGGC CGTTGCTCCA
1881  CCAGAGCCGG AGCCTGTGAT CGCGGCTGTG GCGGCTCCAC
1921  CCGCCAACTA CTCCAGTCGC GGTTGGTTGG GATCTGGAGG
1961  CAGTGTCTAC GGCAAGGAAC AGTTTTTGCG GATGCGCCAG
2001  AGCATGTTCC CCGATCGCTA AGATGTGCAC AGCAGCTCTA
2041  GGAGCTGCAG GGTACT
```

The portion of the sequence of the ccmL gene at the ccmC integration site is shown below (SEQ ID NO:73).

```
   1  AGCCGCGGCA GTCAAGCGCG CCATGTGCGC GATTGTCAGG
  41  AACGACCGGT TGATGCAGCT GTCATTGCCA TCATCGATAC
  81  GGTCAACGTG GAAAACCGCT CCGTCTACGA CAAACGCGAG
 121  CACAGCTAA
```

Figure 2:
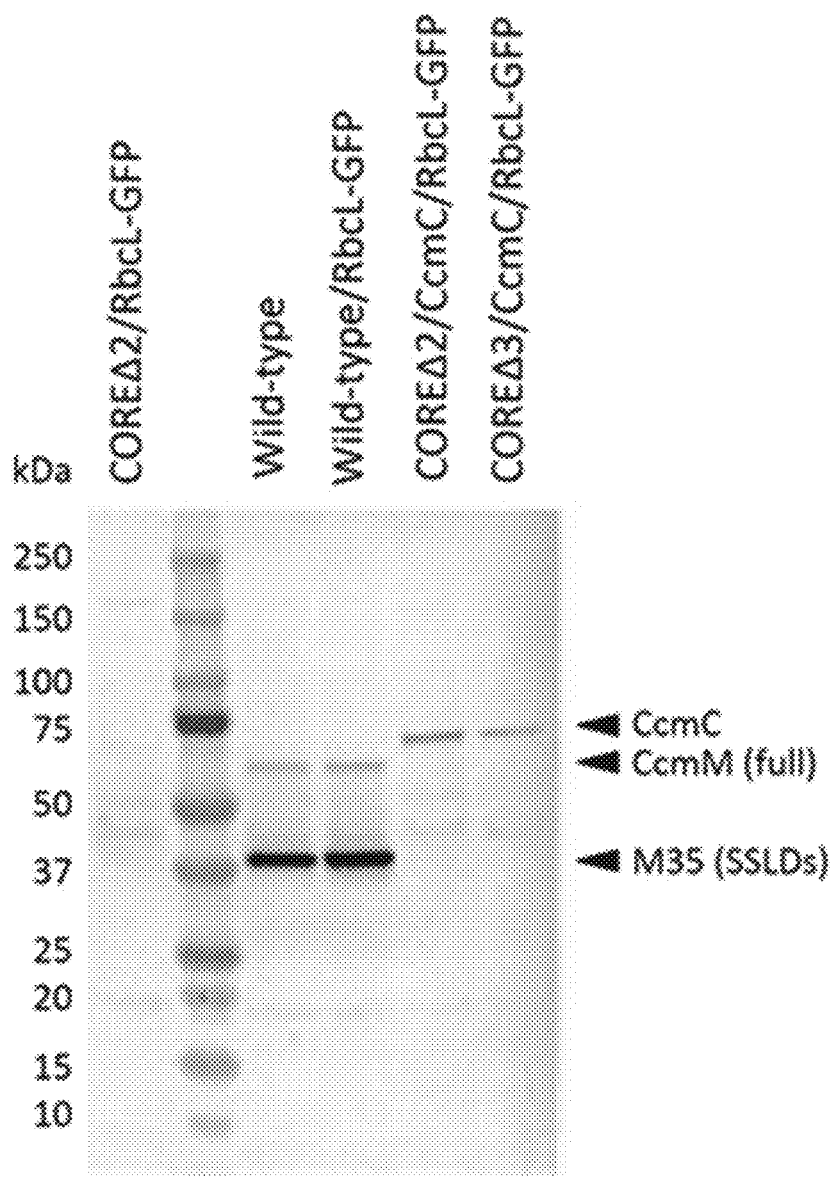
FIG. 2 illustrates cross-reactivity of the chimeric protein CcmC with anti-CcmM antibodies. Whole cell lysates were blotted and probed using anti-CcmM antibodies. Protein extracts from Controls (Wild-type background) show two bands corresponding to the full length and the short form of CcmM, while the mutants (CcmC background) show one band due to the cross-reactivity of the antibody with the small subunit-like domains.

Protein screening by immunoblot using polyclonal anti-CcmM antibodies showed no cross-reactivity with a total protein extract of the COREΔ2/RbcL-GFP strain, confirming the absence of those proteins (FIG. 2). In contrast, signals at ~37 kDa (major) and at ~63 kDa (minor) were observed in wild type and in the control strain expressing rbcL-GFP (hereafter Wild-type/RbcL-GFP strain), corresponding to the two forms of CcmM required for carboxysome assembly in Wild-type Syn 7942 carboxysomes (corresponding to M35 and full-length CcmM (So et al., 2002b; Long et al., 2010). These two bands are absent in the COREΔ2/CcmC/RbcL-GFP and COREΔ3/CcmC/RbcL-GFP strains, and replaced by cross-reactivity at ~75 kDa, corresponding to the fusion protein (predicted mass of 67 kDa; FIG. 2).

Example 3: CcmC Replaces Four Proteins of the β-Carboxysome Core

This Example illustrates assembly of CcmC into functioning carboxysomes.

Figure 3:
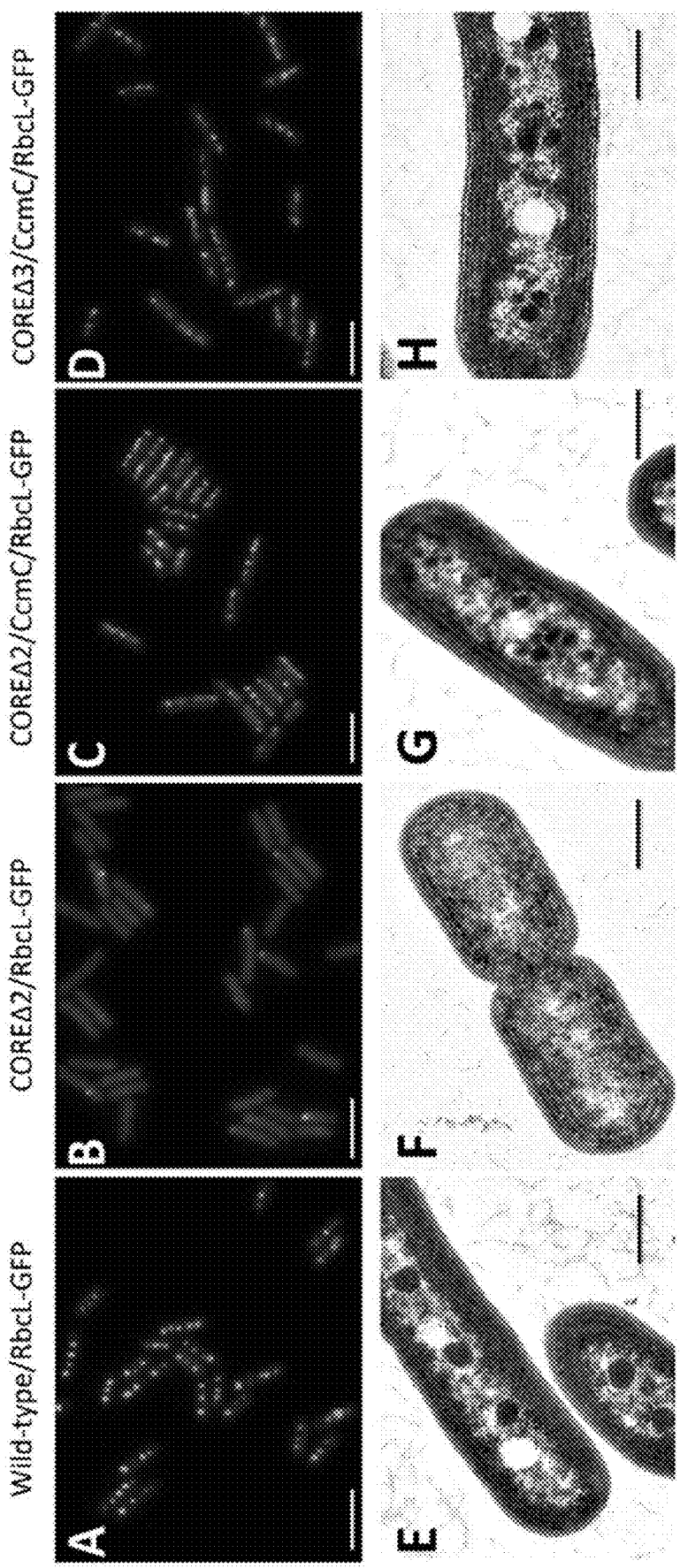
FIG. 3 illustrates structural complementation of the carboxysome core deletion strains with the chimeric protein CcmC.

Fluorescence and transmission electron microscopy were used to assay for formation of carboxysomes (FIG. 3). In the wild-type/RbcL-GFP strain, the carboxysomes were in the typical arrangement, along the longitudinal axes of the cells (FIG. 3 panel A). RbcL-GFP in the COREΔ2/RbcL-GFP strain was diffuse throughout the cell, as expected for strains lacking carboxysomes (Cameron et al., 2013) (FIG. 3 panel B). Occasional polar foci (n=150/556) were observed. Such polar foci may be due to misfolded and aggregated labeled protein. For example, polar localization of protein aggregates (Rokney et al., 2009) and false foci (Landgraf et al., 2012) have been observed in E. coli. Such foci may also be due to interaction with the remaining gene products of the carboxysome operon. They are not indicative of carboxysome formation, as the COREΔ2/RbcL-GFP strain has an her phenotype (i.e., a high $CO_2$-requiring phenotype).

In contrast, abundant GFP-labeled carboxysomes were observed in the mutant strains COREΔ2/CcmC/RbcL-GFP and COREΔ3/CcmC/RbcL-GFP (FIG. 3 panels C and D, respectively). Although occasionally clustered, the carboxysomes still localized along the longitudinal axis of the cell (FIG. 3 panels C and D, respectively).

The average carboxysome number (fluorescent puncta across the longitudinal plane) per cell in the wild-type/RbcL-GFP strain was 3.7±1.1 (FIG. 4A). The average carboxysome number was somewhat higher in the COREΔ2/CcmC/RbcL-GFP strain (average 6.4±1.8) and in the COREΔ3/CcmC/RbcL-GFP strain (average 6.4±2.0) (FIG. 4A).

The amount of Rubisco protein per mg Chlorophyll a (Chl a) protein in the different strains was compared by immunoblotting using antibodies against the large subunit RbcL. Both COREΔ2/CcmC/RbcL-GFP and COREΔ3/CcmC/RbcL-GFP strains contained more than a 2-fold increase in RbcL relative to the Wild-type/RbcL strain (FIG. 4B).

Analysis by transmission electron microscopy further confirmed carboxysome formation of native (FIG. 3 panel E) and streamlined carboxysomes (FIG. 3 panels G and H).

The chimeric carboxysomes were smaller than wild type carboxysomes. As illustrated in FIG. 4C, the average carboxysome diameter for wild-type/RbcL-GFP carboxysomes was 185±28 nm, but the average diameter of COREΔ2/CcmC carboxysomes was 103±25 nm and the average diameter of COREΔ3/CcmC carboxysomes was 95±19 nm. In addition, the CcmC strains typically had more carboxysomes and the CcmC carboxysomes tended to be more clustered compared to the wild-type carboxysomes.

Abnormally shaped carboxysomes were occasionally observed ("rod carboxysomes") in the CcmC strains but these have also been observed in wild type cyanobacteria (Gantt and Conti, 1969). Researchers have proposed that such rod carboxysomes may be a type of intermediate during carboxysome formation (Chen et al., 2013). Based on studies by the inventors, these rod carboxysomes could also be indicative of a deficiency in CA activity, as carboxysome aggregation and morphological variation were observed in the control strain ΔCcaA/RbcL-GFP (data not shown).

To determine if the reengineered carboxysomes function comparably to the Wild-type/RbcL-GFP carboxysomes, the growth of cells was analyzed at the exponential growth phase under high $CO_2$ (5%) and low $CO_2$ (air) conditions. No growth difference was observed between the strains when incubated in high $CO_2$(FIG. 5B), because under these conditions, cyanobacterial $CO_2$ fixation does not depend upon proper carboxysome formation. As expected, the COREΔ2/RbcL-GFP strain (without the CcmC construct) failed to grow in air, whereas in air the other strains were able to grow (FIG. 5A). The COREΔ2/CcmC/RbcL-GFP strain had the fastest doubling time among the reengineered strains tested, while the growth rates of COREΔ3/CcmC/RbcL-GFP and the Wild-type/RbcL-GFP strain are comparable (FIG. 5A-5B).

Example 4: Physiology of a Cyanobacterial Strain with a Streamlined Carboxysome

This Example illustrates some of the physiological characteristics of a triple deletion strain containing carboxysomes with synthetic cores (COREΔ3/CcmC/RbcL-GFP).

Figure 6A:
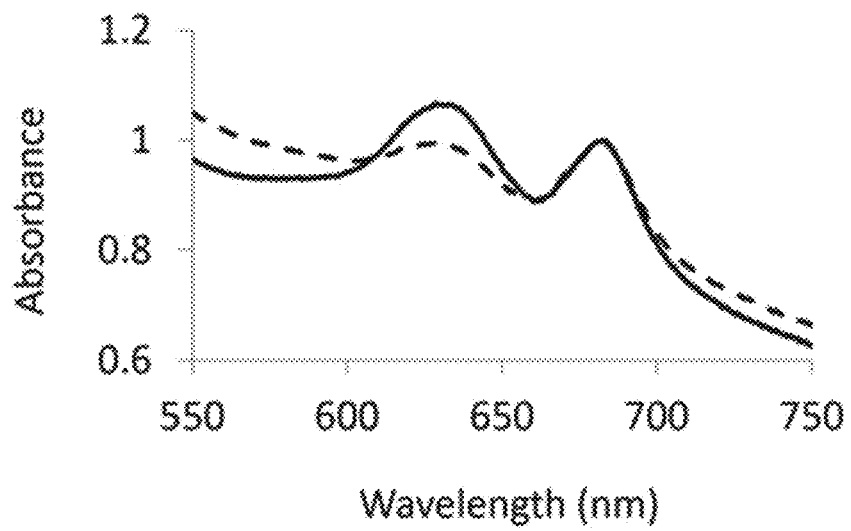
FIG. 6A-6C illustrate physiological parameters of wild-type vs. CcMC strains.

The COREΔ3/CcmC/RbcL-GFP strain has pigmentation differences when compared to Wild-type/RbcL-GFP (FIG. 6A). Such a difference could be attributed to decreased phycobilisome content.

The relative photosynthetic capacities of photosystem II were measure through quantification of chlorophyll fluorescence in dark adapted cells ($F_v/F_m$) upon transfer of the cultures from 3% $CO_2$ to air (FIG. 6B) The $F_v/F_m$ is widely used as a measure of the efficiency of the photosynthetic electron transport chain, which generates the ATP and reducing power that is consumed by the Calvin-Benson-Bassham (CBB) cycle (Baker, 2008). Accordingly, $F_v/F_m$ has been used as a proxy for carboxysome function. For example, carboxysome-deficient strains of Syn 7942 have an $F_v/F_m$ approximating zero in 3% $CO_2$(Cameron et al., 2013).

Figure 6B:
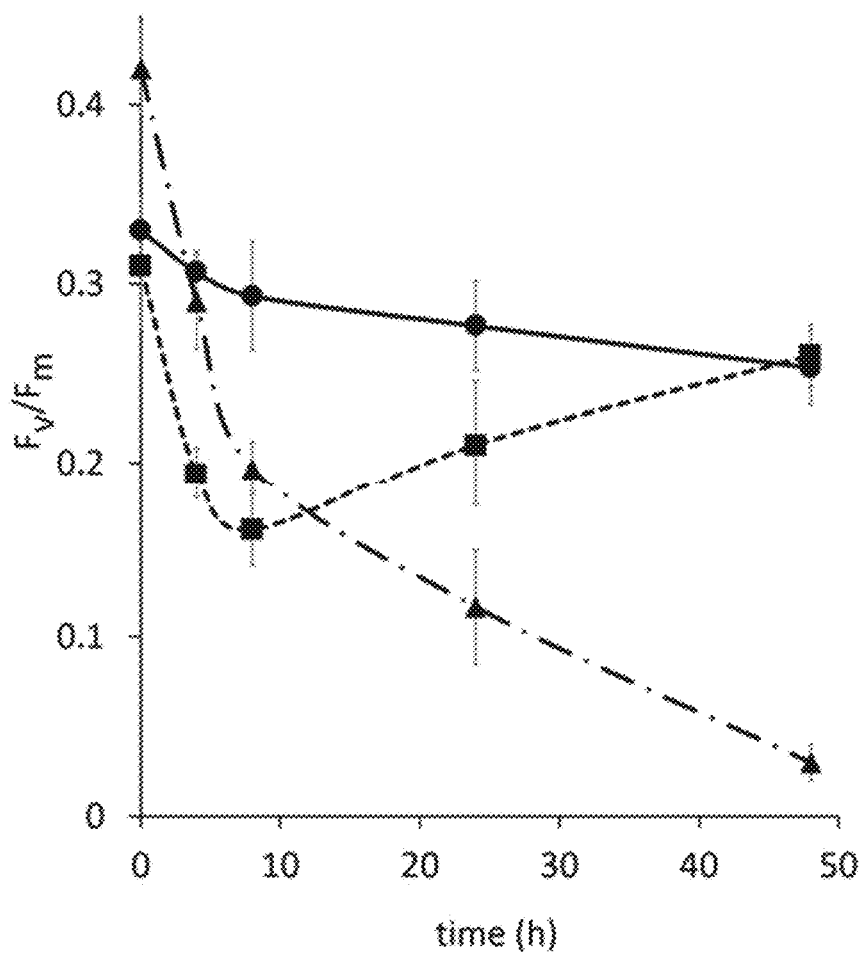

As illustrated in FIG. 6B, while the $F_v/F_m$ of Wild-type/RbcL-GFP remains relatively constant (solid line), a sharp decrease in $F_v/F_m$ relative to the high-$CO_2$ values is observed in both mutant core strains. The $F_v/F_m$ in the COREΔ2/RbcL-GFP control strain declined towards zero and did not recover (dashed, dotted line in FIG. 6B). However, the COREΔ3/CcmC/RbcL-GFP strain (dashed line in FIG. 6B) adapted within about 10 hr after the $CO_2$ step-down and eventually reached the same fluorescence levels as the wild-type/RbcL-GFP strain.

Figure 6C:
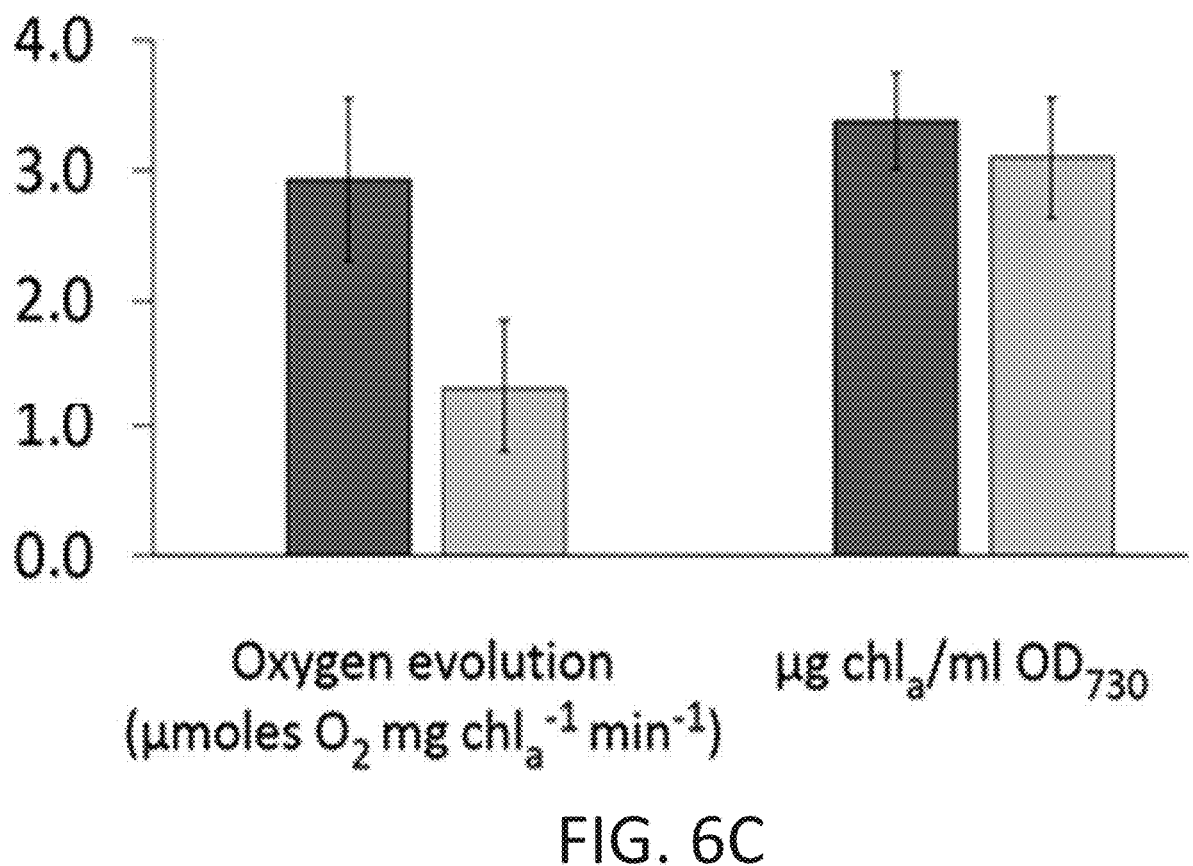

As an additional, complementary measure of photosynthetic activity, the oxygen evolution rates of air-grown cultures were compared at high light intensity (950 μmoles photons $m^{-2} s^{-1}$). As shown in FIG. 6C, the wild-type/RbcL-GFP cells (dark gray bar) produced more oxygen than the COREΔ3/CcmC/RbcL-GFP strain (light gray bar) The amounts of oxygen produced by the wild-type/RbcL-GFP cells was 2.9±1.0 μmoles $O_2$ μg $Chl_a^{-1}$ $min^{-1}$ compared to 1.3±0.5 μmoles $O_2$ μg $Chl_a^{-1}$ $min^{-1}$ for the COREΔ3/CcmC/RbcL-GFP.

These results indicate that the altered composition of the core has a net effect on the physiology of the cell relative to the Wild-type/RbcL-GFP control. Nevertheless, the reengineered core is immediately able to effectively support functional carboxysome assembly (FIG. 3 panels C and D) and photosynthesis (FIG. 5A-5B).

REFERENCES

Aussignargues, C., Paasch, B. C., Gonzalez-Esquer, R., Erbilgin, O., and Kerfeld, C. A. (2015). Bacterial microcompartment assembly: The key role of encapsulation peptides. *Communicative & Integrative Biology,* 8(3), e1039755.

Axen, S. D., Erbilgin, O., and Kerfeld, C. A (2014). A taxonomy of bacterial microcompartment loci constructed by a novel scoring method. PLoS Comput. Biol. 10, e1003898.

Baker, N. R. (2008). Chlorophyll fluorescence: A probe of photosynthesis in vivo. Annu. Rev. Plant Biol. 59, 89-113.

Biasini, M., Bienert, S., Waterhouse, A., Arnold, K., Studer, G., Schmidt, T., Kiefer, F., Cassarino, T. G., Bertoni, M., Bordoli, L., and Schwede, T. (2014). SWISS-MODEL: modelling protein tertiary and quaternary structure using evolutionary information. Nucleic Acids Res. 42, W252-W258.

Cai, F. Menon, B. B., Cannon, G. C., Curry, K. J., Shively, J. M., and Heinhorst, S. (2009). The pentameric vertex proteins are necessary for the icosahedral carboxysome shell to function as a $CO_2$ leakage barrier. PLoS ONE 4, e7521.

Cai, F., Dou, Z., Bernstein, S., Leverenz, R., Williams, E., Heinhorst, S., Shively, J., Cannon, G., and Kerfeld, C. (2015). Advances in understanding carboxysome assembly in *Prochlorococcus* and *Synechococcus* implicate CsoS2 as a critical component. Life 5, 1141-1171.

Cai, F., Bernstein, S. L., Wilson, S. C., & Kerfeld, C. A. (2016). Production and Characterization of Synthetic Carboxysome Shells with Incorporated Luminal Proteins. *Plant Physiology*, 170(3), 1868-1877.

Cameron, Jeffrey C., Wilson. Steven C., Bernstein, Susan L., and Kerfeld, Cheryl A. (2013). Biogenesis of a bacterial organelle: The carboxysome assembly pathway. Cell 155, 1131-1140.

Chen, A. H., Robinson-Mosher, A., Savage, D. F., Silver, P. A., and Polka, J. K. (2013). The bacterial carbon-fixing organelle is formed by shell envelopment of preassembled cargo. PLoS ONE 8, e76127.

Cheng, S., Liu, Y., Crowley, C. S., Yeates, T. O., and Bobik, T. A. (2008). Bacterial microcompartments: their properties and paradoxes. BioEssays 30, 1084-1095.

Dragosits, M., and Mattanovich, D. (2013). Adaptive laboratory evolution—principles and applications for biotechnology. Microb. Cell Fact. 12, 64.

Drews, G., and Niklowitz, W. (1956). [Cytology of Cyanophycea. II. Centroplasm and granular inclusions of *Phormidium uncinatum*]. Archiv fur Mikrobiologie 24, 147-162.

Frank, S., Lawrence, A. D., Prentice, M. B., and Warren, M. J. (2013). Bacterial microcompartments moving into a synthetic biological world. J. Biotechnol. 163, 273-279.

Gantt, E., and Conti, S. F. (1969). Ultrastructure of Blue-Green Algae. J. Bacteriol. 97, 1486-1493.

Hunter, S., Jone, P., Mitchell, A., Apweiler, R., Attwood, T. K., Bateman, A., Bernard, T., Binns, D., Bork, P., Burge, S., de Castro, E., Coggill, P., Corbett, M., Das, U., Daugherty, L., Duquenne, L., Finn, R. D., Fraser, M., Gough, J., Haft, D., Hulo, N., Kahn, D., Kelly, E., Letunic, I. Lonsdale, D., Lopez, R., Madera, M., Maslen, J., McAnulla, C., McDowall, J., McMenamin, C., Mi. H., Mutowo-Muellenet, P., Mulder, N., Natale, D., Orengo, C., Pesseat, S., Punta, M., Quinn, A. F. Rivoire, C., Sangrador-Vegas, A., Selengut, J. D., Sigrist, C. J., Scheremetjew, M., Tate, J., Thimmajanarthanan, M., Thomas, P. D., Wu, C. H., Yeats, C., and Yong, S. Y. (2012). InterPro in 2011: new developments in the family and domain prediction database. Nucleic Acids Res. 40, D306-312.

Kerfeld, C. A., and Erbilgin, O. (2015). Bacterial microcompartments and the modular construction of microbial metabolism. Trends Microbiol. 23, 22-34.

Kinney, J. N., Salmeen, A., Cai, F., and Kerfeld, C. A. (2012). Elucidating essential role of conserved carboxysomal protein CcmN reveals common feature of bacterial microcompartment assembly. J. Biol. Chem. 287, 17729-17736.

Kufryk, G. I., Sachet, M., Schmetterer, G., and Vermaas, W. F. (2002). Transformation of the cyanobacterium *Synechocystis* sp. PCC 6803 as a tool for genetic mapping: optimization of efficiency. FEMS Microbiol. Lett. 206, 215-219.

Lagarde, D., Beuf, L., and Vermaas, W. (2000). Increased production of zeaxanthin and other pigments by application of genetic engineering techniques to *Synechocystis* sp. Strain PCC 6803. Appl. Environ. Microbiol. 66, 64-72.

Landgraf, D., Okumus, B., Chien, P., Baker, T. A., and Paulsson, J. (2012). Segregation of molecules at cell division reveals native protein localization. Nat. Methods 9, 480-482.

Lawrence, A. D., Frank, S., Newnham, S., Lee, M. J., Brown, I. R., Xue, W.-F., Rowe, M. L., Mulvihill, D. P., Prentice, M. B., Howard, M. J., and Warren, M. J. (2014). Solution structure of a bacterial microcompartment targeting peptide and its application in the construction of an ethanol bioreactor. ACS Synth. Biol. 3, 454-465.

Lichtenthaler, H. K. (1987). Chlorophylls and carotenoids: Pigments of photosynthetic biomembranes. Methods Enzymol. 148, 350-382.

Lin, M. T., Occhialini, A., Andralojc, P. J., Parry, M. A. J., and Hanson, M. R. (2014a). A faster Rubisco with potential to increase photosynthesis in crops. Nature 513, 547-550.

Lin, M. T., Occhialini, A., Andralojc, P. J., Devonshire, J., Hines, K. M., Parry, M. A. J., and Hanson, M. R. (2014b). β-Carboxysomal proteins assemble into highly organized structures in *Nicotiana* chloroplasts. Plant J. 79, 1-12.

Lluch-Senar, M., Delgado, J., Chen, W. H., Lloréns-Rico, V., O'Reilly, F. J., Wodke, J. A., Unal, E. B., Yus, E., Martinez, S., Nichols, R. J., Ferrar, T., Vivancos, A., Schmeisky, A., Stiilke, J, van Noort, V., Gavin, A. C., Bork, P., and Serrano, L. (2015). Defining a minimal cell: essentiality of small ORFs and ncRNAs in a genome-reduced bacterium. Mol. Syst. Biol. 11, 780.

Long, B. M., Badger, M. R., Whitney, S. M., and Price, G. D. (2007). Analysis of carboxysomes from *Synechococcus* PCC7942 reveals multiple Rubisco complexes with carboxysomal proteins CcmM and CcaA. J. Biol. Chem. 282, 29323-29335.

Long, B. M., Tucker, L., Badger, M. R., and Price, G. D. (2010). Functional cyanobacterial β-carboxysomes have an absolute requirement for both long and short forms of the CcmM protein. Plant Physiol. 153, 285-293.

Marsh, Joseph A., Herndndez, H., Hall, Z., Ahnert, Sebastian E., Perica, T., Robinson, Carol V., and Teichmann, Sarah A. (2013). Protein complexes are under evolutionary selection to assemble via ordered pathways. Cell 153, 461-470.

Peña, K. L., Castel, S. E., de Araujo, C., Espie, G. S., and Kimber, M. S. (2010). Structural basis of the oxidative activation of the carboxysomal γ-carbonic anhydrase, CcmM. Proc. Natl. Acad. Sci. 107, 2455-2460.

Pettersen, E. F., Goddard, T. D., Huang, C. C., Couch, G. S., Greenblatt, D. M., Meng, E. C., and Ferrin, T. E. (2004). UCSF Chimera-A visualization system for exploratory research and analysis. J. Comput. Chem. 25, 1605-1612.

Price, G. D., and Badger, M. R. (1989). Isolation and characterization of high $CO_2$-requiring-mutants of the cyanobacterium *Synechococcus* PCC7942: Two phenotypes that accumulate inorganic carbon but are apparently unable to generate $CO_2$ within the carboxysome. Plant Physiol. 91, 514-525.

Price, G. D., Badger, M. R., Woodger, F. J., and Long, B. M. (2008). Advances in understanding the cyanobacterial $CO_2$-concentrating-mechanism (CCM): functional components, Ci transporters, diversity, genetic regulation and prospects for engineering into plants. J. Exp. Bot. 59, 1441-1461.

Price, G. D., Pengelly, J. J. L., Forster, B., Du, J., Whitney, S. M., von Caemmerer, S., Badger, M. R., Howitt, S. M., and Evans, J. R. (2013). The cyanobacterial CCM as a source of genes for improving photosynthetic CO$_2$ fixation in crop species. J. Exp. Bot. 64, 753-768.

Reynolds, E. S. (1963). The use of lead citrate at high pH as an electron-opaque stain in electron microscopy. J. Cell Biol. 17, 208-212.

Rippka, R., Deruelles, J., Waterbury, J. B., Herdman, M., and Stanier, R. Y. (1979). Generic assignments, strain histories and properties of pure cultures of cyanobacteria. J. Gen. Microbiol. 111, 1-61.

Rokney, A., Shagan, M., Kessel, M., Smith, Y., Rosenshine, I., and Oppenheim, A. B. (2009). *E. coli* transports aggregated proteins to the poles by a specific and energy-dependent process. J. Mol. Biol. 392, 589-601.

Sambrook, J. and Russell, D. W. (2001). Molecular cloning: a laboratory manual. (CSHL Press).

Savage, D. F., Afonso, B., Chen, A. H., and Silver, P. A. (2010). Spatially ordered dynamics of the bacterial carbon fixation machinery. Science 327, 1258-1261.

Schneider, C. A., Rasband, W. S., and Eliceiri, K. W. (2012). NIH Image to ImageJ: 25 years of image analysis. Nat. Methods 9, 671-675.

So, A. K.-C., Cot, S. S.-W., and Espie, G. S. (2002a). Characterization of the C-terminal extension of carboxysomal carbonic anhydrase from *Synechocystis* sp. PCC6803. Funct. Plant Biol. 29, 183-194.

So, A. K. C., John-McKay, M., and Espie, G. S. (2002b). Characterization of a mutant lacking carboxysomal carbonic anhydrase from the cyanobacterium *Synechocystis* PCC6803. Planta 214.456-467.

Takahashi, S., and Murata, N. (2005). Interruption of the Calvin cycle inhibits the repair of Photosystem II from photodamage. Biochim. Biophys. Acta 1708, 352-361.

Zarzycki, J., Axen, S. D., Kinney, J. N., and Kerfeld, C. A. (2013). Cyanobacterial-based approaches to improving photosynthesis in plants. J. Exp. Bot. 64, 787-798.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements

1. A fusion protein comprising at least two small subunit-like domains (SSLDs), at least one carbonic anhydrase (CA) domain, and at least one encapsulation peptide (EP).
2. The fusion protein of statement 1, wherein the at least one carbonic anhydrase (CA) domain is flanked on one side by the at least two small subunit-like domains (SSLDs), and by the at least one encapsulation peptide (EP) on the other side.
3. The fusion protein of statement 1 or 2, wherein the at least two small subunit-like domains (SSLDs) comprise scaffolding domains that can bind or nucleate with ribulose-1,5-bisphosphate carboxylase/oxygenase (Rubisco).
4. The fusion protein of statement 1, 2, or 3, wherein the at least two small subunit-like domains (SSLDs) can nucleate with ribulose-1,5-bisphosphate carboxylase/oxygenase (Rubisco), and the Rubisco can synthesize 3-phosphoglycerate (3-PGA).
5. The fusion protein of statement 1-3, or 4, wherein the at least two small subunit-like domains (SSLDs) comprise at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NOs:1-11, 37, 75, 76, or 77.
6. The fusion protein of statement 1-4 or 5, wherein the at least two small subunit-like domains (SSLDs) comprise at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NOs:5-11, 37, 75, 76, or 77.
7. The fusion protein of statement 1-5 or 6, wherein the at least one carbonic anhydrase domain converts bicarbonate to carbon dioxide.
8. The fusion protein of statement 1-6 or 7, wherein the at least one carbonic anhydrase domain comprises at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity with any of SEQ ID NOs:17-21 or 71.
9. The fusion protein of statement 1-7 or 8, wherein the at least one encapsulation peptide interacts with and/or binds one or more carboxysome shell protein.
10. The fusion protein of statement 1-8 or 9, wherein the at least one encapsulation peptide comprises at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NOs:12-16.
11. An expression cassette comprising a promoter operably linked to a nucleic acid segment encoding the fusion protein of statement 1-9 or 10.
12. The expression cassette of statement 11, wherein the promoter is a constitutive promoter, inducible promoter, regulated promoter, cell specific promoter, or synthetic promoter.
13. The expression cassette of statement 11 or 12, wherein the promoter is active before or during log phase growth of cells comprising the expression cassette.
14. The expression cassette of statement 11, 12, or 13, wherein the promoter is active after log phase growth of cells comprising the expression cassette.
15. The expression cassette of statement 11-13 or 14, wherein the nucleic acid segment encoding the fusion protein comprises at least 40% sequence identity, or at least 50% sequence identity, or at least 60% sequence identity, or at least 70% sequence identity, or at least 80% sequence identity, or at least 90% sequence identity, or at least 95% sequence identity, or at least 96% sequence identity, or at least 97% sequence identity, or at least 98% sequence identity, or at least 99% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NOs:26-29.
16. A cell comprising the expression cassette of statement 11-14 or 15.
17. An expression vector comprising the expression cassette of statement 11-14 or 15.
18. A cell comprising the expression vector of statement 16.
19. An organism comprising the fusion protein of statement 1-9 or 10.
20. An organism comprising a nucleic acid segment encoding the fusion protein of statement 1-9 or 10.
21. An organism comprising the expression cassette of statement 11-15, or the expression vector of statement 17.
22. A method comprising expressing the fusion protein of statement 1-9 or 10 in a cell.
23. A method comprising expressing the fusion protein of statement 1-9 or 10 from a nucleic acid in a cell.
24. A method comprising expressing the fusion protein of statement 1-9 or 10 from a heterologous nucleic acid in a cell.
25. A method comprising expressing a fusion protein encoded by the expression cassette of statement 11-14 or 15 in a cell.
26. A method for carbon fixation comprising expressing the fusion protein of statement 1-9 or 10 in a cell.
27. The method of statement 26, wherein the cell is a cyanobacteria, a bacteria, a plant cell, or an algae (e.g., a microalgae).
28. A method for carbon fixation comprising culturing a cell comprising the expression cassette of statement 11-14 or 15.
29. The method of statement 28, wherein the cell is a cyanobacteria, a bacteria, a plant cell, or an algae (e.g., a microalgae).
30. A method for oxygen evolution comprising culturing a cell comprising the expression cassette of statement 11-14 or 15.
31. A method comprising culturing a cell that can express the fusion protein of statement 1-9 or 10, and that can synthesize a product selected from a carbohydrate, sugar, protein, fatty acid, oil, biomass, alcohol, isobutyraldehyde, butanol, ethanol, propanediol, or isoprene.
32. The method of statement 31, wherein the cell is a cyanobacteria, a bacteria, a plant cell, or an algae (e.g., a microalgae).

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a plant" or "a seed" or "a cell" includes a plurality of such plants, seeds or cells, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:

1. A fusion protein comprising a polypeptide comprising at least one carbon dioxide concentrating mechanism (CcmM) protein comprising a sequence with at least 95% sequence identity to SEQ ID NO: 5, at least one carbonic anhydrase domain comprising a sequence with at least 95% sequence identity to SEQ ID NO: 17 and at least one encapsulation peptide domain comprising a sequence with at least 95% sequence identity to SEQ ID NO: 13.

2. The fusion protein of claim 1, wherein the at least one carbon dioxide concentrating mechanism (CcmM) protein has small subunit-like domains (SSLDs) that can bind or nucleate with ribulose-1,5-bisphosphate carboxylase/oxygenase (Rubisco), and the Rubisco can synthesize 3-phosphoglycerate (3-PGA).

3. The fusion protein of claim 1, wherein the at least one carbonic anhydrase domain converts bicarbonate to carbon dioxide.

4. The fusion protein of claim 1, wherein the at least one encapsulation peptide interacts with and/or binds one or more carboxysome shell protein.

\* \* \* \* \*

```
                        SEQUENCE LISTING

<160> NUMBER OF SEQ ID NOS: 77

<210> SEQ ID NO 1
<211> LENGTH: 539
<212> TYPE: PRT
<213> ORGANISM: Synechococcus elongatus

<400> SEQUENCE: 1

Met Pro Ser Pro Thr Thr Val Pro Val Ala Thr Ala Gly Arg Leu Ala
1               5                   10                  15

Glu Pro Tyr Ile Asp Pro Ala Ala Gln Val His Ala Ile Ala Ser Ile
                20                  25                  30

Ile Gly Asp Val Arg Ile Ala Ala Gly Val Arg Val Ala Ala Gly Val
            35                  40                  45

Ser Ile Arg Ala Asp Glu Gly Ala Pro Phe Gln Val Gly Lys Glu Ser
        50                  55                  60

Ile Leu Gln Glu Gly Ala Val Ile His Gly Leu Glu Tyr Gly Arg Val
65                  70                  75                  80

Leu Gly Asp Asp Gln Ala Asp Tyr Ser Val Trp Ile Gly Gln Arg Val
                85                  90                  95

Ala Ile Thr His Lys Ala Leu Ile His Gly Pro Ala Tyr Leu Gly Asp
                100                 105                 110

Asp Cys Phe Val Gly Phe Arg Ser Thr Val Phe Asn Ala Arg Val Gly
            115                 120                 125

Ala Gly Ser Val Ile Met Met His Ala Leu Val Gln Asp Val Glu Ile
130                 135                 140

Pro Pro Gly Arg Tyr Val Pro Ser Gly Ala Ile Ile Thr Thr Gln Gln
145                 150                 155                 160

Gln Ala Asp Arg Leu Pro Glu Val Arg Pro Glu Asp Arg Glu Phe Ala
                165                 170                 175

Arg His Ile Ile Gly Ser Pro Pro Val Ile Val Arg Ser Thr Pro Ala
                180                 185                 190

Ala Thr Ala Asp Phe His Ser Thr Pro Thr Pro Ser Pro Leu Arg Pro
            195                 200                 205

Ser Ser Ser Glu Ala Thr Thr Val Ser Ala Tyr Asn Gly Gln Gly Arg
        210                 215                 220

Leu Ser Ser Glu Val Ile Thr Gln Val Arg Ser Leu Leu Asn Gln Gly
225                 230                 235                 240

Tyr Arg Ile Gly Thr Glu His Ala Asp Lys Arg Arg Phe Arg Thr Ser
                245                 250                 255

Ser Trp Gln Pro Cys Ala Pro Ile Gln Ser Thr Asn Glu Arg Gln Val
                260                 265                 270

Leu Ser Glu Leu Glu Asn Cys Leu Ser Glu His Glu Gly Glu Tyr Val
            275                 280                 285

Arg Leu Leu Gly Ile Asp Thr Asn Thr Arg Ser Arg Val Phe Glu Ala
        290                 295                 300

Leu Ile Gln Arg Pro Asp Gly Ser Val Pro Glu Ser Leu Gly Ser Gln
305                 310                 315                 320

Pro Val Ala Val Ala Ser Gly Gly Arg Gln Ser Ser Tyr Ala Ser
                325                 330                 335
```

```
Val Ser Gly Asn Leu Ser Ala Glu Val Val Asn Lys Val Arg Asn Leu
            340                 345                 350

Leu Ala Gln Gly Tyr Arg Ile Gly Thr Glu His Ala Asp Lys Arg Arg
            355                 360                 365

Phe Arg Thr Ser Ser Trp Gln Ser Cys Ala Pro Ile Gln Ser Ser Asn
        370                 375                 380

Glu Arg Gln Val Leu Ala Glu Leu Glu Asn Cys Leu Ser Glu His Glu
385                 390                 395                 400

Gly Glu Tyr Val Arg Leu Leu Gly Ile Asp Thr Ala Ser Arg Ser Arg
                405                 410                 415

Val Phe Glu Ala Leu Ile Gln Asp Pro Gln Gly Pro Val Gly Ser Ala
            420                 425                 430

Lys Ala Ala Ala Pro Val Ser Ser Ala Thr Pro Ser Ser His Ser
            435                 440                 445

Tyr Thr Ser Asn Gly Ser Ser Ser Asp Val Ala Gly Gln Val Arg
            450                 455                 460

Gly Leu Leu Ala Gln Gly Tyr Arg Ile Ser Ala Glu Val Ala Asp Lys
465                 470                 475                 480

Arg Arg Phe Gln Thr Ser Ser Trp Gln Ser Leu Pro Ala Leu Ser Gly
                485                 490                 495

Gln Ser Glu Ala Thr Val Leu Pro Ala Leu Glu Ser Ile Leu Gln Glu
            500                 505                 510

His Lys Gly Lys Tyr Val Arg Leu Ile Gly Ile Asp Pro Ala Ala Arg
            515                 520                 525

Arg Arg Val Ala Glu Leu Leu Ile Gln Lys Pro
            530                 535

<210> SEQ ID NO 2
<211> LENGTH: 539
<212> TYPE: PRT
<213> ORGANISM: Synechococcus elongatus

<400> SEQUENCE: 2

Met Pro Ser Pro Thr Val Pro Val Ala Thr Ala Gly Arg Leu Ala
1               5                   10                  15

Glu Pro Tyr Ile Asp Pro Ala Ala Gln Val His Ala Ile Ala Ser Ile
                20                  25                  30

Ile Gly Asp Val Arg Ile Ala Ala Gly Val Arg Val Ala Ala Gly Val
            35                  40                  45

Ser Ile Arg Ala Asp Glu Gly Ala Pro Phe Gln Val Gly Lys Glu Ser
50                  55                  60

Ile Leu Gln Glu Gly Ala Val Ile His Gly Leu Glu Tyr Gly Arg Val
65                  70                  75                  80

Leu Gly Asp Asp Gln Ala Asp Tyr Ser Val Trp Ile Gly Gln Arg Val
            85                  90                  95

Ala Ile Thr His Lys Ala Leu Ile His Gly Pro Ala Tyr Leu Gly Asp
            100                 105                 110

Asp Cys Phe Val Gly Phe Arg Ser Thr Val Phe Asn Ala Arg Val Gly
            115                 120                 125

Ala Gly Ser Val Ile Met Met His Ala Leu Val Gln Asp Val Glu Ile
            130                 135                 140

Pro Pro Gly Arg Tyr Val Pro Ser Gly Ala Ile Ile Thr Thr Gln Gln
145                 150                 155                 160

Gln Ala Asp Arg Leu Pro Glu Val Arg Pro Glu Asp Arg Glu Phe Ala
```

165                 170                 175
Arg His Ile Ile Gly Ser Pro Val Ile Val Arg Ser Thr Pro Ala
                180                 185                 190

Ala Thr Ala Asp Phe His Ser Thr Pro Thr Pro Ser Pro Leu Arg Pro
            195                 200                 205

Ser Ser Ser Glu Ala Thr Thr Val Ser Ala Tyr Asn Gly Gln Gly Arg
        210                 215                 220

Leu Ser Ser Glu Val Ile Thr Gln Val Arg Ser Leu Leu Asn Gln Gly
225                 230                 235                 240

Tyr Arg Ile Gly Thr Glu His Ala Asp Lys Arg Arg Phe Arg Thr Ser
                245                 250                 255

Ser Trp Gln Pro Cys Ala Pro Ile Gln Ser Thr Asn Glu Arg Gln Val
            260                 265                 270

Leu Ser Glu Leu Glu Asn Cys Leu Ser Glu His Glu Gly Glu Tyr Val
        275                 280                 285

Arg Leu Leu Gly Ile Asp Thr Asn Thr Arg Ser Arg Val Phe Glu Ala
    290                 295                 300

Leu Ile Gln Arg Pro Asp Gly Ser Val Pro Glu Ser Leu Gly Ser Gln
305                 310                 315                 320

Pro Val Ala Val Ala Ser Gly Gly Arg Gln Ser Ser Tyr Ala Ser
                325                 330                 335

Val Ser Gly Asn Leu Ser Ala Glu Val Val Asn Lys Val Arg Asn Leu
            340                 345                 350

Leu Ala Gln Gly Tyr Arg Ile Gly Thr Glu His Ala Asp Lys Arg Arg
        355                 360                 365

Phe Arg Thr Ser Ser Trp Gln Ser Cys Ala Pro Ile Gln Ser Ser Asn
    370                 375                 380

Glu Arg Gln Val Leu Ala Glu Leu Glu Asn Cys Leu Ser Glu His Glu
385                 390                 395                 400

Gly Glu Tyr Val Arg Leu Leu Gly Ile Asp Thr Ala Ser Arg Ser Arg
                405                 410                 415

Val Phe Glu Ala Leu Ile Gln Asp Pro Gln Gly Pro Val Gly Ser Ala
            420                 425                 430

Lys Ala Ala Ala Pro Val Ser Ser Ala Thr Pro Ser Ser His Ser
        435                 440                 445

Tyr Thr Ser Asn Gly Ser Ser Ser Asp Val Ala Gly Gln Val Arg
    450                 455                 460

Gly Leu Leu Ala Gln Gly Tyr Arg Ile Ser Ala Glu Val Ala Asp Lys
465                 470                 475                 480

Arg Arg Phe Gln Thr Ser Ser Trp Gln Ser Leu Pro Ala Leu Ser Gly
                485                 490                 495

Arg Ser Glu Ala Thr Val Leu Pro Ala Leu Glu Ser Ile Leu Gln Glu
            500                 505                 510

His Lys Gly Lys Tyr Val Arg Leu Ile Gly Ile Asp Pro Ala Ala Arg
        515                 520                 525

Arg Arg Val Ala Glu Leu Leu Ile Gln Lys Pro
    530                 535

<210> SEQ ID NO 3
<211> LENGTH: 566
<212> TYPE: PRT
<213> ORGANISM: Prochlorothrix hollandica

<400> SEQUENCE: 3

-continued

```
Met Ala Gly Tyr Ser Ser Ala Ala Pro Pro Thr Pro Trp Ser Arg Gly
 1               5                  10                  15

Leu Ala Glu Pro Gln Ile Asp Gly Ser Ala Tyr Val His Ala Phe Ser
             20                  25                  30

Asn Val Ile Gly Asp Val Trp Ile Gly Glu Asn Val Leu Ile Ala Pro
         35                  40                  45

Gly Thr Ser Ile Arg Ala Asp Glu Gly Ala Pro Phe His Ile Gly Ser
     50                  55                  60

Ser Thr Asn Ile Gln Asp Gly Val Val Ile His Gly Leu Glu Gln Gly
65                  70                  75                  80

Arg Val Leu Gly Asp Asp Gln Lys Glu Tyr Ser Val Trp Val Gly Arg
                 85                  90                  95

Asp Ser Ser Leu Thr His Lys Ala Leu Ile His Gly Pro Ala Tyr Val
            100                 105                 110

Gly Asp Glu Cys Phe Ile Gly Phe Arg Ser Thr Val Phe Asn Ala Arg
        115                 120                 125

Val Gly His Gly Cys Ile Val Met Met His Ala Leu Ile Gln Asp Val
    130                 135                 140

Glu Ile Pro Pro Gly Lys Tyr Val Pro Ser Gly Ala Ile Ile Thr Ser
145                 150                 155                 160

Gln Gln Gln Ala Asp Arg Leu Pro Asp Val Arg Gln Glu Asp Lys Asp
                165                 170                 175

Phe Ala His His Val Val Gly Ile Asn Glu Ala Leu Leu Ala Gly Tyr
            180                 185                 190

His Cys Ala Arg Ser Ser Ala Cys Ile Asn Pro Ile Arg Ala Gly Leu
        195                 200                 205

Ser Gln Thr Phe Gln Gly Ser Thr Pro Gly Thr His Gly Leu Glu Glu
    210                 215                 220

Ser Ile Asn Gly Thr Thr Asn Thr Met Asn Asn Gly Tyr Gly Leu Ser
225                 230                 235                 240

Pro Ala Leu Ile Ser Gln Val Arg Ser Leu Leu Ala Gln Gly Tyr Arg
                245                 250                 255

Ile Gly Thr Glu His Ala Thr Pro Arg Arg Phe Lys Thr Ser Ser Trp
            260                 265                 270

Glu Ser Cys Ala Pro Ile Glu Ser Lys Asn Glu Gly Gln Val Leu Ser
        275                 280                 285

Ala Leu Ser Gly Cys Leu Gln Glu His Gln Gly Glu Tyr Val Arg Leu
    290                 295                 300

Leu Gly Ile Asp Val Gln Ala Arg Arg Val Leu Glu Val Leu Ile
305                 310                 315                 320

Gln Arg Pro Asp Gly Lys Pro Thr Ser Leu Ser Thr Arg Gly Thr Val
                325                 330                 335

Ser Val Ala Ala Pro Ser Ala Ser Asn Gly His Arg Ser Ser Thr Ala
            340                 345                 350

Gly Thr Ser Asn Gly Gly Gly Ser Leu Ala Asp Gln Val Arg Gly Leu
        355                 360                 365

Leu Gln Gln Gly Cys Arg Ile Thr Thr Glu His Ala Asp Lys Arg Arg
    370                 375                 380

Phe Lys Thr Ser Ser Trp Gln Val Gly Ala Val Ile Glu Ser Ser Asn
385                 390                 395                 400

Phe Asn Gln Val Met Ala Ala Leu Asp Ser Ala Met Gln Gln Tyr Ser
                405                 410                 415

Gly Glu Tyr Val Arg Leu Ile Ala Val Asp Pro Leu Ala Lys Arg Arg
```

```
                420             425             430
Val Ala Glu Val Leu Ile His Arg Pro Asp Gly Lys Pro Val Ala Thr
            435                 440                 445
Thr Ala Ala Ser Lys Gly Ser Thr Tyr Ser Ser Asn Gly Ala Ser Asn
        450                 455                 460
Gly Ala Ser Asn Gly Ala Ser Ser Asn Gly Tyr Gly Gly Gly Ser Val
465                 470                 475                 480
Ser Gly Leu Ser Gly Glu Thr Ala Asn Gln Val Arg Gly Trp Leu Gly
                485                 490                 495
Gln Gly Tyr Arg Ile Ser Ala Glu Tyr Ala Asp Lys Arg Arg Phe Lys
            500                 505                 510
Thr Gly Ser Trp Gln Thr His Gly Thr Leu Glu Gly Arg Gly Asp Gln
        515                 520                 525
Val Leu Gly Ser Ile Ser Thr Val Leu Ser Thr His Ser Gly Asn Tyr
        530                 535                 540
Val Arg Leu Val Gly Val Asp Pro Gln Ala Lys Arg Arg Val Gly Gln
545                 550                 555                 560
Val Ile Ile Gln Arg Pro
                565
```

<210> SEQ ID NO 4
<211> LENGTH: 661
<212> TYPE: PRT
<213> ORGANISM: Hassallia byssoidea

<400> SEQUENCE: 4

```
Met Ala Val Arg Ser Thr Ala Ala Pro Pro Thr Pro Trp Ser Arg Asn
1               5                   10                  15
Leu Ala Glu Pro Asn Ile Asp Ala Thr Ala Tyr Ile His Pro Phe Ser
            20                  25                  30
Asn Val Ile Gly Asp Val Arg Ile Gly Ala Asn Val Ile Val Ala Pro
        35                  40                  45
Gly Thr Ser Ile Arg Ala Asp Glu Gly Thr Pro Phe Asn Ile Ser Glu
    50                  55                  60
Asn Thr Asn Leu Gln Asp Gly Val Val Ile His Gly Leu Glu Gln Gly
65                  70                  75                  80
Arg Val Ile Gly Asp Asp Asn Gln Tyr Ser Val Trp Ile Gly Lys
                85                  90                  95
Asn Ala Ser Ile Thr His Met Ala Leu Ile His Gly Pro Ala Tyr Val
                100                 105                 110
Gly Asp Asp Cys Phe Ile Gly Phe Arg Ser Thr Val Phe Asn Ala Arg
            115                 120                 125
Val Gly Asn Gly Cys Ile Val Met Met His Ala Leu Ile Gln Asp Val
        130                 135                 140
Glu Ile Pro Pro Gly Lys Tyr Val Pro Ser Gly Ala Ile Ile Thr Asn
145                 150                 155                 160
Gln Gln Gln Ala Asp Arg Leu Pro Asp Val Gln Val Gln Asp Arg Glu
                165                 170                 175
Phe Ser His His Val Val Gly Ile Asn Gln Ala Leu Arg Ser Gly Tyr
            180                 185                 190
Leu Cys Ala Ala Asp Asn Lys Cys Ile Lys Asn Ile Arg Asn Glu Met
        195                 200                 205
Thr Ser Ser Tyr Lys Thr Asn Gly Ser Asn Gly Tyr Ser Gly Asn Gly
    210                 215                 220
```

```
Ser Val Ser Ser Asn Leu Ser Ser Glu Thr Val Gln Gln Val Arg His
225                 230                 235                 240

Leu Leu Glu Gln Gly Tyr Gln Ile Gly Thr Glu His Val Asp Gln Arg
            245                 250                 255

Arg Phe Arg Thr Gly Ser Trp Ala Ser Cys Ser Pro Ile Ala Thr Asn
            260                 265                 270

Ser Thr Ser Glu Ala Ile Ala Ala Leu Glu Ser Cys Leu Ala Glu His
        275                 280                 285

Ser Gly Glu Phe Val Arg Leu Phe Gly Ile Asp Pro Lys Gly Lys Arg
    290                 295                 300

Arg Val Leu Glu Thr Ile Ile Gln Arg Pro Asp Gly Val Val Gln Asn
305                 310                 315                 320

Gly Thr Thr Pro Lys Leu Gly Val Lys Ser Ala Ser Tyr Ser Gly Gly
                325                 330                 335

Asn Ser Tyr Ser Gly Ser Ser Thr Leu Ser Gly Glu Ala Ile Glu Gln
            340                 345                 350

Val Arg Gln Leu Leu Ala Gly Gly Tyr Lys Ile Gly Met Glu His Val
        355                 360                 365

Asp Lys Arg Arg Phe Arg Thr Gly Ser Trp Gln Ser Cys Thr Pro Ile
    370                 375                 380

Ala Ser Ser Asn Glu Lys Glu Val Ile Ser Ala Leu Glu Ala Cys Val
385                 390                 395                 400

Ala Ser His Thr Gly Glu Tyr Val Arg Leu Val Gly Ile Glu Pro Lys
                405                 410                 415

Ala Arg Lys Arg Val Leu Glu Ser Ile Ile Gln Arg Pro Asp Gly Asn
            420                 425                 430

Val Ala Glu Gly Ser Ser Asn Lys Phe Val Ala Ser Ser Ser Ser Glu
        435                 440                 445

Ser Arg Thr Ser Thr Asn Ala Ser Thr Arg Leu Ser Pro Glu Val Ile
    450                 455                 460

Asp Gln Leu Arg Gln Leu Ile Asn Gln Gly Ser Lys Ile Ser Ala Glu
465                 470                 475                 480

His Val Asp Lys Arg Arg Phe Arg Thr Gly Ser Trp Ala Ser Cys Gly
                485                 490                 495

Gln Ile Gln Gly Asn Ser Glu Arg Glu Ala Ile Ala Ala Leu Glu Gly
            500                 505                 510

Tyr Leu Arg Glu Tyr Gln Gly Glu Tyr Val Arg Leu Ile Gly Ile Glu
        515                 520                 525

Pro Lys Ala Lys Lys Arg Val Leu Glu Ser Ile Ile Gln Arg Pro Asp
    530                 535                 540

Asp Ser Val Ala Gln Ser Ser Arg Ser Asp Asn Gln Val Val Ala Ser
545                 550                 555                 560

Ser Ser Ser Ser Thr Ser Lys Thr Ser Asn Thr Ala Thr Ser Thr Arg
                565                 570                 575

Leu Ser Ser Glu Val Val Asp Gln Leu Arg Gln Leu Arg Asn Gln Gly
            580                 585                 590

Ser Lys Ile Ser Val Glu His Val Asp Gln Arg Arg Phe Arg Thr Gly
        595                 600                 605

Ser Trp Thr Ser Gly Gly Gln Ile Gln Gly Asn Ser Glu Arg Glu Ala
    610                 615                 620

Ile Ala Ala Leu Glu Gly Tyr Leu Arg Glu Tyr Glu Gly Glu Tyr Val
625                 630                 635                 640

Arg Leu Ile Gly Ile Asn Pro Lys Asp Lys Arg Arg Val Leu Glu Thr
```

-continued

```
                    645                 650                 655

Ile Ile Gln Arg Pro
            660

<210> SEQ ID NO 5
<211> LENGTH: 325
<212> TYPE: PRT
<213> ORGANISM: Synechococcus elongatus

<400> SEQUENCE: 5

Thr Val Ser Ala Tyr Asn Gly Gln Gly Arg Leu Ser Glu Val Ile
1               5                   10                  15

Thr Gln Val Arg Ser Leu Leu Asn Gln Gly Tyr Arg Ile Gly Thr Glu
                20                  25                  30

His Ala Asp Lys Arg Arg Phe Arg Thr Ser Ser Trp Gln Pro Cys Ala
            35                  40                  45

Pro Ile Gln Ser Thr Asn Glu Arg Gln Val Leu Ser Glu Leu Glu Asn
    50                  55                  60

Cys Leu Ser Glu His Glu Gly Glu Tyr Val Arg Leu Leu Gly Ile Asp
65                  70                  75                  80

Thr Asn Thr Arg Ser Arg Val Phe Glu Ala Leu Ile Gln Arg Pro Asp
                85                  90                  95

Gly Ser Val Pro Glu Ser Leu Gly Ser Gln Pro Val Ala Val Ala Ser
            100                 105                 110

Gly Gly Gly Arg Gln Ser Ser Tyr Ala Ser Val Ser Gly Asn Leu Ser
        115                 120                 125

Ala Glu Val Val Asn Lys Val Arg Asn Leu Leu Ala Gln Gly Tyr Arg
    130                 135                 140

Ile Gly Thr Glu His Ala Asp Lys Arg Arg Phe Arg Thr Ser Ser Trp
145                 150                 155                 160

Gln Ser Cys Ala Pro Ile Gln Ser Ser Asn Glu Arg Gln Val Leu Ala
                165                 170                 175

Glu Leu Glu Asn Cys Leu Ser Glu His Glu Gly Glu Tyr Val Arg Leu
            180                 185                 190

Leu Gly Ile Asp Thr Ala Ser Arg Ser Arg Val Phe Glu Ala Leu Ile
        195                 200                 205

Gln Asp Pro Gln Gly Pro Val Gly Ser Ala Lys Ala Ala Ala Pro
    210                 215                 220

Val Ser Ser Ala Thr Pro Ser Ser His Ser Tyr Thr Ser Asn Gly Ser
225                 230                 235                 240

Ser Ser Ser Asp Val Ala Gly Gln Val Arg Gly Leu Leu Ala Gln Gly
                245                 250                 255

Tyr Arg Ile Ser Ala Glu Val Ala Asp Lys Arg Arg Phe Gln Thr Ser
            260                 265                 270

Ser Trp Gln Ser Leu Pro Ala Leu Ser Gly Gln Ser Glu Ala Thr Val
        275                 280                 285

Leu Pro Ala Leu Glu Ser Ile Leu Gln Glu His Lys Gly Lys Tyr Val
    290                 295                 300

Arg Leu Ile Gly Ile Asp Pro Ala Ala Arg Arg Val Ala Glu Leu
305                 310                 315                 320

Leu Ile Gln Lys Pro
                325

<210> SEQ ID NO 6
<211> LENGTH: 803
```

<212> TYPE: PRT
<213> ORGANISM: Acaryochloris marina

<400> SEQUENCE: 6

```
Met Val Ile His Ser Pro Ser Thr Ser Ala Ser Met Gln Ala Gly Asn
1               5                   10                  15

Leu Pro Asp Pro Arg Val Ser Ser Ala Tyr Val His Ser Phe Ala
            20                  25                  30

Lys Val Met Gly Asp Val His Val Gly Ala Asn Ala Leu Ile Ala Pro
            35                  40                  45

Gly Ser Thr Ile Gln Ala Asp Gln Gly Leu Pro Phe His Ile Gly Asp
        50                  55                  60

Asn Val Asn Ile Gln Asp Gly Ala Val Ile His Ala Ile Glu Pro Gly
65                  70                  75                  80

Gln Val Arg Gly Lys Asp Gly Gln Asn Tyr Ala Val Trp Ile Gly Asn
                85                  90                  95

Asn Ser Cys Val Thr His Met Ala Leu Ile His Gly Pro Ala Phe Ile
                100                 105                 110

Gly Asp Asn Cys Phe Ile Gly Phe Arg Ser Thr Val Phe Asn Ala Lys
            115                 120                 125

Val Gly Asp Asn Cys Val Ile Met Met His Ala Leu Ile Gln Gly Val
130                 135                 140

Glu Ile Pro Pro Gly Lys Tyr Val Pro Ser Gly Ala Val Ile Thr Lys
145                 150                 155                 160

Gln Glu Gln Ala Asn Leu Leu Pro Asp Val Leu Glu Ser Asp Arg Lys
                165                 170                 175

Phe Thr Gln Gln Ile Ile His Val Asn Glu Ala Leu Lys Ser Glu Ile
            180                 185                 190

Ser Gly Ala Ser Thr Lys Thr Ser Ile Arg Pro Ala Arg Ala Asn Ile
        195                 200                 205

Gly His Ser Gln Ser His Arg Phe Thr Thr Asp Thr Lys Pro Met Asn
    210                 215                 220

His Thr Thr Leu Asp Ala Ala Ile Val Ser Gln Val Arg Ser Leu Leu
225                 230                 235                 240

Ala Gln Gly Tyr Arg Ile Gly Ser Glu His Ala Asp Lys Arg Arg Phe
                245                 250                 255

Gln Thr Ser Ser Trp Gln Ser Cys Pro Ser Ile Thr Ser Thr Asn Glu
            260                 265                 270

Ser Gln Val Leu Ala Gly Ile Glu Ser Cys Met Ser Glu His Gln Gly
        275                 280                 285

Glu Tyr Val Arg Leu Ile Gly Ile Asp Thr Gln Ala Arg Gln Arg Val
    290                 295                 300

Leu Glu Thr Ile Ile Gln Arg Pro Asp Gly Pro Val Lys Ser Ala Ser
305                 310                 315                 320

Ile Ser Ser Val Thr Lys Thr Ile Lys Asn Tyr Thr Thr Ser His Ile
                325                 330                 335

Ser Ser Ser Gly Asn Ile Asp Ala Glu Thr Ile Ala His Val Arg Ser
            340                 345                 350

Leu Leu Gly Gln Gly Tyr Arg Ile Gly Thr Glu His Ala Asp Ala Arg
        355                 360                 365

Arg Phe Gln Thr Ser Ser Trp Gln Ser Cys Ser Pro Ile Ala Ser Gln
    370                 375                 380

Gln Glu Ser Gln Val Val Ala Ala Leu Glu Ala Cys Ile Val Glu His
385                 390                 395                 400
```

```
Gln Gly Glu Tyr Val Arg Met Leu Gly Ile Asp Thr Gln Ala Lys Gln
                405                 410                 415
Arg Val Phe Glu Ala Ile Ile Gln Arg Pro Ser Asp Lys Pro Lys Ala
            420                 425                 430
Ala Pro Lys Ala Ser Arg Pro Ala Ser Thr Ser Ser Ser Ser Ser Ser
        435                 440                 445
Tyr Ala Ser Pro Ser Tyr Ala Ser Ser Ser Pro Asn Ser Gly Thr Ser
    450                 455                 460
Thr Gly Leu Gly Ala Asp Ala Ile Ala Gln Val Arg Ser Leu Leu Ala
465                 470                 475                 480
Gln Gly Tyr Arg Val Gly Tyr Glu Tyr Ala Asp Lys Arg Arg Phe Gln
                485                 490                 495
Thr Ser Ser Trp Gln Ser Cys Thr Pro Ile Asn Ser Gln Gln Glu Ser
            500                 505                 510
Gln Val Ile Ala Ala Leu Glu Ser Cys Ile Ala Glu His Pro Gly Asn
        515                 520                 525
Tyr Val Arg Leu Ile Gly Ile Asp Pro Lys Ala Lys Arg Arg Val Leu
    530                 535                 540
Glu Val Ile Ile Gln Arg Pro Asp Ser Asn Ser Lys Ala Ser Pro Ser
545                 550                 555                 560
Ala Pro Lys Ala Arg Pro Ala Ser Ser Ser Ser Tyr Ser Ser Lys
                565                 570                 575
Val Glu Ser Asn Ser Ser Ser Tyr Arg Pro Ala Pro Ser Ala Gly Leu
            580                 585                 590
Asp Gly Thr Val Val Asn Gln Ile Arg Ser Leu Leu Ala Gln Gly Tyr
        595                 600                 605
Arg Ile Gly Thr Glu Tyr Ala Asp Lys Arg Arg Phe Gln Thr Ser Ser
    610                 615                 620
Trp Gln Ser Cys Thr Pro Ile Ala Ser Gln Gln Glu Ser Gln Val Ile
625                 630                 635                 640
Ala Gly Val Glu Ala Cys Met Ala Glu His Pro Asn Asp Tyr Val Arg
                645                 650                 655
Leu Ile Gly Ile Asp Lys Arg Ala Lys Arg Arg Met Ser Glu Thr Ile
            660                 665                 670
Ile Gln Arg Pro Gly Gly Ser Thr Ala Thr Ser Ser Ser Val Lys Thr
        675                 680                 685
Ser Ser Ser Arg Ser Tyr Gln Ala Pro Ala Ala Lys Ser Ser Arg Gly
    690                 695                 700
Arg Gly Phe Ser Pro Arg Asn Gly Gly Ser Leu Asp Ala Asp Thr Val
705                 710                 715                 720
Ala Gln Val Arg Ser Leu Leu Ala Gln Gly Tyr Arg Ile Ser Thr Glu
                725                 730                 735
Tyr Ala Asp Lys Arg Arg Phe Gln Thr Ser Ser Trp Gln Ser Cys Pro
            740                 745                 750
Pro Ile Lys Thr Gln Gln Glu Ser Gln Val Ile Ala Ala Leu Glu Ser
        755                 760                 765
Cys Met Ala Asp His Gln Lys Glu Tyr Val Arg Leu Ile Gly Ile Asp
    770                 775                 780
Thr Asn Ala Lys Arg Arg Val Leu Glu Ser Val Ile Gln Lys Pro Val
785                 790                 795                 800
Ala Ala His
```

```
<210> SEQ ID NO 7
<211> LENGTH: 583
<212> TYPE: PRT
<213> ORGANISM: Acaryochloris marina

<400> SEQUENCE: 7
```

Lys Pro Met Asn His Thr Thr Leu Asp Ala Ala Ile Val Ser Gln Val
1               5                   10                  15

Arg Ser Leu Leu Ala Gln Gly Tyr Arg Ile Gly Ser Glu His Ala Asp
            20                  25                  30

Lys Arg Arg Phe Gln Thr Ser Ser Trp Gln Ser Cys Pro Ser Ile Thr
        35                  40                  45

Ser Thr Asn Glu Ser Gln Val Leu Ala Gly Ile Glu Ser Cys Met Ser
    50                  55                  60

Glu His Gln Gly Glu Tyr Val Arg Leu Ile Gly Ile Asp Thr Gln Ala
65                  70                  75                  80

Arg Gln Arg Val Leu Glu Thr Ile Ile Gln Arg Pro Asp Gly Pro Val
                85                  90                  95

Lys Ser Ala Ser Ile Ser Ser Val Thr Lys Thr Ile Lys Asn Tyr Thr
            100                 105                 110

Thr Ser His Ile Ser Ser Ser Gly Asn Ile Asp Ala Glu Thr Ile Ala
        115                 120                 125

His Val Arg Ser Leu Leu Gly Gln Gly Tyr Arg Ile Gly Thr Glu His
    130                 135                 140

Ala Asp Ala Arg Arg Phe Gln Thr Ser Ser Trp Gln Ser Cys Ser Pro
145                 150                 155                 160

Ile Ala Ser Gln Gln Glu Ser Gln Val Val Ala Ala Leu Glu Ala Cys
                165                 170                 175

Ile Val Glu His Gln Gly Glu Tyr Val Arg Met Leu Gly Ile Asp Thr
            180                 185                 190

Gln Ala Lys Gln Arg Val Phe Glu Ala Ile Ile Gln Arg Pro Ser Asp
        195                 200                 205

Lys Pro Lys Ala Ala Pro Lys Ala Ser Arg Pro Ala Ser Thr Ser Ser
    210                 215                 220

Ser Ser Ser Ser Tyr Ala Ser Pro Ser Tyr Ala Ser Ser Pro Asn
225                 230                 235                 240

Ser Gly Thr Ser Thr Gly Leu Gly Ala Asp Ala Ile Ala Gln Val Arg
                245                 250                 255

Ser Leu Leu Ala Gln Gly Tyr Arg Val Gly Tyr Glu Tyr Ala Asp Lys
            260                 265                 270

Arg Arg Phe Gln Thr Ser Ser Trp Gln Ser Cys Thr Pro Ile Asn Ser
        275                 280                 285

Gln Gln Glu Ser Gln Val Ile Ala Ala Leu Glu Ser Cys Ile Ala Glu
    290                 295                 300

His Pro Gly Asn Tyr Val Arg Leu Ile Gly Ile Asp Pro Lys Ala Lys
305                 310                 315                 320

Arg Arg Val Leu Glu Val Ile Ile Gln Arg Pro Asp Ser Asn Ser Lys
                325                 330                 335

Ala Ser Pro Ser Ala Pro Lys Ala Arg Pro Ala Ser Ser Ser Ser Ser
            340                 345                 350

Tyr Ser Ser Lys Val Glu Ser Asn Ser Ser Tyr Arg Pro Ala Pro
        355                 360                 365

Ser Ala Gly Leu Asp Gly Thr Val Val Asn Gln Ile Arg Ser Leu Leu
    370                 375                 380

```
Ala Gln Gly Tyr Arg Ile Gly Thr Glu Tyr Ala Asp Lys Arg Arg Phe
385                 390                 395                 400

Gln Thr Ser Ser Trp Gln Ser Cys Thr Pro Ile Ala Ser Gln Gln Glu
            405                 410                 415

Ser Gln Val Ile Ala Gly Val Glu Ala Cys Met Ala Glu His Pro Asn
        420                 425                 430

Asp Tyr Val Arg Leu Ile Gly Ile Asp Lys Arg Ala Lys Arg Arg Met
    435                 440                 445

Ser Glu Thr Ile Ile Gln Arg Pro Gly Gly Ser Thr Ala Thr Ser Ser
450                 455                 460

Ser Val Lys Thr Ser Ser Arg Ser Tyr Gln Ala Pro Ala Ala Lys
465                 470                 475                 480

Ser Ser Arg Gly Arg Gly Phe Ser Pro Arg Asn Gly Gly Ser Leu Asp
            485                 490                 495

Ala Asp Thr Val Ala Gln Val Arg Ser Leu Leu Ala Gln Gly Tyr Arg
        500                 505                 510

Ile Ser Thr Glu Tyr Ala Asp Lys Arg Arg Phe Gln Thr Ser Ser Trp
    515                 520                 525

Gln Ser Cys Pro Pro Ile Lys Thr Gln Gln Glu Ser Gln Val Ile Ala
530                 535                 540

Ala Leu Glu Ser Cys Met Ala Asp His Gln Lys Glu Tyr Val Arg Leu
545                 550                 555                 560

Ile Gly Ile Asp Thr Asn Ala Lys Arg Arg Val Leu Glu Ser Val Ile
            565                 570                 575

Gln Lys Pro Val Ala Ala His
            580

<210> SEQ ID NO 8
<211> LENGTH: 652
<212> TYPE: PRT
<213> ORGANISM: Thermosynechococcus elongatus

<400> SEQUENCE: 8

Met Ala Val Gln Ser Tyr Ala Ala Pro Pro Thr Pro Trp Ser Arg Asp
1               5                   10                  15

Leu Ala Glu Pro Glu Ile Ala Pro Thr Ala Tyr Val His Ser Phe Ser
            20                  25                  30

Asn Leu Ile Gly Asp Val Arg Ile Lys Asp Tyr Val His Ile Ala Pro
        35                  40                  45

Gly Thr Ser Ile Arg Ala Asp Glu Gly Thr Pro Phe His Ile Gly Ser
    50                  55                  60

Arg Thr Asn Ile Gln Asp Gly Val Val Ile His Gly Leu Gln Gln Gly
65                  70                  75                  80

Arg Val Ile Gly Asp Asp Gly Gln Glu Tyr Ser Val Trp Ile Gly Asp
            85                  90                  95

Asn Val Ser Ile Thr His Met Ala Leu Ile His Gly Pro Ala Tyr Ile
        100                 105                 110

Gly Asp Gly Cys Phe Ile Gly Phe Arg Ser Thr Val Phe Asn Ala Arg
    115                 120                 125

Val Gly Ala Gly Cys Val Val Met Met His Val Leu Ile Gln Asp Val
130                 135                 140

Glu Ile Pro Pro Gly Lys Tyr Val Pro Ser Gly Met Val Ile Thr Thr
145                 150                 155                 160

Gln Gln Gln Ala Asp Arg Leu Pro Asn Val Glu Glu Ser Asp Ile His
            165                 170                 175
```

```
Phe Ala Gln His Val Gly Ile Asn Glu Ala Leu Leu Ser Gly Tyr
            180                 185                 190
Gln Cys Ala Glu Asn Ile Ala Cys Ile Ala Pro Ile Arg Asn Glu Leu
        195                 200                 205
Gln Arg Gln Glu Asp Pro Pro Thr Leu His Val Glu Met Leu Thr Gly
    210                 215                 220
Glu Lys Asn Thr Met Thr Thr Asp Tyr Gly Thr His Val Arg Gln Leu
225                 230                 235                 240
Leu Gln Gln Gly Tyr Gln Ile Ser Leu Glu Tyr Ala Asp Ala Arg Arg
            245                 250                 255
Tyr Arg Thr Ser Ser Trp Gln Ser Gly Pro Thr Leu Thr Gly Gln Gln
        260                 265                 270
Glu Ser Gln Val Met Ala Ala Ile Ala Gln Leu Leu Lys Glu His Glu
    275                 280                 285
Gly Glu Tyr Val Arg Leu Ile Gly Val Asp Pro Lys Ala Lys Arg Arg
290                 295                 300
Val Phe Glu Glu Ile Ile Gln Arg Pro Gly Gln Ala Ala Val Ala Ser
305                 310                 315                 320
Ser Ser Ser Ser Arg Pro Ser Ala Thr Val Asn Ala Ser Pro Val Gly
            325                 330                 335
Ser Leu Asp Ala Ala Val Val Ala Gln Val Arg Gln Leu Leu Gln Gln
        340                 345                 350
Gly Tyr Gln Ile Gly Thr Glu His Ala Asp Ala Arg Arg Tyr Arg Thr
    355                 360                 365
Ser Ser Trp Thr Ser Cys Ala Pro Ile Gln Ser Lys Gln Glu Pro Glu
370                 375                 380
Val Leu Ala Ala Leu Glu Ala Cys Leu Gln Glu His Ala Gly Glu Tyr
385                 390                 395                 400
Val Arg Leu Ile Gly Ile Asp Gln Lys Gln Lys Arg Arg Val Leu Glu
            405                 410                 415
Gln Ile Ile Gln Arg Pro Gln Gly Pro Val Ala Ile Ala Pro Lys Thr
        420                 425                 430
Pro Thr Pro Val Ala Thr Ser His Ala Ser Val Ser Ser Gly Gly Asn
    435                 440                 445
Asp Thr Leu Leu Ser Ala Asp Leu Val Asn Gln Ile Gln Asp Leu Leu
450                 455                 460
Arg Gln Gly Cys Gln Val Ile Thr Glu Tyr Ala Asp Gln Arg Arg Phe
465                 470                 475                 480
Arg Thr Ser Ser Trp Gln Ser Gly Ile Lys Ile Thr Ser Ala Gln Gln
            485                 490                 495
Ile Asn Asp Leu Arg Ser Phe Leu Ala Glu His Gln Arg Asp Tyr Ile
        500                 505                 510
Arg Leu Val Gly Val Asn Pro Gln Ala Lys Gln Arg Val Leu Glu Thr
    515                 520                 525
Ile Ile His Arg Pro Asn Gly Lys Ala Ala Ser Asn Gly Asn Ser Thr
530                 535                 540
Arg Gly Gln Gly Phe Thr Pro Arg Pro Thr Ala Ser Ser Gln Gly Ser
545                 550                 555                 560
Pro Ser Thr His Ser Leu Ser Gln Glu Val Ile Glu Gln Val Arg Gln
            565                 570                 575
Leu Leu Gln Gln Gly Tyr Thr Leu Gly Leu Glu His Val Asp Ala Arg
        580                 585                 590
```

Arg Tyr Arg Thr Asn Ser Trp Gln Ser Gly Pro Arg Ile Glu Ala Lys
        595                 600                 605

Asn Leu Asn Glu Ala Leu Ala Ala Ile Gln Ala Cys Leu Gln Glu Tyr
610                 615                 620

Ser Gly Glu Tyr Val Arg Leu Ile Gly Ile Asn Pro Ala Gly Lys Gln
625                 630                 635                 640

Arg Val Ala Glu Ile Leu Leu Gln Gln Ala Ala Lys
                645                 650

<210> SEQ ID NO 9
<211> LENGTH: 418
<212> TYPE: PRT
<213> ORGANISM: Thermosynechococcus elongatus

<400> SEQUENCE: 9

Thr His Val Arg Gln Leu Leu Gln Gln Gly Tyr Gln Ile Ser Leu Glu
1               5                   10                  15

Tyr Ala Asp Ala Arg Arg Tyr Arg Thr Ser Ser Trp Gln Ser Gly Pro
                20                  25                  30

Thr Leu Thr Gly Gln Gln Glu Ser Gln Val Met Ala Ala Ile Ala Gln
            35                  40                  45

Leu Leu Lys Glu His Glu Gly Glu Tyr Val Arg Leu Ile Gly Val Asp
    50                  55                  60

Pro Lys Ala Lys Arg Arg Val Phe Glu Glu Ile Ile Gln Arg Pro Gly
65                  70                  75                  80

Gln Ala Ala Val Ala Ser Ser Ser Ser Arg Pro Ser Ala Thr Val
                85                  90                  95

Asn Ala Ser Pro Val Gly Ser Leu Asp Ala Ala Val Ala Gln Val
            100                 105                 110

Arg Gln Leu Leu Gln Gln Gly Tyr Gln Ile Gly Thr Glu His Ala Asp
    115                 120                 125

Ala Arg Arg Tyr Arg Thr Ser Ser Trp Thr Ser Cys Ala Pro Ile Gln
    130                 135                 140

Ser Lys Gln Glu Pro Glu Val Leu Ala Ala Leu Glu Ala Cys Leu Gln
145                 150                 155                 160

Glu His Ala Gly Glu Tyr Val Arg Leu Ile Gly Ile Asp Gln Lys Gln
                165                 170                 175

Lys Arg Arg Val Leu Glu Gln Ile Ile Gln Arg Pro Gln Gly Pro Val
            180                 185                 190

Ala Ile Ala Pro Lys Thr Pro Thr Pro Val Ala Thr Ser His Ala Ser
    195                 200                 205

Val Ser Ser Gly Gly Asn Asp Thr Leu Leu Ser Ala Asp Leu Val Asn
210                 215                 220

Gln Ile Gln Asp Leu Leu Arg Gln Gly Cys Gln Val Ile Thr Glu Tyr
225                 230                 235                 240

Ala Asp Gln Arg Arg Phe Arg Thr Ser Ser Trp Gln Ser Gly Ile Lys
                245                 250                 255

Ile Thr Ser Ala Gln Gln Ile Asn Asp Leu Arg Ser Phe Leu Ala Glu
            260                 265                 270

His Gln Arg Asp Tyr Ile Arg Leu Val Gly Val Asn Pro Gln Ala Lys
    275                 280                 285

Gln Arg Val Leu Glu Thr Ile Ile His Arg Pro Asn Gly Lys Ala Ala
    290                 295                 300

Ser Asn Gly Asn Ser Thr Arg Gly Gln Gly Phe Thr Pro Arg Pro Thr
305                 310                 315                 320

```
Ala Ser Ser Gln Gly Ser Pro Ser Thr His Ser Leu Ser Gln Glu Val
            325                 330                 335

Ile Glu Gln Val Arg Gln Leu Leu Gln Gln Gly Tyr Thr Leu Gly Leu
            340                 345                 350

Glu His Val Asp Ala Arg Arg Tyr Arg Thr Asn Ser Trp Gln Ser Gly
            355                 360                 365

Pro Arg Ile Glu Ala Lys Asn Leu Asn Glu Ala Leu Ala Ala Ile Gln
            370                 375                 380

Ala Cys Leu Gln Glu Tyr Ser Gly Glu Tyr Val Arg Leu Ile Gly Ile
385                 390                 395                 400

Asn Pro Ala Gly Lys Gln Arg Val Ala Glu Ile Leu Leu Gln Gln Ala
            405                 410                 415

Ala Lys

<210> SEQ ID NO 10
<211> LENGTH: 552
<212> TYPE: PRT
<213> ORGANISM: Trichormus azollae

<400> SEQUENCE: 10

Met Val Val Arg Ser Thr Ala Ala Pro Pro Thr Pro Trp Ser Arg Ser
1               5                   10                  15

Leu Ala Glu Pro Asp Ile His Gln Thr Ala Phe Val His Ser Ser Cys
            20                  25                  30

Asn Leu Ile Gly Asp Val His Leu Gly Gln Asn Val Ile Ile Ala Pro
            35                  40                  45

Gly Thr Ser Ile Arg Ala Asp Glu Gly Thr Pro Phe Phe Ile Gly Glu
        50                  55                  60

Asn Thr Asn Ile Gln Asp Gly Val Val Ile His Gly Leu Glu Gln Gly
65                  70                  75                  80

Arg Val Ile Gly Asp Asp Gly Lys Asn Tyr Ser Val Trp Val Gly Lys
                85                  90                  95

Asp Ala Ser Ile Thr His Met Ala Leu Ile His Gly Pro Ala Tyr Val
            100                 105                 110

Gly Glu Ser Cys Phe Ile Gly Phe Arg Ser Thr Val Phe Asn Ala Arg
            115                 120                 125

Val Gly Ala Gly Cys Ile Val Met Met His Ala Leu Ile Gln Asp Val
        130                 135                 140

Glu Ile Pro Pro Gly Lys Tyr Val Ala Ser Gly Ser Ile Ile Thr Met
145                 150                 155                 160

Gln Gln Gln Ala Asp Arg Leu Pro Asp Val Gln Ala Gln Asp Gln Gln
                165                 170                 175

Phe Ala His His Val Val Gly Ile Asn Gln Ala Leu Arg Ala Gly Tyr
            180                 185                 190

Arg Cys Val Glu Asp Ile Lys Cys Ile Ala Pro Ile Arg Asp Glu Leu
        195                 200                 205

Asn Leu Ser Gly Asp Arg Ser Tyr Thr Ser Ile Ile Val Asp Glu Leu
210                 215                 220

Glu Arg Ser Ser Glu Val Ala Ser Lys Leu Gly Ala Glu Ile Val Asp
225                 230                 235                 240

Gln Val Arg Tyr Leu Leu Asn Gln Gly Tyr Lys Ile Gly Thr Glu His
                245                 250                 255

Val Asp Gln Arg Arg Phe Arg Thr Gly Ser Trp Gln Ser Cys Gln Pro
            260                 265                 270
```

Ile Glu Thr Arg Ser Leu Gly Glu Ala Ile Thr Ala Leu Glu Ser Cys
             275                 280                 285

Leu Ile Asp His Ser Gly Glu Tyr Val Arg Leu Phe Gly Ile Asp Asn
    290                 295                 300

Gly Arg Lys Arg Val Leu Glu Thr Ile Ile Gln Arg Pro Asp Gly Val
305                 310                 315                 320

Val Ala Thr Ser Thr Ser Ser Phe Lys Thr Pro Ala Ala Ser Tyr Ser
                325                 330                 335

Ser Tyr Asn Gly Asn Gly Asn Ser Asn Gly Ala Val Ala Ser Gly Ser
            340                 345                 350

Leu Ser Ala Glu Thr Val Asn Gln Ile Arg Gln Leu Leu Ala Asn Gly
        355                 360                 365

Tyr Lys Ile Gly Thr Glu His Val Asp Gln Arg Phe Arg Thr Gly
    370                 375                 380

Ser Trp Gln Ser Cys Asn Pro Ile Glu Ala Thr Ser Ala Asn Asp Val
385                 390                 395                 400

Val Ala Ala Leu Glu Glu Cys Met Thr Ser His Gln Gly Glu Tyr Val
                405                 410                 415

Arg Leu Ile Gly Ile Asp Ser Lys Ala Lys Arg Val Leu Glu Ala
            420                 425                 430

Ile Ile Gln Arg Pro Asn Gly Gln Val Val Ser Ser Gly Ser Ala Lys
        435                 440                 445

Thr Ser Gly Thr Leu Tyr Ser Gly Ala Thr Ala Ser Ala Thr Ala Thr
    450                 455                 460

Ser Thr Arg Leu Ser Thr Glu Val Val Asp Gln Leu Lys Gln Leu Leu
465                 470                 475                 480

Thr Gly Gly Phe Lys Ile Ser Val Glu His Val Asp Gln Arg Arg Phe
                485                 490                 495

Arg Thr Gly Ser Trp Val Ser Cys Gly Gln Ile Gln Ala Thr Ser Glu
            500                 505                 510

Arg Asp Val Leu Ala Ala Leu Glu Ala Val Ile Ser Glu Tyr Ala Gly
        515                 520                 525

Glu Tyr Val Arg Leu Ile Gly Ile Asp Pro Val Ala Lys Arg Arg Val
    530                 535                 540

Leu Glu Ala Ile Ile Gln Arg Pro
545                 550

<210> SEQ ID NO 11
<211> LENGTH: 323
<212> TYPE: PRT
<213> ORGANISM: Trichormus azollae

<400> SEQUENCE: 11

Val Ala Ser Lys Leu Gly Ala Glu Ile Val Asp Gln Val Arg Tyr Leu
1               5                   10                  15

Leu Asn Gln Gly Tyr Lys Ile Gly Thr Glu His Val Asp Gln Arg Arg
            20                  25                  30

Phe Arg Thr Gly Ser Trp Gln Ser Cys Gln Pro Ile Glu Thr Arg Ser
        35                  40                  45

Leu Gly Glu Ala Ile Thr Ala Leu Glu Ser Cys Leu Ile Asp His Ser
    50                  55                  60

Gly Glu Tyr Val Arg Leu Phe Gly Ile Asp Asn Gly Arg Lys Arg Val
65                  70                  75                  80

Leu Glu Thr Ile Ile Gln Arg Pro Asp Gly Val Val Ala Thr Ser Thr

```
                85                  90                  95
Ser Ser Phe Lys Thr Pro Ala Ala Ser Tyr Ser Ser Tyr Asn Gly Asn
            100                 105                 110

Gly Asn Ser Asn Gly Ala Val Ala Ser Gly Ser Leu Ser Ala Glu Thr
            115                 120                 125

Val Asn Gln Ile Arg Gln Leu Leu Ala Asn Gly Tyr Lys Ile Gly Thr
130                 135                 140

Glu His Val Asp Gln Arg Arg Phe Arg Thr Gly Ser Trp Gln Ser Cys
145                 150                 155                 160

Asn Pro Ile Glu Ala Thr Ser Ala Asn Asp Val Val Ala Ala Leu Glu
                165                 170                 175

Glu Cys Met Thr Ser His Gln Gly Glu Tyr Val Arg Leu Ile Gly Ile
            180                 185                 190

Asp Ser Lys Ala Lys Arg Arg Val Leu Glu Ala Ile Ile Gln Arg Pro
            195                 200                 205

Asn Gly Gln Val Val Ser Ser Gly Ser Ala Lys Thr Ser Gly Thr Leu
        210                 215                 220

Tyr Ser Gly Ala Thr Ala Ser Ala Thr Ala Thr Ser Thr Arg Leu Ser
225                 230                 235                 240

Thr Glu Val Val Asp Gln Leu Lys Gln Leu Leu Thr Gly Gly Phe Lys
                245                 250                 255

Ile Ser Val Glu His Val Asp Gln Arg Arg Phe Arg Thr Gly Ser Trp
            260                 265                 270

Val Ser Cys Gly Gln Ile Gln Ala Thr Ser Glu Arg Asp Val Leu Ala
            275                 280                 285

Ala Leu Glu Ala Val Ile Ser Glu Tyr Ala Gly Glu Tyr Val Arg Leu
        290                 295                 300

Ile Gly Ile Asp Pro Val Ala Lys Arg Arg Val Leu Glu Ala Ile Ile
305                 310                 315                 320

Gln Arg Pro

<210> SEQ ID NO 12
<211> LENGTH: 161
<212> TYPE: PRT
<213> ORGANISM: Synechococcus elongatus

<400> SEQUENCE: 12

Met His Leu Pro Pro Leu Glu Pro Pro Ile Ser Asp Arg Tyr Phe Ala
1               5                   10                  15

Ser Gly Glu Val Thr Ile Ala Ala Asp Val Val Ile Ala Pro Gly Val
            20                  25                  30

Leu Leu Ile Ala Glu Ala Asp Ser Arg Ile Glu Ile Ala Ser Gly Val
        35                  40                  45

Cys Ile Gly Leu Gly Ser Val Ile His Ala Arg Gly Gly Ala Ile Ile
    50                  55                  60

Ile Gln Ala Gly Ala Leu Leu Ala Gly Val Leu Ile Val Gly Gln
65                  70                  75                  80

Ser Ile Val Gly Arg Gln Ala Cys Leu Gly Ala Ser Thr Thr Leu Val
                85                  90                  95

Asn Thr Ser Ile Glu Ala Gly Gly Val Thr Ala Pro Gly Ser Leu Leu
            100                 105                 110

Ser Ala Glu Thr Pro Pro Thr Thr Ala Thr Val Ser Ser Ser Glu Pro
            115                 120                 125

Ala Gly Arg Ser Pro Gln Ser Ser Ala Ile Ala His Pro Thr Lys Val
```

```
                130                 135                 140
Tyr Gly Lys Glu Gln Phe Leu Arg Met Arg Gln Ser Met Phe Pro Asp
145                 150                 155                 160

Arg
```

<210> SEQ ID NO 13
<211> LENGTH: 18
<212> TYPE: PRT
<213> ORGANISM: Synechococcus elongatus

<400> SEQUENCE: 13

```
Val Tyr Gly Lys Glu Gln Phe Leu Arg Met Arg Gln Ser Met Phe Pro
1               5                   10                  15

Asp Arg
```

<210> SEQ ID NO 14
<211> LENGTH: 17
<212> TYPE: PRT
<213> ORGANISM: Prochlorothrix hollandica

<400> SEQUENCE: 14

```
Val Tyr Gly Arg Asp Tyr Phe Leu Gln Met Arg Phe Ser Leu Phe Pro
1               5                   10                  15

Asp
```

<210> SEQ ID NO 15
<211> LENGTH: 44
<212> TYPE: PRT
<213> ORGANISM: Halothece sp. PCC 7418

<400> SEQUENCE: 15

```
Ile Tyr Gly Gln Thr His Ile Glu Arg Leu Met Val Thr Leu Phe Pro
1               5                   10                  15

His Lys Glu Lys Phe Lys Lys Lys Thr Asn Asp Trp Phe Leu Val Leu
            20                  25                  30

Gly Ser Leu Leu Phe Asp Asp Phe Pro Asn Asn Glu
        35                  40
```

<210> SEQ ID NO 16
<211> LENGTH: 18
<212> TYPE: PRT
<213> ORGANISM: Moorea producens

<400> SEQUENCE: 16

```
Glu Gln Phe Phe Arg Arg Met Arg Gln Ser Leu Asn Arg Ala Phe Ser
1               5                   10                  15

Glu Arg
```

<210> SEQ ID NO 17
<211> LENGTH: 272
<212> TYPE: PRT
<213> ORGANISM: Synechococcus elongatus

<400> SEQUENCE: 17

```
Met Arg Lys Leu Ile Glu Gly Leu Arg His Phe Arg Thr Ser Tyr Tyr
1               5                   10                  15

Pro Ser His Arg Asp Leu Phe Glu Gln Phe Ala Lys Gly Gln His Pro
            20                  25                  30

Arg Val Leu Phe Ile Thr Cys Ser Asp Ser Arg Ile Asp Pro Asn Leu
        35                  40                  45
```

Ile Thr Gln Ser Gly Met Gly Glu Leu Phe Val Ile Arg Asn Ala Gly
            50                  55                  60

Asn Leu Ile Pro Pro Phe Gly Ala Ala Asn Gly Gly Glu Gly Ala Ser
 65                  70                  75                  80

Ile Glu Tyr Ala Ile Ala Ala Leu Asn Ile Glu His Val Val Cys
                 85                  90                  95

Gly His Ser His Cys Gly Ala Met Lys Gly Leu Leu Lys Leu Asn Gln
                100                 105                 110

Leu Gln Glu Asp Met Pro Leu Val Tyr Asp Trp Leu Gln His Ala Gln
            115                 120                 125

Ala Thr Arg Arg Leu Val Leu Asp Asn Tyr Ser Gly Tyr Glu Thr Asp
            130                 135                 140

Asp Leu Val Glu Ile Leu Val Ala Glu Asn Val Leu Thr Gln Ile Glu
145                 150                 155                 160

Asn Leu Lys Thr Tyr Pro Ile Val Arg Ser Arg Leu Phe Gln Gly Lys
                165                 170                 175

Leu Gln Ile Phe Gly Trp Ile Tyr Glu Val Glu Ser Gly Glu Val Leu
            180                 185                 190

Gln Ile Ser Arg Thr Ser Ser Asp Asp Thr Gly Ile Asp Glu Cys Pro
            195                 200                 205

Val Arg Leu Pro Gly Ser Gln Glu Lys Ala Ile Leu Gly Arg Cys Val
            210                 215                 220

Val Pro Leu Thr Glu Glu Val Ala Val Ala Pro Glu Pro Glu Pro
225                 230                 235                 240

Val Ile Ala Ala Val Ala Ala Pro Pro Ala Asn Tyr Ser Ser Arg Gly
                245                 250                 255

Trp Leu Ala Pro Glu Gln Gln Gln Arg Ile Tyr Arg Gly Asn Ala Ser
            260                 265                 270

<210> SEQ ID NO 18
<211> LENGTH: 272
<212> TYPE: PRT
<213> ORGANISM: Synechococcus elongatus

<400> SEQUENCE: 18

Met Arg Lys Leu Ile Glu Gly Leu Arg His Phe Arg Thr Ser Tyr Tyr
 1               5                  10                  15

Pro Ser His Arg Asp Leu Phe Glu Gln Phe Ala Lys Gly Gln His Pro
                 20                  25                  30

Arg Val Leu Phe Ile Thr Cys Ser Asp Ser Arg Ile Asp Pro Asn Leu
             35                  40                  45

Ile Thr Gln Ser Gly Met Gly Glu Leu Phe Val Ile Arg Asn Ala Gly
            50                  55                  60

Asn Leu Ile Pro Pro Phe Gly Ala Ala Asn Gly Gly Glu Gly Ala Ser
 65                  70                  75                  80

Ile Glu Tyr Ala Ile Ala Ala Leu Asn Ile Glu His Val Val Cys
                 85                  90                  95

Gly His Ser His Cys Gly Ala Met Lys Gly Leu Leu Lys Leu Asn Gln
                100                 105                 110

Leu Gln Glu Asp Met Pro Leu Val Tyr Asp Trp Leu Gln His Ala Gln
            115                 120                 125

Ala Thr Arg Arg Leu Val Leu Asp Asn Tyr Ser Gly Tyr Glu Thr Asp
            130                 135                 140

Asp Leu Val Glu Phe Leu Val Ala Glu Asn Val Leu Thr Gln Ile Glu

```
            145                 150                 155                 160
        Asn Leu Lys Thr Tyr Pro Ile Val Arg Ser Arg Leu Phe Gln Gly Lys
                        165                 170                 175
        Leu Gln Ile Phe Gly Trp Ile Tyr Glu Val Glu Ser Gly Glu Val Leu
                        180                 185                 190
        Gln Ile Ser Arg Thr Ser Ser Asp Asp Thr Gly Ile Asp Glu Cys Pro
                        195                 200                 205
        Val Arg Leu Pro Gly Ser Gln Glu Lys Ala Ile Leu Gly Arg Cys Val
            210                 215                 220
        Val Pro Leu Thr Glu Glu Val Ala Val Ala Pro Glu Pro Glu Pro
        225                 230                 235                 240
        Val Ile Ala Ala Val Ala Ala Pro Pro Ala Asn Tyr Ser Ser Arg Gly
                        245                 250                 255
        Trp Leu Ala Pro Glu Gln Gln Gln Arg Ile Tyr Arg Gly Asn Ala Ser
                        260                 265                 270

<210> SEQ ID NO 19
<211> LENGTH: 279
<212> TYPE: PRT
<213> ORGANISM: Geminocystis herdmanii

<400> SEQUENCE: 19

Met Lys Lys Ile Ile Glu Gly Leu His Arg Phe Gln Ala Gly Tyr Phe
        1               5                   10                  15
        Glu Ser His Arg Asp Leu Phe Glu Gln Leu Ser His Gly Gln His Pro
                        20                  25                  30
        Arg Ile Leu Phe Ile Thr Cys Ser Asp Ser Arg Ile Asp Pro Asn Leu
                        35                  40                  45
        Ile Thr Gln Ala Asn Val Gly Glu Leu Phe Val Ile Arg Asn Ala Gly
        50                  55                  60
        Asn Ile Ile Pro Pro Phe Gly Ala Thr Asn Gly Gly Glu Gly Ala Ser
        65                  70                  75                  80
        Ile Glu Tyr Ala Ile Thr Ala Leu Asp Ile Glu Gln Val Ile Val Cys
                        85                  90                  95
        Gly His Ser His Cys Gly Ala Met Lys Gly Leu Leu Lys Met Ser Lys
                        100                 105                 110
        Leu Ala Asp Lys Met Pro Leu Val Tyr Glu Trp Leu Lys Gln Ala Glu
                        115                 120                 125
        Ala Thr Arg Arg Leu Ile Ile Asp Asn Tyr Ser His Leu Glu Gly Glu
                        130                 135                 140
        Glu Leu Leu Gln Ile Thr Val Ala Glu Asn Val Leu Thr Gln Leu Glu
        145                 150                 155                 160
        Asn Leu Asn Thr Tyr Pro Ile Val Arg Ser Arg Leu His Gln Gly Arg
                        165                 170                 175
        Leu Ser Leu His Gly Trp Ile Tyr Gly Ile Glu Thr Gly Glu Val Leu
                        180                 185                 190
        Thr Tyr Asp Pro Lys Val His Asp Phe Val Asn Leu Glu Ser Arg Thr
                        195                 200                 205
        Asp Asn Ser Glu Tyr Ile Tyr Asn Leu His Pro Ser Cys Ser Val Ala
            210                 215                 220
        Lys Ser Met Phe Tyr Gly Ile Pro Asp Glu Asn Asp Asp Lys Val Gln
        225                 230                 235                 240
        Pro Ser Glu Pro Ile Pro Gln Thr Ile Asn Pro Asn Leu Pro Arg Ser
                        245                 250                 255
```

Arg Ser Gly Ala Ala Arg Ser Asn Arg Leu Ser Pro Glu Gln Gln
            260                 265                 270

Arg Ile Tyr Arg Gly Ser Thr
        275

<210> SEQ ID NO 20
<211> LENGTH: 275
<212> TYPE: PRT
<213> ORGANISM: Aliterella atlantica

<400> SEQUENCE: 20

Met Arg Lys Leu Ile Lys Gly Leu Arg Ala Phe Lys Asp Asn Tyr Tyr
1               5                   10                  15

Ser Asn His Leu Glu Leu Phe Glu Lys Leu Thr His Ala Gln Lys Pro
            20                  25                  30

Arg Val Leu Phe Ile Thr Cys Ser Asp Ser Arg Ile Asp Pro Asn Leu
        35                  40                  45

Ile Thr Gln Ala Ala Val Gly Glu Leu Phe Val Ile Arg Asn Ala Gly
    50                  55                  60

Asn Ile Ile Pro Pro Phe Gly Ala Thr Asn Gly Gly Glu Gly Ala Thr
65                  70                  75                  80

Val Glu Tyr Ala Val His Ala Leu Gly Ile Glu Gln Ile Val Val Cys
                85                  90                  95

Gly His Ser His Cys Gly Ala Met Lys Gly Leu Leu Lys Leu Asn Lys
            100                 105                 110

Leu Gln Gln Asp Met Pro Leu Val Tyr Asn Trp Leu Gln Tyr Ala Glu
        115                 120                 125

Ser Thr Arg Arg Leu Val Gln Glu Asn Tyr Asn Ser Tyr Ser Glu Glu
    130                 135                 140

Glu Leu Val Glu Ile Ala Val Ala Glu Asn Val Leu Thr Gln Ile Glu
145                 150                 155                 160

Asn Leu Lys Thr Tyr Pro Val Val Arg Ser Lys Leu Tyr Gln Gly Lys
                165                 170                 175

Leu Gln Ile Tyr Ala Trp Ile Tyr His Leu Glu Thr Gly Glu Val Leu
            180                 185                 190

Ala Tyr Asp Pro Gln Ser His Ala Tyr Val Ala Pro Gln Ser Gln Leu
        195                 200                 205

Met Asn Gly Asp Thr Thr Glu Ser Ile Glu Thr Arg Ile Ala Asn Thr
    210                 215                 220

Ser Ala Pro Ile Val Ala Cys Glu Phe Pro Ser Arg His Lys Gln Arg
225                 230                 235                 240

Gln Val Ala His Asn Thr Ala Asn Asn Asp Gly Asp Thr Leu Pro Asp
                245                 250                 255

Met Trp Leu Ser Pro Gln Gln Ala Glu Arg Ile Tyr Arg Gly Ser Asn
            260                 265                 270

Gly Asn Arg
        275

<210> SEQ ID NO 21
<211> LENGTH: 279
<212> TYPE: PRT
<213> ORGANISM: Leptolyngbya boryana

<400> SEQUENCE: 21

Met Lys Lys Leu Ile Gln Gly His Gln Gln Phe Trp Glu Ser Tyr Val
1               5                   10                  15

Pro Ser His Leu Asp Gln Leu Glu Leu Ser His Gly Gln Lys Pro
            20                  25                  30

Arg Val Leu Phe Ile Thr Cys Ser Asp Ser Arg Ile Asp Pro Asn Leu
        35                  40                  45

Ile Thr Gln Ala Gly Ile Gly Glu Leu Phe Val Ile Arg Asn Ala Gly
    50                  55                  60

Asn Ile Ile Pro Pro Phe Gly Ala Ala Asn Gly Gly Glu Gly Ala Ala
65                  70                  75                  80

Val Glu Tyr Ala Ile Ala Ala Leu Asp Ile Gln Gln Ile Ile Val Cys
                85                  90                  95

Gly His Ser His Cys Gly Ala Met Lys Gly Leu Leu Lys Leu Asn Lys
            100                 105                 110

Leu Gln Glu Asp Met Pro Leu Val Tyr Asp Trp Leu Lys His Ala Glu
        115                 120                 125

Ala Thr Arg Arg Leu Val Lys Glu Asn Tyr Ser Gln Tyr Ser Gly Glu
    130                 135                 140

Glu Leu Leu Glu Ile Thr Ile Ala Glu Asn Val Leu Thr Gln Ile Glu
145                 150                 155                 160

Asn Leu Lys Thr Tyr Pro Val Val His Ser Arg Leu Tyr Gln Gly Lys
                165                 170                 175

Leu Glu Ile Tyr Gly Trp Val Tyr His Ile Glu Thr Gly Glu Leu Leu
            180                 185                 190

Ala Phe Asp Pro Glu Thr His Ala Tyr Val Pro Pro Gln Ser Gln Leu
        195                 200                 205

Ser Pro Arg Glu Leu Gly Ala Phe Tyr Glu Lys Thr Ser Ala Pro Pro
210                 215                 220

Val Ala Cys Asn Leu Pro His Lys Glu Asp Asn Gly Asn Gly Gln Leu
225                 230                 235                 240

Arg Gln Pro Val Thr Ile Arg Ser Gln Val Lys Ser Ala Glu Pro Val
                245                 250                 255

Pro Gln Thr Glu Val Met Pro Trp Leu Thr Ala Glu Gln Ala Gln Arg
            260                 265                 270

Ile Tyr Gln Gly Ser Lys Arg
        275

<210> SEQ ID NO 22
<211> LENGTH: 608
<212> TYPE: PRT
<213> ORGANISM: Artificial Sequence
<220> FEATURE:
<223> OTHER INFORMATION: A synthetic protein

<400> SEQUENCE: 22

Met Thr Val Ser Ala Tyr Asn Gly Gln Gly Arg Leu Ser Ser Glu Val
1               5                   10                  15

Ile Thr Gln Val Arg Ser Leu Leu Asn Gln Gly Tyr Arg Ile Gly Thr
            20                  25                  30

Glu His Ala Asp Lys Arg Arg Phe Arg Thr Ser Ser Trp Gln Pro Cys
        35                  40                  45

Ala Pro Ile Gln Ser Thr Asn Glu Arg Gln Val Leu Ser Glu Leu Glu
    50                  55                  60

Asn Cys Leu Ser Glu His Glu Gly Glu Tyr Val Arg Leu Leu Gly Ile
65                  70                  75                  80

Asp Thr Asn Thr Arg Ser Arg Val Phe Glu Ala Leu Ile Gln Arg Pro
                85                  90                  95

```
Asp Gly Ser Val Pro Glu Ser Leu Gly Ser Gln Pro Val Ala Val Ala
            100                 105                 110
Ser Gly Gly Gly Arg Gln Ser Ser Tyr Ala Ser Val Ser Gly Asn Leu
        115                 120                 125
Ser Ala Glu Val Val Asn Lys Val Arg Asn Leu Leu Ala Gln Gly Tyr
    130                 135                 140
Arg Ile Gly Thr Glu His Ala Asp Lys Arg Arg Phe Arg Thr Ser Ser
145                 150                 155                 160
Trp Gln Ser Cys Ala Pro Ile Gln Ser Ser Asn Glu Arg Gln Val Leu
                165                 170                 175
Ala Glu Leu Glu Asn Cys Leu Ser Glu His Glu Gly Glu Tyr Val Arg
            180                 185                 190
Leu Leu Gly Ile Asp Thr Ala Ser Arg Ser Arg Val Phe Glu Ala Leu
        195                 200                 205
Ile Gln Asp Pro Gln Gly Pro Val Gly Ser Ala Lys Ala Ala Ala Ala
    210                 215                 220
Pro Val Ser Ser Ala Thr Pro Ser Ser His Ser Tyr Thr Ser Asn Gly
225                 230                 235                 240
Ser Ser Ser Ser Asp Val Ala Gly Gln Val Arg Gly Leu Leu Ala Gln
                245                 250                 255
Gly Tyr Arg Ile Ser Ala Glu Val Ala Asp Lys Arg Arg Phe Gln Thr
            260                 265                 270
Ser Ser Trp Gln Ser Leu Pro Ala Leu Ser Gly Gln Ser Glu Ala Thr
        275                 280                 285
Val Leu Pro Ala Leu Glu Ser Ile Leu Gln Glu His Lys Gly Lys Tyr
    290                 295                 300
Val Arg Leu Ile Gly Ile Asp Pro Ala Ala Arg Arg Arg Val Ala Glu
305                 310                 315                 320
Leu Leu Ile Gln Lys Pro Gly Ser Arg Lys Leu Ile Glu Gly Leu Arg
                325                 330                 335
His Phe Arg Thr Ser Tyr Tyr Pro Ser His Arg Asp Leu Phe Glu Gln
            340                 345                 350
Phe Ala Lys Gly Gln His Pro Arg Val Leu Phe Ile Thr Cys Ser Asp
        355                 360                 365
Ser Arg Ile Asp Pro Asn Leu Ile Thr Gln Ser Gly Met Gly Glu Leu
    370                 375                 380
Phe Val Ile Arg Asn Ala Gly Asn Leu Ile Pro Pro Phe Gly Ala Ala
385                 390                 395                 400
Asn Gly Gly Glu Gly Ala Ser Ile Glu Tyr Ala Ile Ala Ala Leu Asn
                405                 410                 415
Ile Glu His Val Val Cys Gly His Ser His Cys Gly Ala Met Lys
            420                 425                 430
Gly Leu Leu Lys Leu Asn Gln Leu Gln Glu Asp Met Pro Leu Val Tyr
        435                 440                 445
Asp Trp Leu Gln His Ala Gln Ala Thr Arg Arg Leu Val Leu Asp Asn
    450                 455                 460
Tyr Ser Gly Tyr Glu Thr Asp Asp Leu Val Glu Ile Leu Val Ala Glu
465                 470                 475                 480
Asn Val Leu Thr Gln Ile Glu Asn Leu Lys Thr Tyr Pro Ile Val Arg
                485                 490                 495
Ser Arg Leu Phe Gln Gly Lys Leu Gln Ile Phe Gly Trp Ile Tyr Glu
            500                 505                 510
Val Glu Ser Gly Glu Val Leu Gln Ile Ser Arg Thr Ser Ser Asp Asp
```

```
                515                 520                 525
Thr Gly Ile Asp Glu Cys Pro Val Arg Leu Pro Gly Ser Gln Glu Lys
            530                 535                 540

Ala Ile Leu Gly Arg Cys Val Val Pro Leu Thr Glu Glu Val Ala Val
545                 550                 555                 560

Ala Pro Pro Glu Pro Glu Pro Val Ile Ala Val Ala Ala Pro Pro
                565                 570                 575

Ala Asn Tyr Ser Ser Arg Gly Trp Leu Gly Ser Gly Gly Ser Val Tyr
            580                 585                 590

Gly Lys Glu Gln Phe Leu Arg Met Arg Gln Ser Met Phe Pro Asp Arg
                595                 600                 605

<210> SEQ ID NO 23
<211> LENGTH: 113
<212> TYPE: PRT
<213> ORGANISM: Synechococcus elongatus

<400> SEQUENCE: 23

Met Ser Gln Gln Ala Ile Gly Ser Leu Glu Thr Lys Gly Phe Pro Pro
1               5                   10                  15

Ile Leu Ala Ala Ala Asp Ala Met Val Lys Ala Gly Arg Ile Thr Ile
            20                  25                  30

Val Ser Tyr Met Arg Ala Gly Ser Ala Arg Phe Ala Val Asn Ile Arg
        35                  40                  45

Gly Asp Val Ser Glu Val Lys Thr Ala Met Asp Ala Gly Ile Glu Ala
    50                  55                  60

Ala Lys Asn Thr Pro Gly Gly Thr Leu Glu Thr Trp Val Ile Ile Pro
65                  70                  75                  80

Arg Pro His Glu Asn Val Glu Ala Val Phe Pro Ile Gly Phe Gly Pro
                85                  90                  95

Glu Val Glu Gln Tyr Arg Leu Ser Ala Glu Gly Thr Gly Ser Gly Arg
            100                 105                 110

Arg

<210> SEQ ID NO 24
<211> LENGTH: 99
<212> TYPE: PRT
<213> ORGANISM: Synechococcus elongatus

<400> SEQUENCE: 24

Met Arg Ile Ala Lys Val Arg Gly Thr Val Val Ser Thr Tyr Lys Glu
1               5                   10                  15

Pro Ser Leu Gln Gly Val Lys Phe Leu Val Val Gln Phe Leu Asp Glu
            20                  25                  30

Ala Gly Gln Ala Leu Gln Glu Tyr Glu Val Ala Ala Asp Met Val Gly
        35                  40                  45

Ala Gly Val Asp Glu Trp Val Leu Ile Ser Arg Gly Ser Gln Ala Arg
    50                  55                  60

His Val Arg Asp Cys Gln Glu Arg Pro Val Asp Ala Ala Val Ile Ala
65                  70                  75                  80

Ile Ile Asp Thr Val Asn Val Glu Asn Arg Ser Val Tyr Asp Lys Arg
                85                  90                  95

Glu His Ser

<210> SEQ ID NO 25
<211> LENGTH: 472
```

<212> TYPE: PRT
<213> ORGANISM: Synechococcus elongatus

<400> SEQUENCE: 25

```
Met Pro Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400
```

```
Gly Gly Thr Leu Gly His Pro Trp Gly Asn Ala Pro Gly Ala Thr Ala
            405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
            435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 26
<211> LENGTH: 1827
<212> TYPE: DNA
<213> ORGANISM: Synechococcus elongatus

<400> SEQUENCE: 26
atgaccgtga gcgcttataa cggccaaggc cgactcagtt ccgaagtcat cacccaagtc      60
cggagtttgc tgaaccaggg ctatcggatt gggacggaac atgcggacaa cgccgcttc     120 cggactagct cttggcagcc ctgcgcgccg attcaaagca cgaacgagcg ccaggtcttg     180
agcgaactgg aaaattgtct gagcgaacac gaaggtgaat acgttcgctt gctcggcatc     240
gataccaata ctcgcagccg tgtttttgaa gccctgattc aacggcccga tggttcggtt     300
cctgaatcgc tggggagcca accggtggca gtcgcttccg gtggtggccg tcagagcagc     360
tatgccagcg tcagcggcaa cctctcagca gaagtggtca ataaagtccg caacctctta     420
gcccaaggct atcggattgg acggaacat gcagacaagc gccgctttcg gactagctct     480
tggcagtcct gcgcaccgat tcaaagttcg aatgagcgcc aggttctggc tgaactggaa     540
aactgtctga gcgagcacga aggtgagtac gttcgcctgc tgggcatcga cactgctagc     600
cgcagtcgtg ttttgaagc cctgatccaa gatcccaag accggtggg ttccgccaaa      660 gcggccgccg cacctgtgag ttcggcaacg cccagcagcc acagctacac ctcaaatgga     720
tcgagttcga gcgatgtcgc tggacaggtt cggggtctgc tagcccaagg ctaccggatc     780
agtgcggaag tcgccgataa gcgtcgcttc caaaccagct cttggcagag tttgccggct     840
ctgagtggcc agagcgaagc aactgtcttg cctgctttgg agtcaattct gcaagagcac     900
aagggtaagt atgtgcgcct gattgggatt gaccctgcgg ctcgtcgtcg cgtggctgaa     960
ctgttgattc aaaagccggg atctcgcaag ctcatcgagg ggttacggca tttccgtacg    1020
tcctactacc cgtctcatcg ggacctgttc gagcagtttg ccaaaggtca gcaccctcga    1080
gtcctgttca ttacctgctc agactcgcgc attgaccta acctcattac ccagtcgggc    1140
atgggtgagc tgttcgtcat cgcaacgct ggcaatctga tcccgccctt cggtgccgcc    1200
aacggtggtg aagggcatc gatcgaatac gcgatcgcag ctttgaacat tgagcatgtt    1260
gtggtctgcg gtcactcgca ctgcggtgcg atgaaagggc tgctcaagct caatcagctg    1320
caagaggaca tgccgctggt ctatgactgg ctgcagcatg cccaagccac ccgccgccta    1380
gtcttggata ctacagcgg ttatgagact gacgacttgg tagagattct ggtcgccgag    1440
aatgtgctga cgcagatcga gaaccttaag acctacccga tcgtgcgatc gcgccttttc    1500
caaggcaagc tgcagatttt tggctggatt tatgaagttg aaagcggcga ggtcttgcag    1560
attagccgta ccagcagtga tgacacaggc attgatgaat gtccagtgcg tttgcccggc    1620
agccaggaga aagccattct cggtcgttgt gtcgtccccc tgaccgaaga agtggccgtt    1680
```

| | | |
|---|---|---|
| gctccaccag agccggagcc tgtgatcgcg gctgtggcgg ctccacccgc caactactcc | 1740 | |
| agtcgcggtt ggttgggatc tggaggcagt gtctacggca aggaacagtt tttgcggatg | 1800 | |
| cgccagagca tgttccccga tcgctaa | 1827 | |

<210> SEQ ID NO 27
<211> LENGTH: 1827
<212> TYPE: DNA
<213> ORGANISM: Escherichia coli

<400> SEQUENCE: 27

| | |
|---|---|
| atgaccgttt ccgcgtacaa cggacagggc agactttcga gtgaagttat aacccaggtc | 60 |
| cggtctttgt tgaaccaagg ctatcgcatc gggaccgaac atgccgataa gcgccgtttc | 120 |
| cggacctcaa gttggcaacc gtgcgcgccc atccagtcaa ccaatgaacg ccaggtattg | 180 |
| tctgaattag agaattgctt atcggaacac gaaggagaat acgttcgctt gttaggaatt | 240 |
| gacactaaca caagaagtcg ggttttcgaa gcactgatcc agcgcccgga cgggtctgtt | 300 |
| cctgaatctt tgggcagcca gccagtagca gtggcttccg gaggcggaag acaatcgtcc | 360 |
| tatgcatctg tttccggcaa cttgtctgct gaggttgtta ataaggtgcg caacctgctt | 420 |
| gcccagggtt acagaattgg cacggagcac gccgataagc gccgttttag aaccagctcg | 480 |
| tggcagtctt gtgcgccgat acagtcctcg aatgaacggc aggtgctggc agagttagag | 540 |
| aattgcctga gtgagcatga aggagaatac gtccgccttc tgggcattga caccgcttcc | 600 |
| cgttcgcgtg ttttcgaagc ccttattcag gatccgcaag gccccgtggg ttccgccaaa | 660 |
| gctgccgcag cacctgtatc aagtgctacc ccttcgtccc acagttatac gtcgaacggc | 720 |
| agctcatcat ctgacgtggc gggccaggtt cgtgggttgt tggctcaagg gtatcggata | 780 |
| tcggctgagg ttgcggataa acgtcggttc caaacatcgt cgtggcagtc cttgcctgca | 840 |
| ttatcgggtc aatcggaagc aacggtcctt cctgcgctgg agagtatcct tcaggagcac | 900 |
| aagggcaagt acgtcagatt gatagggatc gatccggcgg cgcggagacg ggtggcagaa | 960 |
| ttgcttatcc aaaaacccgg ttcgcgcaag ttgatcgaag gattaagaca ttttagaacc | 1020 |
| tcatattacc cgagtcatag agatttattc gagcagtttg caaagggtca acaccctaga | 1080 |
| gtcctgttca tcacttgctc ggattcacgg atcgatccta atttgatcac gcagtctggt | 1140 |
| atgggagagc ttttcgtcat ccgtaacgca ggtaacctga ttccaccttt cggcgcggca | 1200 |
| aatggggggtg agggtgcgtc cattgaatat gccatcgccg cattgaatat cgaacacgta | 1260 |
| gttgtatgtg gccactcgca ctgtggagcg atgaaagggc tgctgaagct taaccagctg | 1320 |
| caagaagaca tgccccttgt ttacgattgg ttgcaacacg cgcaggccac gagacgtctg | 1380 |
| gtccttgaca actacagcgg atatgaaacg gacgaccttg tcgagatcct ggtcgccgag | 1440 |
| aacgtattga cccaaataga gaatctgaag acctacccaa ttgtgcgctc gcgcttgttc | 1500 |
| cagggtaagt tacaaatttt cggttggatc tatgaagtgg aaagtggaga ggtcttgcaa | 1560 |
| atctcacgta catcctcgga cgacacagga atagacgagt gccccgtccg tttaccggga | 1620 |
| tcgcaagaga aggccatttt aggacggtgc gtcgtgccac tgacagagga agtggctgtt | 1680 |
| gcccctccag aaccagagcc tgtcattgct gcggtggccg caccaccgc gaattactcc | 1740 |
| agtcgcggtt ggctgggctc tggaggctct gtctacggaa aggaacaatt ccttcgtatg | 1800 |
| cggcaatcaa tgttcccgga ccgctaa | 1827 |

<210> SEQ ID NO 28

<211> LENGTH: 1827
<212> TYPE: DNA
<213> ORGANISM: Nicotiana tabacum

<400> SEQUENCE: 28

```
atgactgtga gtgcatataa tggacaaggt agattgagtt ctgaagtgat aactcaagtg    60
cgtagccttt tgaatcaagg atacagaatt gggaccgaac acgcagataa agaaggttt    120
agaaccagtt catggcagcc atgcgccccc atccagtcta ctaatgaaag acaagtgctt   180
tctgagctgg aaaactgtct tagtgaacat gaaggcgagt atgtgcgatt gctgggtatc   240
gatactaaca ctcgtagccg tgttttgaa gctctgatac aacgacctga cggtagtgtc   300
cccgaatcac tgggtagcca gcccgtagca gtagctagcg ggggcgggcg acagtcctcc   360
tacgcctctg ttagcggcaa cctctcagcc gaagtagtga acaaagtaag aaacctcctc   420
gcccagggtt accgtatagg aaccgagcac gcagacaaaa gaagattcag gactagcagc   480
tggcaatcct gcgcacccat acaatcttcc aacgaaagac aggtactggc agaattggaa   540
aactgtcttt cagaacatga aggcgagtac gtccgtctgc tggggatcga cacagcaagc   600
agaagccgag tatttgaagc cctcattcaa gatccacagg ggccagtagg tagtgcaaag   660
gcagctgcag ctcccgtttc atctgctact cccagcagtc acagctacac ttctaatggg   720
tcttccagta gtgacgtcgc cggacaggta agaggcctgt tggcacaggg ttaccgaata   780
tctgccgaag tagctgataa aaggcgattc cagacttcat cctggcagtc ccttcctgca   840
ttgtctggcc aatctgaagc cactgttctt cctgcacttg aatccatttt gcaggaacat   900
aaaggtaagt atgttcgatt gatcggtatc gatccagctg cacgtagaag ggttgcagag   960
ttattgattc agaagccagg atctcgaaaa ttaatagagg gtttacgaca tttcagaact  1020
tcttactacc cttcccatcg tgacttattc gagcaatttg caaaaggcca acatcccaga  1080
gtcttgttta tcacttgttc agactctcga ataggaccccca atctcataac acagtctgga  1140
atgggcgagc ttttcgtgat acgtaacgcc ggcaacctca ttcctcccttt tggtgcagct  1200
aacgggggcg aggggggcttc aatagagtac gctatcgctg ccctcaatat cgaacacgtc  1260
gtagtatgcg gacattcaca ttgcggggcc atgaagggac tgttgaagct gaatcaactc  1320
caagaggaca tgccctggt ctatgattgg ttgcagcacg cccaagctac taggagatta  1380
gttttagaca actactctgg ctatgaaact gatgacctgg tagaaatact ggtcgcagaa  1440
aacgtattaa ctcagataga aaatttaaag acttatccca tagtccgtag ccgattgttc  1500
caaggaaaaa tgcaaatatt cgggtggatc tatgaggttg agtccggaga ggtcttgcag  1560
ataagtcgaa ctagctccga cgacacaggg atagacgaat gcccagtcag gttgcccggg  1620
tctcaagaga aagctatctt ggggaggtgt gtcgttcctt taaccgagga agttgctgtc  1680
gcccccctg agcctgaacc tgtgatagct gccgtagccg caccccctgc caactattca  1740
tcacgaggct ggcttggctc aggggctca gtttatggga aggaacaatt cctgaggatg  1800
agacagtcaa tgttccccga tagataa                                      1827
```

<210> SEQ ID NO 29
<211> LENGTH: 1827
<212> TYPE: DNA
<213> ORGANISM: Chlamydomonas reinhardtii

<400> SEQUENCE: 29

```
atgacggtgt cggcttacaa cggccagggc cgcctctcgt ccgaggtcat tacgcaggtc    60
cggagcctcc tgaaccaggg gtaccggatt ggtaccgagc atgccgacaa gcggcgcttt   120
```

-continued

```
cggacgtcgt cctggcagcc ctgcgcgccc attcagagca ccaacgagcg gcaggtcctc      180
tccgagctgg agaactgcct cagcgagcat gaggggagt acgtccgcct gctgggatc       240 gatacgaaca cgcgctcccg ggtcttcgag gctctcatcc agcgccctga cggctcggtg      300
cctgagagcc tcggctcgca gcctgtggcc gtggcgagcg gcgtgggcg gcagtccagc      360 tacgccagcg tgtcgggtaa cctctccgcc gaggtcgtca acaaggtgcg gaacctcctg      420
gcccagggct accggatcgg taccgagcac gccgacaagc gccgctttcg cacgagctcg      480
tggcagagct gcgcccccat tcagtcgagc aacgagcggc aggtgctcgc tgagctggag      540
aactgcctct ccgagcatga gggcgagtac gtgcggctgc tcgggattga tacggcctcg      600
cggtcgcgcg tgtttgaggc gctgatccag gaccccagg gtcctgtcgg ttcggctaag       660
gctgcggctg cccctgtgtc ctcggccacc cccagctcgc attcgtacac ctcgaacggc      720
tcctcgtcgt ccgatgtggc gggtcaggtg cgcgggctcc tcgctcaggg ctaccgcatc      780
agcgctgagg tcgccgataa gcggcggttt cagacgagct cgtggcagtc cctcccggcg      840
ctctcgggtc agagcgaggc caccgtcctc cctgctctcg agtcgattct ccaggagcat      900
aaggggaagt acgtccggct catcgggatt gaccccggctg ctcggcgccg cgtggcggag     960
ctgctgattc agaagcctgg cagccggaag ctcatcgagg ggctccgcca tttccggacg      1020
tcctactacc cctcccaccg cgatctcttc gagcagtttg ccaaggggca gcacccgcgg      1080
gtcctgttca ttacgtgctc cgatagccgc attgacccga acctcatcac gcagagcggt      1140
atgggtgagc tctttgtgat tcgcaacgct ggtaacctca ttcctccctt tggggcggcg      1200
aacggcggcg agggtgcgtc gattgagtac gctatcgccg ccctcaacat tgagcatgtc      1260
gtggtgtgcg gtcatagcca ttgcggcgcg atgaagggcc tcctcaagct gaaccagctg      1320
caggaggaca tgcctctggt gtacgactgg ctgcagcatg ctcaggctac gcggcgcctc      1380
gtcctggaca actactcggg ctacgagacc gatgacctcg tcgagatcct cgtcgcggag      1440
aacgtgctga cccagattga gaacctcaag acgtacccca tcgtgcgctc gcgcctcttc      1500
cagggcaagc tgcagatctt cggttggatt tacgaggtgg agtcggggga ggtcctgcag      1560
atcagccgga cgagctccga cgacaccggg atcgatgagt gccctgtccg cctgccgggc      1620
tcgcaggaga aggccattct gggtcggtgc gtggtccccc tgacggagga ggtggctgtg      1680
gctcctcccg agcctgagcc cgtcattgcg gcggtcgccg cccctccggc taactactcc      1740
agccgggggt ggctcggctc cggggggagc gtctacggca aggagcagtt tctgcgcatg      1800
cggcagtcga tgttcccgga tcgctaa                                         1827
```

<210> SEQ ID NO 30
<211> LENGTH: 190
<212> TYPE: PRT
<213> ORGANISM: Vibrio fishcheri

<400> SEQUENCE: 30

```
Met Ile Lys Lys Ser Asp Phe Leu Gly Ile Pro Ser Glu Glu Tyr Arg
1               5                   10                  15

Gly Ile Leu Ser Leu Arg Tyr Gln Val Phe Lys Arg Arg Leu Glu Trp
            20                  25                  30

Asp Leu Val Ser Glu Asp Asn Leu Glu Ser Asp Glu Tyr Asp Asn Ser
        35                  40                  45

Asn Ala Glu Tyr Ile Tyr Ala Cys Asp Asp Ala Glu Glu Val Asn Gly
    50                  55                  60
```

```
Cys Trp Arg Leu Leu Pro Thr Thr Gly Asp Tyr Met Leu Lys Thr Val
 65                  70                  75                  80

Phe Pro Glu Leu Leu Gly Asp Gln Val Ala Pro Arg Asp Pro Asn Ile
                 85                  90                  95

Val Glu Leu Ser Arg Phe Ala Val Gly Lys Asn Ser Ser Lys Ile Asn
            100                 105                 110

Asn Ser Ala Ser Glu Ile Thr Met Lys Leu Phe Gln Ala Ile Tyr Lys
        115                 120                 125

His Ala Val Ser Gln Gly Ile Thr Glu Tyr Val Thr Val Thr Ser Ile
    130                 135                 140

Ala Ile Glu Arg Phe Leu Lys Arg Ile Lys Val Pro Cys His Arg Ile
145                 150                 155                 160

Gly Asp Lys Glu Ile His Leu Leu Gly Asn Thr Arg Ser Val Val Leu
                165                 170                 175

Ser Met Pro Ile Asn Asp Gln Phe Arg Lys Ala Val Ser Asn
            180                 185                 190
```

<210> SEQ ID NO 31
<211> LENGTH: 573
<212> TYPE: DNA
<213> ORGANISM: Vibrio fishcheri

<400> SEQUENCE: 31

```
atgataaaaa aatcggactt tttgggcatt ccatcagagg agtatagagg tattcttagt    60
cttcgttatc aggtatttaa acgaagactg gagtgggact tggtaagtga ggataatctt   120
gaatcagatg aaatatgataa ctcaaatgca gaatatattt atgcttgtga tgatgcggaa   180
gaggtaaatg gctgttggcg tttgttacct acaacgggtg attacatgtt aaaaactgtt   240
tttcctgaat tgctcggaga tcaagtagcc ccaagagatc caaatatagt cgaattaagc   300
cgttttgctg tgggaaaaaa tagctcaaaa ataaataact ctgctagtga aataacaatg   360
aaattgtttc aagctatata taaacacgca gttagtcaag gtattacaga atatgtaaca   420
gtaacatcaa tagcaataga gcgatttctg aaacgtatta agttccttg tcatcgcatt    480
ggtgataagg agattcattt attaggtaat actagatctg ttgtattgtc tatgcctatt   540
aatgatcagt ttagaaaagc tgtatcaaat taa                                573
```

<210> SEQ ID NO 32
<211> LENGTH: 269
<212> TYPE: PRT
<213> ORGANISM: Vibrio fishcheri

<400> SEQUENCE: 32

```
Met Ile Tyr Asn Thr Gln Asn Leu Arg Gln Thr Ile Gly Lys Asp Lys
  1               5                  10                  15

Glu Met Gly Met Lys Asn Ile Asn Ala Asp Asp Thr Tyr Arg Ile Ile
             20                  25                  30

Asn Lys Ile Lys Ala Cys Arg Ser Asn Asn Asp Ile Asn Gln Cys Leu
         35                  40                  45

Ser Asp Met Thr Lys Met Val His Cys Glu Tyr Tyr Leu Leu Ala Ile
     50                  55                  60

Ile Tyr Pro His Ser Met Val Lys Ser Asp Ser Ile Leu Asp Asn
 65                  70                  75                  80

Tyr Pro Lys Lys Trp Arg Gln Tyr Tyr Asp Asp Ala Asn Leu Ile Lys
                 85                  90                  95

Tyr Asp Pro Ile Val Asp Tyr Ser Asn Ser Asn His Ser Pro Ile Asn
```

```
            100                 105                 110
Trp Asn Ile Phe Glu Asn Asn Ala Val Asn Lys Lys Ser Pro Asn Val
        115                 120                 125

Ile Lys Glu Ala Lys Thr Ser Gly Leu Ile Thr Gly Phe Ser Phe Pro
130                 135                 140

Ile His Thr Ala Asn Asn Gly Phe Gly Met Leu Ser Phe Ala His Ser
145                 150                 155                 160

Glu Lys Asp Asn Tyr Ile Asp Ser Leu Phe Leu His Ala Cys Met Asn
                165                 170                 175

Ile Pro Leu Ile Val Pro Ser Leu Val Asp Asn Tyr Arg Lys Ile Asn
            180                 185                 190

Ile Ala Asn Asn Lys Ser Asn Asn Asp Leu Thr Lys Arg Glu Lys Glu
        195                 200                 205

Cys Leu Ala Trp Ala Cys Glu Gly Lys Ser Ser Trp Asp Ile Ser Lys
210                 215                 220

Ile Leu Gly Cys Ser Glu Arg Thr Val Thr Phe His Leu Thr Asn Ala
225                 230                 235                 240

Gln Met Lys Leu Asn Thr Thr Asn Arg Cys Gln Ser Ile Ser Lys Ala
                245                 250                 255

Ile Leu Thr Gly Ala Ile Asp Cys Pro Tyr Phe Lys Asn
            260                 265

<210> SEQ ID NO 33
<211> LENGTH: 810
<212> TYPE: DNA
<213> ORGANISM: Vibrio fishcheri

<400> SEQUENCE: 33
atgatatata acacgcaaaa cttgcgacaa acaataggta aggataaaga gatgggtatg      60
aaaaacataa atgccgacga cacatacaga ataattaata aaattaaagc ttgtagaagc     120
aataatgata ttaatcaatg cttatctgat atgactaaaa tggtacattg tgaatattat     180
ttactcgcga tcatttatcc tcattctatg gttaaatctg atatttcaat tctagataat     240
taccctaaaa aatggaggca atattatgat gacgctaatt taataaaata tgatcctata     300
gtagattatt ctaactccaa tcattcacca attaattgga atatatttga aaacaatgct     360
gtaaataaaa aatctccaaa tgtaattaaa gaagcgaaaa catcaggtct tatcactggg     420
tttagtttcc ctattcatac ggctaacaat ggcttcggaa tgcttagttt tgcacattca     480
gaaaaagaca actatataga tagtttattt ttacatgcgt gtatgaacat accattaatt     540
gttccttctc tagttgataa ttatcgaaaa ataaatatag caataataa atcaaacaac      600 gatttaacca aaagagaaaa agaatgttta gcgtgggcat gcgaaggaaa aagctcttgg     660
gatatttcaa aaatattagg ctgcagtgag cgtactgtca ctttccattt aaccaatgcg     720
caaatgaaac tcaatacaac aaaccgctgc caaagtattt ctaaagcaat tttaacagga     780
gcaattgatt gcccatactt taaaaattaa                                      810

<210> SEQ ID NO 34
<211> LENGTH: 198
<212> TYPE: DNA
<213> ORGANISM: Vibrio fishcheri

<400> SEQUENCE: 34
tgtcgcaagt tttgcgtgtt atatatcatt aaaacggtaa tggattgaca tttgattcta      60
ataaattgga tttttgtcac actattgtat cgctgggaat acaattactt aacataagca     120
```
cctgtaggat cgtacaggtt tacgcaagaa aatggtttgt tatagtcgaa tgaattcatt         180
aaagaggaga aaggtacc                                                       198

<210> SEQ ID NO 35
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 35
tctagaaata attttgttta actttaagaa ggagatata                                 39

<210> SEQ ID NO 36
<211> LENGTH: 598
<212> TYPE: PRT
<213> ORGANISM: Artificial Sequence
<220> FEATURE:
<223> OTHER INFORMATION: A synthetic protein

<400> SEQUENCE: 36

Met Arg Lys Leu Ile Glu Gly Leu Arg His Phe Arg Thr Ser Tyr Tyr
1               5                   10                  15

Pro Ser His Arg Asp Leu Phe Glu Gln Phe Ala Lys Gly Gln His Pro
            20                  25                  30

Arg Val Leu Phe Ile Thr Cys Ser Asp Ser Arg Ile Asp Pro Asn Leu
        35                  40                  45

Ile Thr Gln Ser Gly Met Gly Glu Leu Phe Val Ile Arg Asn Ala Gly
    50                  55                  60

Asn Leu Ile Pro Pro Phe Gly Ala Ala Asn Gly Gly Glu Gly Ala Ser
65                  70                  75                  80

Ile Glu Tyr Ala Ile Ala Ala Leu Asn Ile Glu His Val Val Val Cys
                85                  90                  95

Gly His Ser His Cys Gly Ala Met Lys Gly Leu Leu Lys Leu Asn Gln
            100                 105                 110

Leu Gln Glu Asp Met Pro Leu Val Tyr Asp Trp Leu Gln His Ala Gln
        115                 120                 125

Ala Thr Arg Arg Leu Val Leu Asp Asn Tyr Ser Gly Tyr Glu Thr Asp
    130                 135                 140

Asp Leu Val Glu Ile Leu Val Ala Glu Asn Val Leu Thr Gln Ile Glu
145                 150                 155                 160

Asn Leu Lys Thr Tyr Pro Ile Val Arg Ser Arg Leu Phe Gln Gly Lys
                165                 170                 175

Leu Gln Ile Phe Gly Trp Ile Tyr Glu Val Glu Ser Gly Glu Val Leu
            180                 185                 190

Gln Ile Ser Arg Thr Ser Ser Asp Asp Thr Gly Ile Asp Glu Cys Pro
        195                 200                 205

Val Arg Leu Pro Gly Ser Gln Glu Lys Ala Ile Leu Gly Arg Cys Val
    210                 215                 220

Val Pro Leu Thr Glu Glu Val Ala Val Ala Pro Glu Pro Glu Pro Glu
225                 230                 235                 240

Val Ile Ala Ala Val Ala Ala Pro Pro Ala Asn Tyr Ser Ser Arg Gly
                245                 250                 255

Trp Leu Ala Pro Glu Gln Gln Gln Arg Ile Tyr Arg Gly Asn Ala Ser
            260                 265                 270

Gly Ser Val Ser Ala Tyr Asn Gly Gln Gly Arg Leu Ser Ser Glu Val

```
                275                 280                 285
Ile Thr Gln Val Arg Ser Leu Leu Asn Gln Gly Tyr Arg Ile Gly Thr
        290                 295                 300
Glu His Ala Asp Lys Arg Arg Phe Arg Thr Ser Ser Trp Gln Pro Cys
305                 310                 315                 320
Ala Pro Ile Gln Ser Thr Asn Glu Arg Gln Val Leu Ser Glu Leu Glu
                325                 330                 335
Asn Cys Leu Ser Glu His Glu Gly Glu Tyr Val Arg Leu Leu Gly Ile
        340                 345                 350
Asp Thr Asn Thr Arg Ser Arg Val Phe Glu Ala Leu Ile Gln Arg Pro
            355                 360                 365
Asp Gly Ser Val Pro Glu Ser Leu Gly Ser Gln Pro Val Ala Val Ala
    370                 375                 380
Ser Gly Gly Gly Arg Gln Ser Ser Tyr Ala Ser Val Ser Gly Asn Leu
385                 390                 395                 400
Ser Ala Glu Val Val Asn Lys Val Arg Asn Leu Leu Ala Gln Gly Tyr
                405                 410                 415
Arg Ile Gly Thr Glu His Ala Asp Lys Arg Arg Phe Arg Thr Ser Ser
        420                 425                 430
Trp Gln Ser Cys Ala Pro Ile Gln Ser Ser Asn Glu Arg Gln Val Leu
    435                 440                 445
Ala Glu Leu Glu Asn Cys Leu Ser Glu His Glu Gly Glu Tyr Val Arg
450                 455                 460
Leu Leu Gly Ile Asp Thr Ala Ser Arg Ser Arg Val Phe Glu Ala Leu
465                 470                 475                 480
Ile Gln Asp Pro Gln Gly Pro Val Gly Ser Ala Lys Ala Ala Ala
                485                 490                 495
Pro Val Ser Ser Ala Thr Pro Ser Ser His Ser Tyr Thr Ser Asn Gly
            500                 505                 510
Ser Ser Ser Ser Asp Val Ala Gly Gln Val Arg Gly Leu Leu Ala Gln
        515                 520                 525
Gly Tyr Arg Ile Ser Ala Glu Val Ala Asp Lys Arg Arg Phe Gln Thr
    530                 535                 540
Ser Ser Trp Gln Ser Leu Pro Ala Leu Ser Gly Gln Ser Glu Ala Thr
545                 550                 555                 560
Val Leu Pro Ala Leu Glu Ser Ile Leu Gln Glu His Lys Gly Lys Tyr
                565                 570                 575
Val Arg Leu Ile Gly Ile Asp Pro Ala Ala Arg Arg Arg Val Ala Glu
            580                 585                 590
Leu Leu Ile Gln Lys Pro
                595

<210> SEQ ID NO 37
<211> LENGTH: 349
<212> TYPE: PRT
<213> ORGANISM: Artificial Sequence
<220> FEATURE:
<223> OTHER INFORMATION: A synthetic protein

<400> SEQUENCE: 37

Met Thr Val Ser Ala Tyr Asn Gly Gln Gly Arg Leu Ser Ser Glu Val
1               5                   10                  15
Ile Thr Gln Val Arg Ser Leu Leu Asn Gln Gly Tyr Arg Ile Gly Thr
                20                  25                  30
Glu His Ala Asp Lys Arg Arg Phe Arg Thr Ser Ser Trp Gln Pro Cys
```

```
            35                  40                  45
Ala Pro Ile Gln Ser Thr Asn Glu Arg Gln Val Leu Ser Glu Leu Glu
 50                  55                  60

Asn Cys Leu Ser Glu His Glu Gly Glu Tyr Val Arg Leu Leu Gly Ile
 65                  70                  75                  80

Asp Thr Asn Thr Arg Ser Arg Val Phe Glu Ala Leu Ile Gln Arg Pro
                 85                  90                  95

Asp Gly Ser Val Pro Glu Ser Leu Gly Ser Gln Pro Val Ala Val Ala
                100                 105                 110

Ser Gly Gly Gly Arg Gln Ser Ser Tyr Ala Ser Val Ser Gly Asn Leu
                115                 120                 125

Ser Ala Glu Val Val Asn Lys Val Arg Asn Leu Leu Ala Gln Gly Tyr
130                 135                 140

Arg Ile Gly Thr Glu His Ala Asp Lys Arg Arg Phe Arg Thr Ser Ser
145                 150                 155                 160

Trp Gln Ser Cys Ala Pro Ile Gln Ser Ser Asn Glu Arg Gln Val Leu
                165                 170                 175

Ala Glu Leu Glu Asn Cys Leu Ser Glu His Glu Gly Glu Tyr Val Arg
                180                 185                 190

Leu Leu Gly Ile Asp Thr Ala Ser Arg Ser Arg Val Phe Glu Ala Leu
                195                 200                 205

Ile Gln Asp Pro Gln Gly Pro Val Gly Ser Ala Lys Ala Ala Ala Ala
                210                 215                 220

Pro Val Ser Ser Ala Thr Pro Ser Ser His Ser Tyr Thr Ser Asn Gly
225                 230                 235                 240

Ser Ser Ser Ser Asp Val Ala Gly Gln Val Arg Gly Leu Leu Ala Gln
                245                 250                 255

Gly Tyr Arg Ile Ser Ala Glu Val Ala Asp Lys Arg Arg Phe Gln Thr
                260                 265                 270

Ser Ser Trp Gln Ser Leu Pro Ala Leu Ser Gly Gln Ser Glu Ala Thr
                275                 280                 285

Val Leu Pro Ala Leu Glu Ser Ile Leu Gln Glu His Lys Gly Lys Tyr
                290                 295                 300

Val Arg Leu Ile Gly Ile Asp Pro Ala Ala Arg Arg Val Ala Glu
305                 310                 315                 320

Leu Leu Ile Gln Lys Pro Gly Ser Gly Gly Ser Val Tyr Gly Lys Glu
                325                 330                 335

Gln Phe Leu Arg Met Arg Gln Ser Met Phe Pro Asp Arg
                340                 345

<210> SEQ ID NO 38
<211> LENGTH: 608
<212> TYPE: PRT
<213> ORGANISM: Artificial Sequence
<220> FEATURE:
<223> OTHER INFORMATION: A synthetic protein

<400> SEQUENCE: 38

Met Thr Val Ser Ala Tyr Asn Gly Gln Gly Arg Leu Ser Ser Glu Val
  1               5                  10                  15

Ile Thr Gln Val Arg Ser Leu Leu Asn Gln Gly Tyr Arg Ile Gly Thr
                 20                  25                  30

Glu His Ala Asp Lys Arg Arg Phe Arg Thr Ser Ser Trp Gln Pro Cys
                 35                  40                  45

Ala Pro Ile Gln Ser Thr Asn Glu Arg Gln Val Leu Ser Glu Leu Glu
```

```
              50                  55                  60
Asn Cys Leu Ser Glu His Glu Gly Glu Tyr Val Arg Leu Leu Gly Ile
 65                  70                  75                  80
Asp Thr Asn Thr Arg Ser Arg Val Phe Glu Ala Leu Ile Gln Arg Pro
                 85                  90                  95
Asp Gly Ser Val Pro Glu Ser Leu Gly Ser Gln Pro Val Ala Val Ala
                100                 105                 110
Ser Gly Gly Arg Gln Ser Ser Tyr Ala Ser Val Ser Gly Asn Leu
                115                 120                 125
Ser Ala Glu Val Val Asn Lys Val Arg Asn Leu Leu Ala Gln Gly Tyr
                130                 135                 140
Arg Ile Gly Thr Glu His Ala Asp Lys Arg Phe Arg Thr Ser Ser
145                 150                 155                 160
Trp Gln Ser Cys Ala Pro Ile Gln Ser Ser Asn Glu Arg Gln Val Leu
                165                 170                 175
Ala Glu Leu Glu Asn Cys Leu Ser Glu His Glu Gly Glu Tyr Val Arg
                180                 185                 190
Leu Leu Gly Ile Asp Thr Ala Ser Arg Ser Arg Val Phe Glu Ala Leu
                195                 200                 205
Ile Gln Asp Pro Gln Gly Pro Val Gly Ser Ala Lys Ala Ala Ala Ala
210                 215                 220
Pro Val Ser Ser Ala Thr Pro Ser Ser His Ser Tyr Thr Ser Asn Gly
225                 230                 235                 240
Ser Ser Ser Ser Asp Val Ala Gly Gln Val Arg Gly Leu Leu Ala Gln
                245                 250                 255
Gly Tyr Arg Ile Ser Ala Glu Val Ala Asp Lys Arg Phe Gln Thr
                260                 265                 270
Ser Ser Trp Gln Ser Leu Pro Ala Leu Ser Gly Gln Ser Glu Ala Thr
                275                 280                 285
Val Leu Pro Ala Leu Glu Ser Ile Leu Gln Glu His Lys Gly Lys Tyr
                290                 295                 300
Val Arg Leu Ile Gly Ile Asp Pro Ala Ala Arg Arg Arg Val Ala Glu
305                 310                 315                 320
Leu Leu Ile Gln Lys Pro Gly Ser Arg Lys Leu Ile Glu Gly Leu Arg
                325                 330                 335
His Phe Arg Thr Ser Tyr Tyr Pro Ser His Arg Asp Leu Phe Glu Gln
                340                 345                 350
Phe Ala Lys Gly Gln His Pro Arg Val Leu Phe Ile Thr Cys Ser Asp
                355                 360                 365
Ser Arg Ile Asp Pro Asn Leu Ile Thr Gln Ser Gly Met Gly Glu Leu
                370                 375                 380
Phe Val Ile Arg Asn Ala Gly Asn Leu Ile Pro Pro Phe Gly Ala Ala
385                 390                 395                 400
Asn Gly Gly Glu Gly Ala Ser Ile Glu Tyr Ala Ile Ala Ala Leu Asn
                405                 410                 415
Ile Glu His Val Val Cys Gly His Ser His Cys Gly Ala Met Lys
                420                 425                 430
Gly Leu Leu Lys Leu Asn Gln Leu Gln Glu Asp Met Pro Leu Val Tyr
                435                 440                 445
Asp Trp Leu Gln His Ala Gln Ala Thr Arg Arg Leu Val Leu Asp Asn
                450                 455                 460
Tyr Ser Gly Tyr Glu Thr Asp Asp Leu Val Glu Ile Leu Val Ala Glu
465                 470                 475                 480
```

```
Asn Val Leu Thr Gln Ile Glu Asn Leu Lys Thr Tyr Pro Ile Val Arg
            485                 490                 495
Ser Arg Leu Phe Gln Gly Lys Leu Gln Ile Phe Gly Trp Ile Tyr Glu
        500                 505                 510
Val Glu Ser Gly Glu Val Leu Gln Ile Ser Arg Thr Ser Ser Asp Asp
        515                 520                 525
Thr Gly Ile Asp Glu Cys Pro Val Arg Leu Pro Gly Ser Gln Glu Lys
    530                 535                 540
Ala Ile Leu Gly Arg Cys Val Val Pro Leu Thr Glu Val Ala Val
545                 550                 555                 560
Ala Pro Pro Glu Pro Glu Pro Val Ile Ala Ala Val Ala Ala Pro Pro
                565                 570                 575
Ala Asn Tyr Ser Ser Arg Gly Trp Leu Gly Ser Gly Ser Val Tyr
            580                 585                 590
Gly Lys Glu Gln Phe Leu Arg Met Arg Gln Ser Met Phe Pro Asp Arg
        595                 600                 605
```

<210> SEQ ID NO 39
<211> LENGTH: 23
<212> TYPE: DNA
<213> ORGANISM: Artificial Sequence
<220> FEATURE:
<223> OTHER INFORMATION: A synthetic primer

<400> SEQUENCE: 39
ggtgcactac tagtacaatc tgc                                    23

<210> SEQ ID NO 40
<211> LENGTH: 25
<212> TYPE: DNA
<213> ORGANISM: Artificial Sequence
<220> FEATURE:
<223> OTHER INFORMATION: A synthetic primer

<400> SEQUENCE: 40
gtgaaatacc gcactagtgc gtaag                                  25

<210> SEQ ID NO 41
<211> LENGTH: 28
<212> TYPE: DNA
<213> ORGANISM: Artificial Sequence
<220> FEATURE:
<223> OTHER INFORMATION: A synthetic primer

<400> SEQUENCE: 41
ctttcatctt gaattccgac tctttagg                               28

<210> SEQ ID NO 42
<211> LENGTH: 20
<212> TYPE: DNA
<213> ORGANISM: Artificial Sequence
<220> FEATURE:
<223> OTHER INFORMATION: A synthetic primer

<400> SEQUENCE: 42
gctcggcata tgctaacctc                                        20

<210> SEQ ID NO 43
<211> LENGTH: 32
<212> TYPE: DNA
<213> ORGANISM: Artificial Sequence
<220> FEATURE:

<223> OTHER INFORMATION: A synthetic primer

<400> SEQUENCE: 43
gggaggttag catatgctct agaagctgca gg                32

<210> SEQ ID NO 44
<211> LENGTH: 23
<212> TYPE: DNA
<213> ORGANISM: Artificial Sequence
<220> FEATURE:
<223> OTHER INFORMATION: A synthetic primer

<400> SEQUENCE: 44
ctactgagtc cgaagctttc agc                23

<210> SEQ ID NO 45
<211> LENGTH: 25
<212> TYPE: DNA
<213> ORGANISM: Artificial Sequence
<220> FEATURE:
<223> OTHER INFORMATION: A synthetic primer

<400> SEQUENCE: 45
gaattataac catatgcatc ctagg                25

<210> SEQ ID NO 46
<211> LENGTH: 21
<212> TYPE: DNA
<213> ORGANISM: Artificial Sequence
<220> FEATURE:
<223> OTHER INFORMATION: A synthetic primer

<400> SEQUENCE: 46
tcccgtctag acagcgtaat g                21

<210> SEQ ID NO 47
<211> LENGTH: 23
<212> TYPE: DNA
<213> ORGANISM: Artificial Sequence
<220> FEATURE:
<223> OTHER INFORMATION: A synthetic primer

<400> SEQUENCE: 47
gagtatcact catatgcgca agc                23

<210> SEQ ID NO 48
<211> LENGTH: 21
<212> TYPE: DNA
<213> ORGANISM: Artificial Sequence
<220> FEATURE:
<223> OTHER INFORMATION: A synthetic primer

<400> SEQUENCE: 48
cttcgggatc cgctagcatt g                21

<210> SEQ ID NO 49
<211> LENGTH: 22
<212> TYPE: DNA
<213> ORGANISM: Artificial Sequence
<220> FEATURE:
<223> OTHER INFORMATION: A synthetic primer

<400> SEQUENCE: 49
tagcgaggca agatctgtga gc                22

```
<210> SEQ ID NO 50
<211> LENGTH: 24
<212> TYPE: DNA
<213> ORGANISM: Artificial Sequence
<220> FEATURE:
<223> OTHER INFORMATION: A synthetic primer

<400> SEQUENCE: 50
cctgcagctt ctagagctgc tgtg                                            24

<210> SEQ ID NO 51
<211> LENGTH: 24
<212> TYPE: DNA
<213> ORGANISM: Artificial Sequence
<220> FEATURE:
<223> OTHER INFORMATION: A synthetic primer

<400> SEQUENCE: 51
gttgttgttc ggatcccaac caac                                            24

<210> SEQ ID NO 52
<211> LENGTH: 34
<212> TYPE: DNA
<213> ORGANISM: Artificial Sequence
<220> FEATURE:
<223> OTHER INFORMATION: A synthetic primer

<400> SEQUENCE: 52
cccagatctg gaggcagtgt ctacggcaag gaac                                 34

<210> SEQ ID NO 53
<211> LENGTH: 25
<212> TYPE: DNA
<213> ORGANISM: Artificial Sequence
<220> FEATURE:
<223> OTHER INFORMATION: A synthetic primer

<400> SEQUENCE: 53
cgtggccatg gcttcttggg agagc                                           25

<210> SEQ ID NO 54
<211> LENGTH: 28
<212> TYPE: DNA
<213> ORGANISM: Artificial Sequence
<220> FEATURE:
<223> OTHER INFORMATION: A synthetic primer

<400> SEQUENCE: 54
gcccttgtca gatctcgcaa gctcatcg                                        28

<210> SEQ ID NO 55
<211> LENGTH: 25
<212> TYPE: DNA
<213> ORGANISM: Artificial Sequence
<220> FEATURE:
<223> OTHER INFORMATION: A synthetic primer

<400> SEQUENCE: 55
ctagcgagca tatgaccgtg agcgc                                           25

<210> SEQ ID NO 56
<211> LENGTH: 27
<212> TYPE: DNA
<213> ORGANISM: Artificial Sequence
<220> FEATURE:
<223> OTHER INFORMATION: A synthetic primer
```

```
<400> SEQUENCE: 56
caggatcctc ccggcttttg ttagagc                                          27

<210> SEQ ID NO 57
<211> LENGTH: 19
<212> TYPE: DNA
<213> ORGANISM: Artificial Sequence
<220> FEATURE:
<223> OTHER INFORMATION: A synthetic primer

<400> SEQUENCE: 57
cagcggccgc gcctagtgc                                                   19

<210> SEQ ID NO 58
<211> LENGTH: 29
<212> TYPE: DNA
<213> ORGANISM: Artificial Sequence
<220> FEATURE:
<223> OTHER INFORMATION: A synthetic primer

<400> SEQUENCE: 58
gcttgcgcat ctcgagtgat actcgggac                                        29

<210> SEQ ID NO 59
<211> LENGTH: 29
<212> TYPE: DNA
<213> ORGANISM: Artificial Sequence
<220> FEATURE:
<223> OTHER INFORMATION: A synthetic primer

<400> SEQUENCE: 59
gcggcaattc tagataggat cgaagcatc                                        29

<210> SEQ ID NO 60
<211> LENGTH: 29
<212> TYPE: DNA
<213> ORGANISM: Artificial Sequence
<220> FEATURE:
<223> OTHER INFORMATION: A synthetic primer

<400> SEQUENCE: 60
tacccatgga ctcaagcgct cattgccag                                        29

<210> SEQ ID NO 61
<211> LENGTH: 26
<212> TYPE: DNA
<213> ORGANISM: Artificial Sequence
<220> FEATURE:
<223> OTHER INFORMATION: A synthetic primer

<400> SEQUENCE: 61
ggtaccgagc tcgagttgac ataagc                                           26

<210> SEQ ID NO 62
<211> LENGTH: 21
<212> TYPE: DNA
<213> ORGANISM: Artificial Sequence
<220> FEATURE:
<223> OTHER INFORMATION: A synthetic primer

<400> SEQUENCE: 62
tccgcggctc tagagccgat c                                                21

<210> SEQ ID NO 63
<211> LENGTH: 20
```

-continued

<210> SEQ ID NO 63
<211> LENGTH: 20
<212> TYPE: DNA
<213> ORGANISM: Artificial Sequence
<220> FEATURE:
<223> OTHER INFORMATION: A synthetic primer

<400> SEQUENCE: 63
tgcctattgc ggttggaatg                                           20

<210> SEQ ID NO 64
<211> LENGTH: 20
<212> TYPE: DNA
<213> ORGANISM: Artificial Sequence
<220> FEATURE:
<223> OTHER INFORMATION: A synthetic primer

<400> SEQUENCE: 64
aatcatgatg cacgcccttg                                           20

<210> SEQ ID NO 65
<211> LENGTH: 20
<212> TYPE: DNA
<213> ORGANISM: Artificial Sequence
<220> FEATURE:
<223> OTHER INFORMATION: A synthetic primer

<400> SEQUENCE: 65
aatcatgatg cacgcccttg                                           20

<210> SEQ ID NO 66
<211> LENGTH: 20
<212> TYPE: DNA
<213> ORGANISM: Artificial Sequence
<220> FEATURE:
<223> OTHER INFORMATION: A synthetic primer

<400> SEQUENCE: 66
ttagccgatt tgagcatggc                                           20

<210> SEQ ID NO 67
<211> LENGTH: 26
<212> TYPE: DNA
<213> ORGANISM: Artificial Sequence
<220> FEATURE:
<223> OTHER INFORMATION: A synthetic primer

<400> SEQUENCE: 67
cagctttgaa cattgagcat gttgtg                                    26

<210> SEQ ID NO 68
<211> LENGTH: 21
<212> TYPE: DNA
<213> ORGANISM: Artificial Sequence
<220> FEATURE:
<223> OTHER INFORMATION: A synthetic primer

<400> SEQUENCE: 68
attgccgcga taaatccgct g                                         21

<210> SEQ ID NO 69
<211> LENGTH: 539
<212> TYPE: PRT
<213> ORGANISM: Synechococcus elongatus

<400> SEQUENCE: 69

Met Pro Ser Pro Thr Thr Val Pro Val Ala Thr Ala Gly Arg Leu Ala
1               5                   10                  15

```
Glu Pro Tyr Ile Asp Pro Ala Ala Gln Val His Ala Ile Ala Ser Ile
                 20                  25                  30

Ile Gly Asp Val Arg Ile Ala Ala Gly Val Arg Val Ala Ala Gly Val
             35                  40                  45

Ser Ile Arg Ala Asp Glu Gly Ala Pro Phe Gln Val Gly Lys Glu Ser
         50                  55                  60

Ile Leu Gln Glu Gly Ala Val Ile His Gly Leu Glu Tyr Gly Arg Val
 65                  70                  75                  80

Leu Gly Asp Asp Gln Ala Asp Tyr Ser Val Trp Ile Gly Gln Arg Val
                 85                  90                  95

Ala Ile Thr His Lys Ala Leu Ile His Gly Pro Ala Tyr Leu Gly Asp
            100                 105                 110

Asp Cys Phe Val Gly Phe Arg Ser Thr Val Phe Asn Ala Arg Val Gly
            115                 120                 125

Ala Gly Ser Val Ile Met Met His Ala Leu Val Gln Asp Val Glu Ile
130                 135                 140

Pro Pro Gly Arg Tyr Val Pro Ser Gly Ala Ile Ile Thr Thr Gln Gln
145                 150                 155                 160

Gln Ala Asp Arg Leu Pro Glu Val Arg Pro Glu Asp Arg Glu Phe Ala
                165                 170                 175

Arg His Ile Ile Gly Ser Pro Val Ile Val Arg Ser Thr Pro Ala
                180                 185                 190

Ala Thr Ala Asp Phe His Ser Thr Pro Thr Pro Ser Pro Leu Arg Pro
            195                 200                 205

Ser Ser Ser Glu Ala Thr Thr Val Ser Ala Tyr Asn Gly Gln Gly Arg
210                 215                 220

Leu Ser Ser Glu Val Ile Thr Gln Val Arg Ser Leu Leu Asn Gln Gly
225                 230                 235                 240

Tyr Arg Ile Gly Thr Glu His Ala Asp Lys Arg Arg Phe Arg Thr Ser
                245                 250                 255

Ser Trp Gln Pro Cys Ala Pro Ile Gln Ser Thr Asn Glu Arg Gln Val
            260                 265                 270

Leu Ser Glu Leu Glu Asn Cys Leu Ser Glu His Glu Gly Glu Tyr Val
            275                 280                 285

Arg Leu Leu Gly Ile Asp Thr Asn Thr Arg Ser Arg Val Phe Glu Ala
290                 295                 300

Leu Ile Gln Arg Pro Asp Gly Ser Val Pro Glu Ser Leu Gly Ser Gln
305                 310                 315                 320

Pro Val Ala Val Ala Ser Gly Gly Arg Gln Ser Ser Tyr Ala Ser
                325                 330                 335

Val Ser Gly Asn Leu Ser Ala Glu Val Val Asn Lys Val Arg Asn Leu
            340                 345                 350

Leu Ala Gln Gly Tyr Arg Ile Gly Thr Glu His Ala Asp Lys Arg Arg
            355                 360                 365

Phe Arg Thr Ser Ser Trp Gln Ser Cys Ala Pro Ile Gln Ser Ser Asn
            370                 375                 380

Glu Arg Gln Val Leu Ala Glu Leu Glu Asn Cys Leu Ser Glu His Glu
385                 390                 395                 400

Gly Glu Tyr Val Arg Leu Leu Gly Ile Asp Thr Ala Ser Arg Ser Arg
                405                 410                 415

Val Phe Glu Ala Leu Ile Gln Asp Pro Gln Gly Pro Val Gly Ser Ala
            420                 425                 430
```

```
Lys Ala Ala Ala Ala Pro Val Ser Ala Thr Pro Ser Ser His Ser
            435                 440                 445

Tyr Thr Ser Asn Gly Ser Ser Ser Asp Val Ala Gly Gln Val Arg
450                 455                 460

Gly Leu Leu Ala Gln Gly Tyr Arg Ile Ser Ala Glu Val Ala Asp Lys
465                 470                 475                 480

Arg Arg Phe Gln Thr Ser Ser Trp Gln Ser Leu Pro Ala Leu Ser Gly
            485                 490                 495

Gln Ser Glu Ala Thr Val Leu Pro Ala Leu Gly Ser Ile Leu Gln Glu
            500                 505                 510

His Lys Gly Lys Tyr Val Arg Leu Ile Gly Ile Asp Pro Ala Ala Arg
            515                 520                 525

Arg Arg Val Ala Glu Leu Leu Ile Gln Lys Pro
    530                 535

<210> SEQ ID NO 70
<211> LENGTH: 161
<212> TYPE: PRT
<213> ORGANISM: Synechococcus elongatus

<400> SEQUENCE: 70

Met His Leu Pro Pro Leu Glu Pro Pro Ile Ser Asp Arg Tyr Phe Ala
1               5                   10                  15

Ser Gly Glu Val Thr Ile Ala Ala Asp Val Val Ile Ala Pro Gly Val
                20                  25                  30

Leu Leu Ile Ala Glu Ala Asp Ser Arg Ile Glu Ile Ala Ser Gly Val
            35                  40                  45

Cys Ile Gly Leu Gly Ser Val Ile His Ala Arg Gly Gly Ala Ile Ile
    50                  55                  60

Ile Gln Ala Gly Ala Leu Leu Ala Ala Gly Val Leu Ile Val Gly Gln
65                  70                  75                  80

Ser Ile Val Gly Arg Gln Ala Cys Leu Gly Ala Ser Thr Thr Leu Val
                85                  90                  95

Asn Thr Ser Ile Glu Ala Gly Gly Val Thr Ala Pro Gly Ser Leu Leu
            100                 105                 110

Ser Ala Glu Thr Pro Pro Thr Thr Ala Thr Val Ser Ser Ser Glu Pro
    115                 120                 125

Ala Gly Arg Ser Pro Gln Ser Ser Ala Ile Ala His Pro Thr Lys Val
130                 135                 140

Tyr Gly Lys Glu Gln Phe Leu Arg Met Arg Gln Ser Met Phe Pro Asp
145                 150                 155                 160

Arg

<210> SEQ ID NO 71
<211> LENGTH: 272
<212> TYPE: PRT
<213> ORGANISM: Synechococcus elongatus

<400> SEQUENCE: 71

Met Arg Lys Leu Ile Glu Gly Leu Arg His Phe Arg Thr Ser Tyr Tyr
1               5                   10                  15

Pro Ser His Arg Asp Leu Phe Glu Gln Phe Ala Lys Gly Gln His Pro
                20                  25                  30

Arg Val Leu Phe Ile Thr Cys Ser Asp Ser Arg Ile Asp Pro Asn Leu
            35                  40                  45

Ile Thr Gln Ser Gly Met Gly Glu Leu Phe Val Ile Arg Asn Ala Gly
```

```
                50                  55                  60
Asn Leu Ile Pro Pro Phe Gly Ala Ala Asn Gly Gly Glu Gly Ala Ser
 65                  70                  75                  80

Ile Glu Tyr Ala Ile Ala Ala Leu Asn Ile Glu His Val Val Cys
                 85                  90                  95

Gly His Ser His Cys Gly Ala Met Lys Gly Leu Leu Lys Leu Asn Gln
                100                 105                 110

Leu Gln Glu Asp Met Pro Leu Val Tyr Asp Trp Leu Gln His Ala Gln
            115                 120                 125

Ala Thr Arg Arg Leu Val Leu Asp Asn Tyr Ser Gly Tyr Glu Thr Asp
        130                 135                 140

Asp Leu Val Glu Ile Leu Val Ala Glu Asn Val Leu Thr Gln Ile Glu
145                 150                 155                 160

Asn Leu Lys Thr Tyr Pro Ile Val Arg Ser Arg Leu Phe Gln Gly Lys
                165                 170                 175

Leu Gln Ile Phe Gly Trp Ile Tyr Glu Val Glu Ser Gly Glu Val Leu
            180                 185                 190

Gln Ile Ser Arg Thr Ser Ser Asp Asp Thr Gly Ile Asp Glu Cys Pro
        195                 200                 205

Val Arg Leu Pro Gly Ser Gln Glu Lys Ala Ile Leu Gly Arg Cys Val
    210                 215                 220

Val Pro Leu Thr Glu Glu Val Ala Val Ala Pro Pro Glu Pro Glu Pro
225                 230                 235                 240

Val Ile Ala Ala Val Ala Ala Pro Pro Ala Asn Tyr Ser Ser Arg Gly
                245                 250                 255

Trp Leu Ala Pro Glu Gln Gln Gln Arg Ile Tyr Arg Gly Asn Ala Ser
            260                 265                 270

<210> SEQ ID NO 72
<211> LENGTH: 2056
<212> TYPE: DNA
<213> ORGANISM: Artificial Sequence
<220> FEATURE:
<223> OTHER INFORMATION: A synthetic oligonucleotide

<400> SEQUENCE: 72
agccgcggca gtcaagcgcg ccatgtgcgc gattgtcagg aacgaccggt tgatgcagct    60
gtcattgcca tcatcgatac ggtcaacgtg gaaaaccgct ccgtctacga caaacgcgag   120
cacagctaat gggcagggat tgaatccctg ctggtcattg atctggattg agcccaggct   180
tgggaggtta gcatatgacc gtgagcgctt ataacggcca aggccgactc agttccgaag   240
tcatcaccca gtccggagt ttgctgaacc agggctatcg gattgggacg gaacatgcgg   300
acaagcgccg cttccggact agctcttggc agccctgcgc gccgattcaa agcacgaacg   360
agcgccaggt cttgagcgaa ctggaaaatt gtctgagcga cacgaaggt gaatacgttc   420 gcttgctcgg catcgatacc aatactcgca gccgtgtttt tgaagccctg attcaacggc   480
ccgatggttc ggttcctgaa tcgctgggga gccaaccggt ggcagtcgct tccggtggtg   540
gccgtcagag cagctatgcc agcgtcagcg gcaacctctc agcagaagtg gtcaataaag   600
tccgcaacct cttagcccaa ggctatcgga ttggacgga acatgcagac aagcgccgct   660
ttcggactag ctcttggcag tcctgcgcac cgattcaaag ttcgaatgag cgccaggttc   720
tggctgaact ggaaaactgt ctgagcgagc acgaaggtga gtacgttcgc tgctgggca   780 tcgacactgc tagccgcagt cgtgtttttg aagccctgat ccaagatccc caaggaccgg   840
```

```
tgggttccgc caaagcggcc gccgcacctg tgagttcggc aacgcccagc agccacagct    900
acacctcaaa tggatcgagt tcgagcgatg tcgctggaca ggttcggggt ctgctagccc    960
aaggctaccg gatcagtgcg gaagtcgccg ataagcgtcg cttccaaacc agctcttggc   1020
agagtttgcc ggctctgagt ggccagagcg aagcaactgt cttgcctgct ttggagtcaa   1080
ttctgcaaga gcacaagggt aagtatgtgc gcctgattgg gattgaccct gcggctcgtc   1140
gtcgcgtggc tgaactgttg attcaaaagc cgggatctcg caagctcatc gagggttac    1200 ggcatttccg tacgtcctac tacccgtctc atcgggacct gttcgagcag tttgccaaag   1260
gtcagcaccc tcgagtcctg ttcattacct gctcagactc gcgcattgac cctaacctca   1320
ttacccagtc gggcatgggt gagctgttcg tcattcgcaa cgctggcaat ctgatcccgc   1380
ccttcggtgc cgccaacggt ggtgaagggg catcgatcga atacgcgatc gcagctttga   1440
acattgagca tgttgtggtc tgcggtcact cgcactgcgg tgcgatgaaa gggctgctca   1500
agctcaatca gctgcaagag gacatgccgc tggtctatga ctggctgcag catgcccaag   1560
ccacccgccg cctagtcttg gataactaca gcggttatga gactgacgac ttggtagaga   1620
ttctggtcgc cgagaatgtg ctgacgcaga tcgagaacct taagacctac ccgatcgtgc   1680
gatcgcgcct ttccaaggc aagctgcaga tttttggctg gatttatgaa gttgaaagcg   1740
gcgaggtctt gcagattagc cgtaccagca gtgatgacac aggcattgat gaatgtccag   1800
tgcgtttgcc cggcagccag gagaaagcca ttctcggtcg ttgtgtcgtc ccctgaccg   1860 aagaagtggc cgttgctcca ccagagccgg agcctgtgat cgcggctgtg gcggctccac   1920
ccgccaacta ctccagtcgc ggttggttgg gatctggagg cagtgtctac ggcaaggaac   1980 agttttgcg gatgcgccag agcatgttcc ccgatcgcta agatgtgcac agcagctcta   2040
ggagctgcag ggtact                                                   2056

<210> SEQ ID NO 73
<211> LENGTH: 129
<212> TYPE: DNA
<213> ORGANISM: Artificial Sequence
<220> FEATURE:
<223> OTHER INFORMATION: A synthetic oligonucleotide

<400> SEQUENCE: 73
agccgcggca gtcaagcgcg ccatgtgcgc gattgtcagg aacgaccggt tgatgcagct     60
gtcattgcca tcatcgatac ggtcaacgtg gaaaaccgct ccgtctacga caaacgcgag    120
cacagctaa                                                            129

<210> SEQ ID NO 74

<400> SEQUENCE: 74

000

<210> SEQ ID NO 75
<211> LENGTH: 95
<212> TYPE: PRT
<213> ORGANISM: Artificial Sequence
<220> FEATURE:
<223> OTHER INFORMATION: A synthetic protein

<400> SEQUENCE: 75

Thr Val Ser Ala Tyr Asn Gly Gln Gly Arg Leu Ser Ser Glu Val Ile
1               5                   10                  15

Thr Gln Val Arg Ser Leu Leu Asn Gln Gly Tyr Arg Ile Gly Thr Glu
```

```
                    20                  25                  30
His Ala Asp Lys Arg Arg Phe Arg Thr Ser Ser Trp Gln Pro Cys Ala
                35                  40                  45

Pro Ile Gln Ser Thr Asn Glu Arg Gln Val Leu Ser Glu Leu Glu Asn
            50                  55                  60

Cys Leu Ser Glu His Glu Gly Glu Tyr Val Arg Leu Leu Gly Ile Asp
65                  70                  75                  80

Thr Asn Thr Arg Ser Arg Val Phe Glu Ala Leu Ile Gln Arg Pro
                85                  90                  95

<210> SEQ ID NO 76
<211> LENGTH: 84
<212> TYPE: PRT
<213> ORGANISM: Artificial Sequence
<220> FEATURE:
<223> OTHER INFORMATION: A synthetic protein

<400> SEQUENCE: 76

Ser Ala Glu Val Val Asn Lys Val Arg Asn Leu Leu Ala Gln Gly Tyr
1               5                   10                  15

Arg Ile Gly Thr Glu His Ala Asp Lys Arg Arg Phe Arg Thr Ser Ser
            20                  25                  30

Trp Gln Ser Cys Ala Pro Ile Gln Ser Ser Asn Glu Arg Gln Val Leu
        35                  40                  45

Ala Glu Leu Glu Asn Cys Leu Ser Glu His Glu Gly Glu Tyr Val Arg
    50                  55                  60

Leu Leu Gly Ile Asp Thr Ala Ser Arg Ser Arg Val Phe Glu Ala Leu
65                  70                  75                  80

Ile Gln Asp Pro

<210> SEQ ID NO 77
<211> LENGTH: 85
<212> TYPE: PRT
<213> ORGANISM: Artificial Sequence
<220> FEATURE:
<223> OTHER INFORMATION: A synthetic protein

<400> SEQUENCE: 77

Ser Ser Ser Asp Val Ala Gly Gln Val Arg Gly Leu Leu Ala Gln Gly
1               5                   10                  15

Tyr Arg Ile Ser Ala Glu Val Ala Asp Lys Arg Arg Phe Gln Thr Ser
            20                  25                  30

Ser Trp Gln Ser Leu Pro Ala Leu Ser Gly Gln Ser Glu Ala Thr Val
        35                  40                  45

Leu Pro Ala Leu Glu Ser Ile Leu Gln Glu His Lys Gly Lys Tyr Val
    50                  55                  60

Arg Leu Ile Gly Ile Asp Pro Ala Ala Arg Arg Arg Val Ala Glu Leu
65                  70                  75                  80

Leu Ile Gln Lys Pro
                85
```